(12) United States Patent
Wikswo et al.

(10) Patent No.: US 10,444,223 B2
(45) Date of Patent: *Oct. 15, 2019

(54) INTEGRATED ORGAN-ON-CHIP SYSTEMS AND APPLICATIONS OF THE SAME

(71) Applicant: VANDERBILT UNIVERSITY, Nashville, TN (US)

(72) Inventors: John P. Wikswo, Brentwood, TN (US); David E. Cliffel, Nashville, TN (US); Dmitry A. Markov, Nashville, TN (US); John A. McLean, Nashville, TN (US); Lisa Joy McCawley, Nashville, TN (US); Phillip C. Samson, Nashville, TN (US); Ronald S. Reiserer, Nashville, TN (US); Frank Emmanuel Block, Nashville, TN (US); Jennifer Robin McKenzie, Nashville, TN (US)

(73) Assignee: VANDERBILT UNIVERSITY, Nashville, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/049,025

(22) Filed: Jul. 30, 2018

(65) Prior Publication Data
US 2019/0064144 A1 Feb. 28, 2019

Related U.S. Application Data

(63) Continuation of application No. 14/363,074, filed as application No. PCT/US2012/068771 on Dec. 10, 2012, now Pat. No. 10,078,075.

(Continued)

(51) Int. Cl.
*B01L 3/00* (2006.01)
*G01N 33/50* (2006.01)
(Continued)

(52) U.S. Cl.
CPC ....... *G01N 33/5005* (2013.01); *A01N 1/0247* (2013.01); *B01L 3/5027* (2013.01);
(Continued)

(58) Field of Classification Search
CPC ......... B01L 2300/0867; B01L 2200/10; B01L 2400/0644; B01L 2400/0622;
(Continued)

(56) References Cited

U.S. PATENT DOCUMENTS 4,629,686 A * 12/1986 Gruenberg ............. C12M 33/07
435/286.5
9,874,285 B2 * 1/2018 Block, III ........... F04B 43/1269
(Continued)

*Primary Examiner* — Betty J Forman
(74) *Attorney, Agent, or Firm* — Locke Lord LLP; Tim Tingkang Xia, Esq.

(57) ABSTRACT

A microclinical analyzer usable for analysis of one or more bio-objects, each bio-object including an organ or a group of cells includes a fluidic network having a plurality of fluidic switches, a plurality of fluidic paths in fluid communication with the plurality of fluidic switches, and one or more on-chip pumps coupled to corresponding fluidic paths; a sensor array coupled to the fluidic network; and a microcontroller for individually controlling the plurality of fluidic switches and the one or more on-chip pumps of the fluidic network as so to operably and selectively deliver an effluent of at least one bio-object to the sensor array for detecting properties of the effluent, or to a predetermined outlet destination.

14 Claims, 51 Drawing Sheets

Related U.S. Application Data

(60) Provisional application No. 61/717,441, filed on Oct. 23, 2012, provisional application No. 61/697,204, filed on Sep. 5, 2012, provisional application No. 61/569,145, filed on Dec. 9, 2011.

(51) Int. Cl.
*G01N 35/10* (2006.01)
*A01N 1/02* (2006.01)
*C12M 3/06* (2006.01)

(52) U.S. Cl.
CPC .... *G01N 35/1095* (2013.01); *B01L 3/502715* (2013.01); *B01L 2300/0864* (2013.01); *B01L 2300/0867* (2013.01); *B01L 2300/0877* (2013.01); *B01L 2400/0481* (2013.01); *B01L 2400/0487* (2013.01); *B01L 2400/0622* (2013.01); *C12M 23/16* (2013.01)

(58) Field of Classification Search
CPC .......... B01L 3/5027; B01L 2300/0636; C12M 23/16; C12M 21/08; C12M 29/10; C12M 23/42; C12M 29/00; C12M 41/46; C12M 41/48
See application file for complete search history.

(56) References Cited

U.S. PATENT DOCUMENTS

| | | | |
|---|---|---|---|
| 10,023,832 B2* | 7/2018 | Wikswo | C12M 23/16 |
| 10,078,075 B2* | 9/2018 | Wikswo | B01L 3/5027 |
| 2005/0043894 A1* | 2/2005 | Fernandez | A61B 5/0215 |
| | | | 702/19 |
| 2005/0158845 A1* | 7/2005 | Wikswo | G01N 33/5005 |
| | | | 435/287.1 |
| 2006/0205061 A1* | 9/2006 | Roukes | B01L 3/5027 |
| | | | 435/287.2 |

* cited by examiner

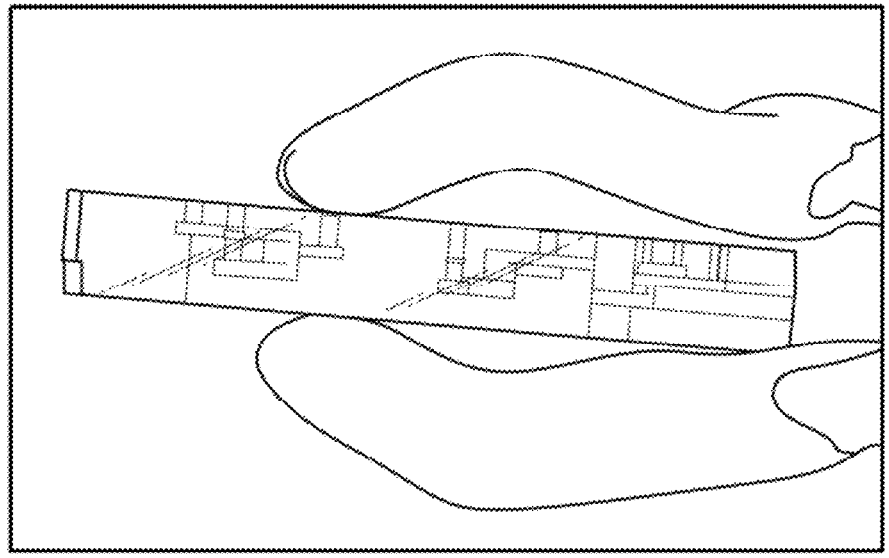
(A)
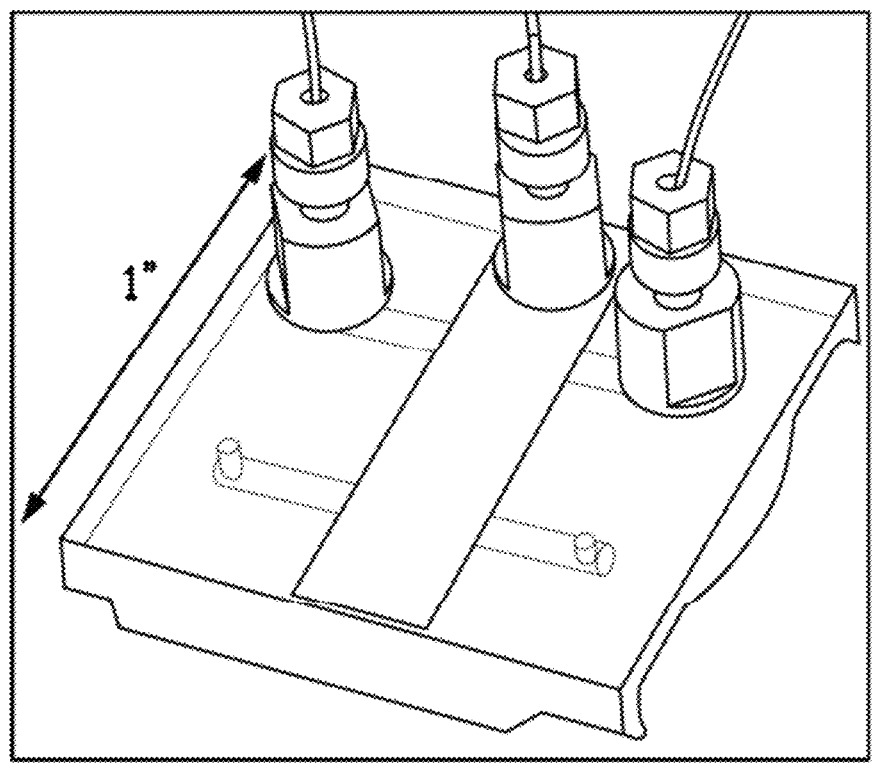
(B)
FIG. 20

| Organ/Tissue | Cell Type (Model) | Cell Name | Source |
|---|---|---|---|
| Brain | Neurons | Primary Culture | Murine |
| Brain | Neurons/Glia | Primary Culture | Murine |
| Pancreas | Islets | Primary Culture | Murine |
| Brain | Neuroblastomas | SK N SH | Human |
| Breast | Mammory Epithelial | MCF 10A | Human |
| Small Intestine | Enterocytes | Caco-2 | Human |
| Liver | Hepatocytes | HepG2 | Human |
| Blood Vessels | Umbilical Venous Cord Endothelial | HUVEC | Human |
| Blood | T cells | Jurkat | Human |
| Ovary | Ovarian | CHO | Hamster |
| Connective | Fibroblasts | 3T3 | Murine |
| Lung | Lung epithelials | LLC | Murine |
| Neuroendocrine | Chromaffin Pheochromocytoma | PC-12 | Murine |
| Blood | Airway Macrophages | RAW 264.7 | Murine |

FIG. 26

INTEGRATED ORGAN-ON-CHIP SYSTEMS AND APPLICATIONS OF THE SAME

CROSS-REFERENCE TO RELATED PATENT APPLICATIONS

This application is a continuation application of, and claims benefit of U.S. patent application Ser. No. 14/363,074, filed Jun. 5, 2014, now allowed, which itself is a U.S. national stage application of PCT application No. PCT/US2012/068771, filed Dec. 10, 2012, which itself claims priority to and the benefit of, pursuant to 35 U.S.C. § 119(e), U.S. provisional patent application Ser. No. 61/569,145, filed on Dec. 9, 2011, entitled "PERFUSION CONTROLLER, MICROCLINICAL ANALYZER AND APPLICATIONS OF THE SAME", by John P. Wikswo et al., U.S. provisional patent application Ser. No. 61/697,204, filed on Sep. 5, 2012, entitled "INTELLIGENT CHIP CARRIER AND CHIP CARRIER WITH MICROCHEMICAL ANALYZER AND APPLICATIONS OF THE SAME", by John P. Wikswo et al., and U.S. provisional patent application Ser. No. 61/717,441, filed on Oct. 23, 2012, entitled "INTEGRATED ORGAN MICROFLUIDICS (IOM) CHIP AND APPLICATIONS OF SAME", by John P. Wikswo et al. Each of the above-identified applications is incorporated herein in its entirety by reference.

Some references, which may include patents, patent applications, and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [3] represents the 3rd reference cited in the reference list, namely, Lima, E, Snider, R, Reiserer, R, Cliffel, D, Wikswo, J P. Multichamber Multipotentiostat System for Cellular Microphysiometry, Rev. Sci. Instrum., In preparation, 2011.

STATEMENT AS TO RIGHTS UNDER FEDERALLY-SPONSORED RESEARCH

This invention was made with government support under grant numbers NIH/NCI R21 CA126728-01A1, NIH/NIDA RC2DA028981-02, and NIH 1UH2-TR000491-01, awarded by the National Institutes of Health, DTRA grant HDTRA1-09-1-00-13, awarded by the Defense Threat Reduction Agency, and DARPA contract DARPA-11-73-MPSys-FP-11, awarded by the Defense Advanced Research Projects Agency, DOD/BCRP W81XWH-10-1-0157, awarded by Department of Defense Brest Cancer Research Program. The government has certain rights in the invention.

FIELD OF THE INVENTION

The present invention relates generally to a microfluidic system, and more particularly to perfusion controllers, microclinical analyzers, integrated bio-object microfluidics chips and systems utilizing the perfusion controllers and the microclinical analyzers and applications of the same.

BACKGROUND INFORMATION

Organs-on-chips are a promising means to test drug efficacy and interactions without the need for animal testing. However, there has been little thought into how multiple organ systems should be integrated to study multi-organ physiology. This invention addresses key issues in the measurement and control of multiple organ-on-chip systems.

The measurement systems, microfabricated devices, and analytical and modeling techniques developed over the past decade to instrument and control cancer, immune, yeast, and cardiac cells provide a unique opportunity to address some of the most fundamental issues in organ interactions and drug responses. This problem clearly requires a coordinated, interdisciplinary, high-technology approach, such as understanding the interaction between lung function and organ oxygenation, neuroimmune interactions, response to neural injury, cardiac arrhythmias, and development of new multimodal therapies. To date, there have been no demonstrations of methods for controlling and analyzing multiple organs-on-chips, particularly in a manner that allows a single design of controller and analyzer to be dynamically configured for a particular application or analysis.

Therefore, a heretofore unaddressed need exists in the art to address the aforementioned deficiencies and inadequacies.

SUMMARY OF THE INVENTION

In one aspect, the invention relates to a perfusion controller usable for maintenance and analysis associating with a plurality of bio-objects, where each bio-object includes an organ or a group of cells. In one embodiment, the perfusion controller has a plurality of inlets for providing a plurality of fluids, a plurality of outlets, and a fluidic network coupled between the plurality of inlets and the plurality of outlets and being in fluid communication with the plurality of bio-objects. The fluidic network comprises a plurality of fluidic switches and one or more on-chip pumps adapted for selectively and individually perfusing at least one of the plurality of bio-objects with at least one of the plurality of fluids at a predetermined perfusion flow rate and delivering an effluent of the at least one bio-object responsive to the perfusion to a predetermined one of the plurality of outlets, where the plurality of outlets is coupled to at least one of an analyzer, a waste port, one of the plurality of bio-objects, and the fluidic switch network.

In one embodiment, the desired fluids contain a dye, a drug, a medium or the like.

In one embodiment, the perfusion controller further includes a perfusion reservoir having a plurality of containers for containing the plurality of fluids, respectively, where the plurality of containers is coupled to the plurality of inlets for respectively providing the plurality of fluids.

In one embodiment, the perfusion controller may also have a microcontroller for individually controlling a flow rate of each fluidic path.

In one embodiment, the perfusion controller further includes one or more sensors at least coupled to the at least one bio-object for measuring a pressure drop across the at least one bio-object perfused with the at least one fluid, so as to regulate the flow rate of the at least one fluid through the at least one bio-object at the predetermined perfusion rate.

In one embodiment, the fluidic network further comprises a plurality of fluidic paths in fluid communication with the plurality of fluidic switches and the one or more on-chip pumps, where each bio-object is disposed in a corresponding fluidic path.

In one embodiment, each fluidic switch comprises a valve having at least one pole and a plurality of throws, where the at least one pole is selectively operable in fluid communication with one of the plurality of throws.

In one embodiment, the plurality of throws of the first fluidic switch of the fluidic switch network is respectively coupled to the plurality of inlets for respectively receiving the plurality of fluids therefrom. The plurality of throws of the last fluidic switch of the fluidic switch network is respectively coupled to the plurality of outlets for selectively delivering the effluent of the at least one bio-object responsive to the perfusion to the predetermined outlet.

In one embodiment, the fluidic network comprises first, second, and third fluidic switches and an on-chip pump, where the first fluidic switch comprises a one-pole and four-throw valve, the second fluidic switch comprises a two-pole and three-throw valve, and the third fluidic switch comprises a one-pole and four-throw valve. In one embodiment, the plurality of bio-objects includes organ N−1, organ N, and organ N+1, where the organ N−1 is coupled to the second fluidic switch, the organ N is coupled between the second fluidic switch and the on-chip pump that in turn is coupled to the third fluidic switches, and the organ N+1 is coupled to the second and third fluidic switches.

In one embodiment, the organs can be connected in parallel, where the fluidic pumps and switches provide the requisite capabilities for controlling the organs as stated above, but allow the organs to be connected in parallel.

In one embodiment, the selected organs can be connected in parallel while other organs can be connected in series, with the series combination being in parallel to other organs, e.g., a gastrointestinal organ being upstream from a liver organ, with the pair being in parallel with, for example, the kidney and other organs. In another example, the heart can be in series with the lung, or the lung can be fluidically between the right heart and the left heart. In each case, the fluidic pumps and switches provide the requisite capabilities for controlling the organs as stated above, but allow the organs to be connected in either series or parallel.

In one embodiment, each fluidic switch comprises a rotary planar valve (RPV) and each on-chip pump comprises a rotary planar peristaltic micropump (RPPM). Each of the RPV and the RPPM comprises an actuator/ball bearing having a circular ball-bearing cage defining a plurality of spaced-apart openings thereon, and a plurality of balls accommodated in the plurality of spaced-apart openings. In one embodiment, the number of the plurality of balls is same as that of plurality of spaced-apart openings of the circular ball-bearing cage, such that each opening of the circular ball-bearing cage accommodates a respective ball. In another embodiment, the number of the plurality of balls is less than that of plurality of spaced-apart openings of the circular ball-bearing cage, such that at least one opening accommodates no ball. In one embodiment, the plurality of spaced-apart openings is spaced-equally defined on the circular ball-bearing cage, where each two adjacent openings through the center of the circular ball-bearing cage define an angle $\theta = 2\pi/K$, K being the number of the plurality of equally spaced-apart openings. In the embodiments, the ball bearing comprises a cage and multiple balls trapped in the cage.

In another embodiment, the ball bearing has a cage and a single ball trapped in the cage.

In one embodiment, the actuator comprises a wheel defining a plurality of spaced-apart sockets thereon in a circle, and a plurality of rollers accommodated in the plurality of spaced-apart sockets such that a rotation of the wheel causes the plurality of rollers to rotate along the circle.

In another embodiment, the actuator comprises a cam, and a plurality of cam-followers engaged with the cam such that a rotation of the cam causes the plurality of cam-followers to rotate along a circular path.

In one embodiment, the RPV further comprises a plurality of selectively controllable channels positioned under the actuator in relation to the plurality of equally spaced-apart openings such that at least one selectively controllable channel is positioned under the at least one no-ball opening or no-ball location of the circular ball-bearing cage that does not contain a ball so that a fluid flow is allowed through the at least one selectively controllable channel, while the other selectively controllable channels are respectively positioned under the cage openings having the ball so that no fluid flows are allowed through the other selectively controllable channels, where when rotating the actuator by a desired angle of $(k \times \theta)$, k being 1, 2, . . . K, the at least one no-ball-bearing cage opening is selectively placed over a desired one of the selectively controllable channels. In another embodiment, the cage does not have an opening at the location where no ball is required.

In one embodiment, it would be possible to achieve these same functions with ball bearings were located at other-than-equal angular spacings.

In one embodiment, the plurality of selectively controllable channels comprises three selectively controllable channels connected in a T-like junction, and the actuator is configured such that when rotating by a desired angle of $(k \times \theta)$, two of the three channels are in fluid communication with each other, while the other channel is closed. In another embodiment, the plurality of selectively controllable channels comprises four selectively controllable channels connected to corners of a square fluidic path, and the actuator is configured such that when rotating by the desired angle of $(k \times \theta)$, the first and second channels are in fluid communication with each other through the top portion of the square fluidic path, and the third and fourth channels are in fluid communication with each other through the bottom portion of the square fluidic path, or the first and fourth channels are in fluid communication with each other through the left portion of the square fluidic path, and the second and third channels are in fluid communication with each other through the right portion of the square fluidic path.

In one embodiment, the RPV further comprises at least one always-open channel positioned under the actuator in offset from the plurality of equally spaced-apart openings, such that the at least one offset channel is in fluid communication with the at least one selectively controllable channel under the at least one no-ball bearing-cage opening, and the other selectively controllable channels under the openings having the ball bearings are closed.

In one embodiment, the ball bearings, i.e., balls and separate cages, in all these RPPM and RPV embodiments below are replaced by one or more integral ball-bearing cam followers arranged in a circle around the motor axis such that rotation of the motor will cause the ball-bearing cam followers to roll in a circle above a microfluidic channel, and thereby pump fluid peristaltically along that channel in an RPPM or occlude channels in an RPV.

In one embodiment, the caged balls in RPPMs that provide peristaltic pumping in all these embodiments are replaced by one or more rotary, cylindrical ball bearings whose axis is at a 45 degree or other angle with respect to axis by which the rotary ball bearing is driven in a circle, which in turn is perpendicular to the surface of the microfluidic device that contains the channels thorough with fluid is flowing.

In one embodiment, the caged balls that provide valve actuation in the RPVs in all these embodiments are replaced by the combination of a rotary actuator and a circular array of radial levers and springs such that the springs cause the channels beneath the levers to be compressed unless the rotary actuator is depressing the lever, thereby creating a set of normally closed valves that are opened by the rotary actuator. In this type of embodiment, the rotary actuator can either be one or more ball-bearing cam followers, or one of more angled cylindrical rotary ball bearings.

In one embodiment, each of the at least one always-open channel and the plurality of selectively controllable channels has an end connected to an arc fluidic path or a circular fluidic path. In another embodiment, the at least one always-open channel has first and second always-open channels positioned under the actuator in offset from the plurality of equally spaced-apart openings, where the plurality of selectively controllable channels comprise a first plurality of selectively controllable channels and a second plurality of selectively controllable channels, where the first always-open channel and the first plurality of selectively controllable channels are connected to a first arc fluidic path, and the second always-open channel and the second plurality of selectively controllable channels are connected to a second arc fluidic path, where the first and second arc fluidic paths are arranged in a circle and not in fluid communication with each other, such that in operation, the first always-open channel is selectively in fluid communication with one of the first plurality of selectively controllable channels, while the second always-open channel is selectively in fluid communication with one of the second plurality of selectively controllable channels.

In one embodiment, the RPPM further comprises an input channel and an output channel positioned under the actuator in relation to the plurality of equally spaced-apart openings such that when the actuator is rotated, a fluid is pumped from the input channel to the output channel.

In one embodiment, each of the RPVs and the RPPMs further comprises a motor for rotating the actuator incrementally by the angle θ. In one embodiment, the motor comprises a spring-loaded tensioning motor head or a self-tensioning motor head, where the self-tensioning motor head comprises a cylinder body, where the cylinder body has one or more helically cut slits around an axis of the cylinder body, or two or more horizontally cut slits alternatively in X and Y directions to allow tension to be applied in the direction of the axis of rotation of the RPPM or RPV.

In one embodiment, each of the one or more on-chip pumps comprises a pneumatically actuated peristaltic pump. In another embodiment, each of the one or more on-chip pumps comprises a mechanically actuated peristaltic pump.

Furthermore, the perfusion controller may have at least one bubble trap coupled to the fluidic network for removing bubbles therefrom.

In one embodiment, the at least one bubble trap comprises first and second microfluidic channels located at different levels defining a fluidic compartment therebetween, a vertical via for connecting the first and second microfluidic channels, a bubble withdrawal channel placed over the vertical via, and a hydrophobic gas exchange membrane placed between the via and the bubble withdrawal channel for separating the fluidic compartment from the bubble withdrawal channels. In one embodiment, an optional bubble accumulation area can be placed above the vertical via with the gas exchange membrane as the chamber's ceiling.

In another embodiment, the at least one bubble trap comprises a microfluidic channel containing a dense forest of micro-pillars within the fluidic path that act as bubble sieves catching passing bubbles while providing alternative parallel paths for fluid to move freely beneath them, and a bubble accumulation chamber formed directly over the micro-pillars. In one embodiment, a ceiling of the bubble accumulation chamber is formed of a hydrophobic gas exchange membrane that allows for bubble removal either due to passive diffusion into the atmosphere or due to actively applied gentle vacuum while preventing fluid escape.

In one embodiment, the plurality of bio-objects is connected to each other through the fluid bus in series, parallel, or a combination of them. In one embodiment, the at least one bio-object is operably bypassable from the other of the plurality of bio-objects.

In one embodiment, the perfusion controller is formed integrally with an optically transparent material.

In one aspect of the invention, a perfusion controller usable for analysis associating with a plurality of bio-objects, each bio-object including an organ or a group of cells includes a plurality of inlets for providing a plurality of fluids; a plurality of outlets; and a fluidic network coupled between the plurality of inlets and the plurality of outlets and being in fluid communication with the plurality of bio-objects. The fluidic network comprises a plurality of fluidic switches and one or more on-chip pumps. Each fluidic switch comprises a RPV and each on-chip pump comprises a RPPM. Each of the RPV and the RPPM comprises a rotary actuator. The rotary actuator of the RPPM operably pumps a fluid at a rate by actuating balls or rollers or cam-followers. The rotary actuator of the RPV operably rotates balls or rollers or cam-followers to selected positions to switch fluids in such a manner as to provide one or more bio-objects with selected fluids for maintaining bio-object health and for assaying bio-object metabolic and functional activity. One or more fluidic output channels are provided in the fluidic network for the purpose of waste disposal or collection of biological effluent samples, or connection to analytic equipment or connection to other bio-objects.

In another aspect, the invention relates to a system for analysis of a plurality of bio-objects. The system in one embodiment includes a network of perfusion controllers having a plurality of perfusion controllers as disclosed above. The plurality of perfusion controllers is arranged in an array for perfusing the plurality of bio-objects individually or simultaneously.

In one embodiment, the plurality of perfusion controllers is arranged in series, parallel, or a combination of them. In another embodiment, combinations of the plurality of bio-objects and the plurality of perfusion controllers are themselves arranged in series, parallel, or a combination of them to form the network of perfusion controllers.

In yet another aspect, the invention relates to a method for analyzing a plurality of bio-objects. The method includes the steps of providing a plurality of fluids, providing a fluidic network configured to be in fluid communication with the plurality of bio-objects and the plurality of fluids, where the fluidic network comprises a plurality of fluidic switches, one or more on-chip pumps, and a plurality of fluidic paths connected therebetween, and controlling the plurality of fluidic switches and the one or more on-chip pumps to selectively and individually perfuse at least one of the plurality of bio-objects with at least one of the plurality of fluids at a predetermined perfusion flow rate and deliver an effluent of the at least one bio-object responsive to the perfusion to a predetermined outlet destination for analysis, recirculation, waste exhaust, or input to other bio-objects of the plurality of bio-objects.

In one embodiment, the fluidic network further comprises a microclinical analyzer (also termed in some usages a microchemical analyzer).

In one embodiment, the method further comprises the step of calibrating the microclinical analyzer.

In one embodiment, the method also includes the step of detecting properties of the effluent of the at least one bio-object.

Additionally, the method further has the step of measuring a pressure drop across the at least one bio-object perfused with the at least one fluid, so as to regulate the flow rate of the at least one fluid through the at least one bio-object at the predetermined perfusion rate assuming the fluidic resistance of the bio-object is known or calculable.

Furthermore, the method may have the step of removing bubbles generated in the fluidic network.

In a further aspect, the invention relates to a microclinical analyzer usable for analysis of one or more bio-objects. In one embodiment, the microclinical analyzer comprises a fluidic network having a plurality of fluidic switches, a plurality of fluidic paths in fluid communication with the plurality of fluidic switches, and one or more on-chip pumps coupled to corresponding fluidic paths, a sensor array coupled to the fluidic network, and a perfusion controller coupled to the fluidic network and adapted for perfusing a bio-object with a desired fluid and outputting an effluent of the bio-object responsive to the perfusion, where the fluidic network is configured such that the effluent of the bio-object is operably and selectively deliverable to the sensor array for detecting properties of the effluent, to a predetermined outlet of the fluidic network, or to one of the plurality of bio-objects.

In one embodiment, each fluidic switch comprises a valve having at least one pole and a plurality of throws, where the at least one pole is operably and selectively in fluid communication with one of the plurality of throws.

In one embodiment, the microclinical analyzer further includes a calibration reservoir having a plurality of containers for containing a plurality of fluids, respectively, where the plurality of containers is coupled to the plurality of throws of one of the plurality of fluidic switches for individually providing the plurality of fluids to the sensor array for calibration. This calibration could be performed at repeated intervals selected to track the biological activity of the bio-object. After each calibration operation, the sensor could be maintained passively in one of the calibration solutions to maintain sensor performance in the interval between measurements of biological activity and calibrations.

In one embodiment, the plurality of fluidic switches comprises first, second, and third fluidic switches, where the first fluidic switch comprises a one-pole and four-throw valve coupled to the calibration reservoir, the second fluidic switch comprises a four-pole and three-throw valve coupled to the first fluidic switch, the sensor array, and the perfusion controller, and the third fluidic switch comprises a one-pole and four-throw valve coupled to the on-chip pump and outlets and another bio-object, where the second and third fluidic switches are coupled to each other through the on-chip pump.

In one embodiment, each fluidic switch comprises a RPV and each on-chip pump comprises a RPPM, where each of the RPV and the RPPM comprises an actuator having a circular ball-bearing cage defining a plurality of equally spaced-apart openings thereon, and a plurality of balls accommodated in the plurality of equally spaced-apart openings such that at least one opening accommodates no ball, where each two adjacent openings through the center of the circular ball-bearing cage define an angle $\theta=2\pi/K$, K being the number of the plurality of equally spaced-apart openings.

In one embodiment, the RPV further comprises a plurality of selectively controllable channels positioned under the actuator in relation to the plurality of equally spaced-apart openings such that at least one selectively controllable channel is positioned under the at least one no-ball opening or under at least one no-ball location of the circular ball-bearing cage so that a fluid flow is allowed through the at least one selectively controllable channel, while the other selectively controllable channels are respectively positioned under the openings having the ball bearings so that no fluid flows are allowed through the other selectively controllable channels, where when rotating the actuator by a desired angle of $(k \times \theta)$, k being 1, 2, . . . K, the at least one cage opening without a ball or the absence of a cage opening is selectively placed over a desired one of the selectively controllable channels.

In one embodiment, the RPPM further comprises an input channel and an output channel positioned under the actuator in relation to the plurality of equally spaced-apart openings such that when the actuator is rotated, a fluid flow is pumped from the input channel to the output channel.

In one embodiment, each of the RPV and the RPPM further comprises a motor for rotating the actuator incrementally by the angle $\theta$. In one embodiment, the motor comprises a spring-loaded tensioning motor head or a self-tensioning motor head.

In yet a further aspect, the invention relates to an integrated bio-object microfluidics chip. In one embodiment, the integrated bio-object microfluidics chip comprises a fluid network. The fluid network comprises a plurality of inlets for providing a plurality of fluids, a plurality of outlets, a bio-object chamber for accommodating at least one bio-object, first and second fluidic switches, and a first pump. The bio-object chamber, the first and second fluidic switches, and the first pump are coupled to each other in series. The first fluidic switch is further coupled to the plurality of inlets for selectively receiving one of the plurality of fluids therefrom and routing the received fluid to the first pump that in turn pumps the received fluid to the bio-object chamber so as to perfuse the at least one bio-object therein. The second fluidic switch is further coupled to the plurality of outlets for selectively delivering an effluent of the at least one bio-object responsive to the perfusion to a predetermined outlet, or to the first fluidic switch for recirculation.

In one embodiment, the integrated bio-object microfluidics chip further includes a bio-object loading port coupled to the bio-object chamber for loading the at least one bio-object.

In one embodiment, each fluidic switch comprises a valve having at least one pole and a plurality of throws, where the at least one pole is selectively operable in fluid communication with one of the plurality of throws.

In one embodiment, each fluidic switch comprises a RPV and the first pump comprises a RPPM, where each RPV and RPPM comprises an actuator having a circular ball-bearing cage defining a plurality of equally spaced-apart openings thereon, and a plurality of balls accommodated in the plurality of equally spaced-apart openings such that at least one opening accommodates no ball bearing, where each of the two adjacent openings through the center of the circular ball-bearing cage define an angle $\theta=2\pi/K$, K being the number of the plurality of equally spaced-apart openings.

In addition, the RPV further comprises a plurality of selectively controllable channels positioned under the actuator in relation to the plurality of equally spaced-apart openings such that at least one selectively controllable channel is positioned under the ball bearing, and at least one no-ball-bearing channel is open such that a fluid flow is allowed through the at least one selectively controllable channel, while the other selectively controllable channels are respectively closed so that no fluid flows are allowed through the other selectively controllable channels. As such, when rotating the actuator by a desired angle of $(k\times\theta)$, k being 1, 2, ... K, the at least one no-ball opening or no-ball location in the bearing cage is selectively placed over a desired selectively controllable channels.

In one embodiment, the RPV also comprises at least one always-open channel positioned under the actuator in offset from the plurality of equally spaced-apart openings, such that the at least one offset channel is in fluid communication with the at least one selectively controllable channel under the at least one no-ball opening or under at least one no-ball location in the bearing cage, and the other selectively controllable channels under the openings having the balls in the bearing cage are closed.

In one embodiment, each of the at least one always-open channel and the plurality of selectively controllable channels has an end connected to an arc fluidic path or a circular fluidic path.

In one embodiment, the at least one always-open channel has first and second always-open channels positioned under the actuator in offset from the plurality of equally spaced-apart openings, where the plurality of selectively controllable channels comprise a first plurality of selectively controllable channels and a second plurality of selectively controllable channels, where the first always-open channel and the first plurality of selectively controllable channels are connected to a first arc fluidic path, and the second always-open channel and the second plurality of selectively controllable channels are connected to a second arc fluidic path, where the first and second arc fluidic paths are arranged in a circle and not in fluid communication with each other, such that in operation, the first always-open channel is selectively in fluid communication with one of the first plurality of selectively controllable channels, while the second always-open channel is selectively in fluid communication with one of the second plurality of selectively controllable channels.

In one embodiment, the RPPM further comprises an input channel and an output channel positioned under the actuator in relation to the plurality of equally spaced-apart openings such that when the actuator is rotated, a fluid flow is pumped from the input channel directly to the output channel for the purposes of continuously transporting fluid across the device.

In one embodiment, each of the RPV and the RPPM further comprises a motor for rotating the actuator incrementally by the angle θ, where the motor comprises a spring-loaded tensioning motor head or a self-tensioning motor head.

In one embodiment the integrated bio-object microfluidics chip also comprises at least one bubble trap coupled to the fluidic network for removing bubbles therefrom.

In one embodiment, the fluidic network further comprises a plurality of calibration solution ports for providing a plurality of calibration solutions for calibration, a third fluidic switch coupled to the plurality of calibration solution ports where the third fluidic switch is further coupled between the bio-object chamber and the second fluidic switch, a second pump coupled to the third fluidic switch, and a microclinical analyzer coupled between the second pump and the second fluidic switch.

In one embodiment, the integrated bio-object microfluidics chip further includes a chip carrier in which the fluidic network is formed.

Additionally, the integrated bio-object microfluidics chip also has a microcontroller for controlling operations of the first and second fluidic switches and the first pump. In one embodiment, the microcontroller is provided with at least one of a wireless communication protocol and a backup battery.

In one aspect, the invention relates to an integrated bio-object microfluidics chip. In one embodiment, the integrated bio-object microfluidics chip comprises first and second fluid networks. Each fluid network comprises a plurality of inlets for providing a plurality of fluids, a plurality of outlets, a bio-object chamber for accommodating at least one bio-object, first and second fluidic switches, and a first pump. The bio-object chamber, the first and second fluidic switches, and the first pump are coupled to each other in series. The first fluidic switch is further coupled to the plurality of inlets for selectively receiving one of the plurality of fluids therefrom and routing the received fluid to the first pump that in turn pumps the received fluid to the bio-object chamber so as to perfuse the at least one bio-object therein. The second fluidic switch is further coupled to the plurality of outlets for selectively delivering an effluent of the at least one bio-object responsive to the perfusion to a predetermined outlet, or to the first fluidic switch for recirculation. The bio-object chambers of the first and second fluidic networks are substantially proximal to each other while separated by a thin barrier or a membrane that allows for signaling between the bio-object chambers of the first and second fluidic networks.

In one embodiment, each of the first and second fluidic switches comprises a RPV and the first pump comprises a RPPM.

In another aspect, the invention relates to an integrated bio-object microfluidics chip. In one embodiment, the integrated bio-object microfluidics chip has a fluidic network comprising a plurality of inlets for providing a plurality of fluids, a plurality of outlets, a bio-object chamber for accommodating at least one bio-object, a plurality of fluidic switches, and one or more pumps, where the bio-object chamber, the plurality of fluidic switches, and the one or more pumps are coupled to each other such that at least one fluidic switch operably and selectively receives one fluid from a corresponding inlet and routes the received fluid, through the one or more pumps, to the bio-object chamber so as to perfuse the at least one bio-object therein, and one of the other fluidic switches operably and selectively delivers an effluent of the at least one bio-object responsive to the perfusion to a predetermined outlet, or to the at least one fluidic switch for recirculation.

In one embodiment, each fluidic switch comprises a RPV and each pump comprises a RPPM.

In one embodiment, the integrated bio-object microfluidics chip further includes a chip carrier in which the fluidic network is formed.

Further, the integrated bio-object microfluidics chip has a microcontroller for controlling operations of the plurality of fluidic switches and the one or more pumps. In one embodiment, the microcontroller is provided with a wireless communication protocol and a backup battery.

In yet another aspect, the invention relates to an integrated bio-object microfluidics chip cartridge. In one embodiment, the integrated bio-object microfluidics chip cartridge has a chip carrier, and at least one integrated bio-object microfluidics chip including at least one fluidic network formed in the chip carrier. The at least one fluidic network comprises a plurality of inlets for providing a plurality of fluids, a plurality of outlets, a bio-object chamber for accommodating at least one bio-object, a plurality of fluidic switches, and one or more pumps. The bio-object chamber, the plurality of fluidic switches, and the one or more pumps are coupled to each other such that at least one fluidic switch operably and selectively receives one fluid from a corresponding inlet and routes the received fluid, through the one or more pumps, to the bio-object chamber so as to perfuse the at least one bio-object therein, and one of the other fluidic switches operably and selectively delivers an effluent of the at least one bio-object responsive to the perfusion to a predetermined outlet, or to the at least one fluidic switch for recirculation.

In one embodiment, the integrated bio-object microfluidics chip cartridge further comprises a reservoir coupled to the plurality of inlets for providing the plurality of fluids.

Additionally, the integrated bio-object microfluidics chip cartridge also comprises a microclinical analyzer coupled to the fluidic network for detecting properties of effluent of the at least one bio-object.

Further, the integrated bio-object microfluidics chip cartridge has a calibration solution reservoir coupled to the microclinical analyzer for calibration thereof.

Moreover, the integrated bio-object microfluidics chip cartridge may further comprise a microcontroller for controlling operations of the plurality of fluidic switches and the one or more pumps of the fluidic network and the microclinical analyzer, where the microcontroller is provided with at least one of a wireless communication protocol and a backup battery.

In a further aspect, the invention relates to an integrated bio-object microfluidics chip cartridge. In one embodiment, the integrated bio-object microfluidics chip cartridge has at least one inlet for individually providing a plurality of fluids, at least one outlet, at least one bio-object chamber coupled between the at least one inlet and the at least one outlet, for accommodating at least one bio-object, at least one perfusion control unit coupled to at least one bio-object chamber for selectively perfusing the at least one bio-object with one of the plurality of fluids, at least one microclinical analyzer coupled to the at least one perfusion control module for analyzing an effluent of the at least one bio-object responsive to the perfusion, a microcontroller coupled to the at least one perfusion control module and the at least one microclinical analyzer, and a chip carrier for accommodating the at least one bio-object chamber, the at least one perfusion control unit, at least one microclinical analyzer and the microcontroller.

In one embodiment, the microcontroller is provided with at least one of a wireless communication protocol and a backup battery.

In one embodiment, the carrier comprises a plurality of fluidic paths formed therein for connecting the at least one inlet, the at least one outlet, the at least one bio-object chamber, the at least one perfusion control unit, and at least one microclinical analyzer.

In one embodiment, the at least one perfusion control unit comprises at least one fluidic network having a plurality of fluidic switches, and one or more pumps, configured such that at least one fluidic switch operably and selectively receives one fluid from a corresponding inlet and routes the received fluid, through the one or more pumps, to the bio-object chamber so as to perfuse the at least one bio-object therein, and one of the other fluidic switches operably and selectively delivers an effluent of the at least one bio-object responsive to the perfusion to a predetermined outlet destination, or to the at least one fluidic switch for recirculation.

In one embodiment, the integrated bio-object microfluidics chip cartridge includes a mechanical controller for sensing strain and applying either pneumatic or mechanical stresses to the at least one bio-object chamber.

Further, the integrated bio-object microfluidics chip cartridge includes a microscope or other means of optical imaging coupled to the at least one bio-object chamber.

Additionally, the integrated bio-object microfluidics chip cartridge also has a support system having at least one of a fluid unit coupled to the at least one bio-object chamber and the at least one perfusion control unit for providing the perfusion fluids, a gas supply unit coupled to the at least one perfusion control unit, and a waste unit coupled to the at least one perfusion control unit for exhausting the effluent of the at least one bio-object.

Moreover, the integrated bio-object microfluidics chip cartridge includes a sample collection unit coupled to the at least one perfusion control unit.

In one embodiment, the integrated bio-object microfluidics chip cartridge further has an environment control unit designed to provide an appropriate physiological environment to at least one bio-object.

In another embodiment, the integrated bio-object microfluidics chip cartridge also has at least two individual flow channels that connect with the at least one perfusion control unit, where one of the at least two individual flow channels is adapted for an efferent flow, while the other of the at least two individual flow channels is adapted for an afferent flow.

In yet a further aspect, the invention relates to a system for analysis of a plurality of bio-objects. The system in one embodiment includes a plurality of integrated bio-object microfluidics chip cartridges as claimed above. The plurality of integrated bio-object microfluidics chip cartridges is arranged in an array for analysis of the plurality of bio-objects individually or simultaneously.

In one embodiment, the plurality of integrated bio-object microfluidics chip cartridges is arranged in series, parallel, or a combination of them.

Also, the system may further include a system controller for controlling the plurality of integrated bio-object microfluidics chip cartridges so as to selectively analyze one or more of the plurality of bio-objects individually or simultaneously.

In one aspect, the invention relates to a system for analysis of a plurality of bio-objects. In one embodiment, the system has at least one perfusion controller, at least one microclinical analyzer, and a controller in communication with the at least one perfusion controller and the at least one microclinical analyzer for controlling operations of the at least one perfusion controller and the at least one microclinical analyzer as to selectively analyze one or more of the plurality of bio-objects individually or simultaneously.

In addition, the at least one perfusion controller comprises at least one fluidic network having a plurality of fluidic switches, one or more pumps, and a bio-object chamber, configured such that at least one fluidic switch operably and selectively receives one fluid and routes the received fluid, through the one or more pumps, to the bio-object chamber so as to perfuse at least one bio-object therein, and one of the other fluidic switches operably and selectively delivers an effluent of the at least one bio-object responsive to the perfusion to a predetermined outlet destination, or to the at least one fluidic switch for recirculation.

In another aspect, the invention relates to a rotary caster actuator usable for an RPV and an RPPM. In one embodiment, the rotary caster actuator has a shaft; and a ball or roller bearing assembly angularly mounted onto the shaft, wherein the ball or roller bearing assembly has an outer rim configured such that when the shaft rotates, the outer rim of the ball or roller bearing assembly rolls along a circular path.

In one embodiment, the ball or roller bearing assembly comprises a socket ball bearing cage angularly mounted onto the shaft.

In another embodiment, the ball or roller bearing assembly further comprises a pressure transfer bearing; a pressure holding plate held in place for transferring tensioning pressure via the pressure transfer bearing to microfluidic channels thereunder.

In yet another embodiment, the ball or roller bearing assembly further comprises a rotary encoder for proving feedback indication of the bearing position, and an interface collar for providing the attachment of the shaft to a motor.

In yet another aspect, the invention relates to a device usable for an RPV and an RPPM. In one embodiment, the device comprises a spring loaded pressure inverter assembly utilized to convert the downward pressure exerted by a ball or roller bearing rotary actuator assembly into an upward force capable of opening a normally closed microfluidic channel.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

In one embodiment, the pump is a pneumatically actuated peristaltic pump, or a peristaltic pump with multiple, independent mechanical actuators. Accordingly, application of no pressure leaves the pump in the normally open mode, thereby allowing free flow through the channels. In one embodiment, rotary planar peristaltic micropumps are used, and if it is desired to run the organ with flow driven solely by other organs or off-chip pumps, then it is necessary to add a mechanical retractor to the drive balls, or insert a unidirectional flapper bypass valve or a selector bypass valve across the pump.

Figure 9:
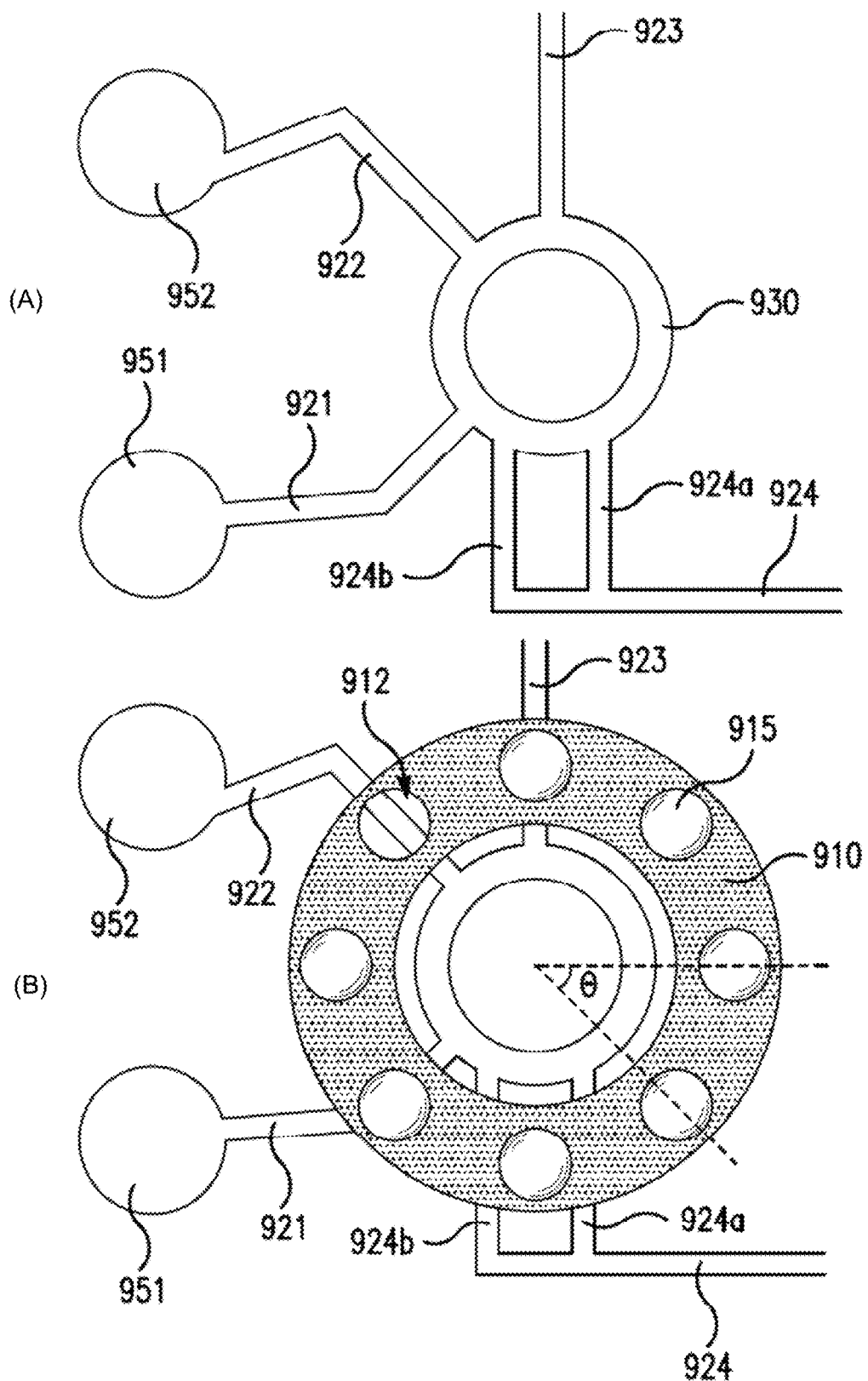

FIG. 9 shows schematically a valve design according to one embodiment of the invention, (A) a schematic layout of channels, and (B) a schematic of the valve assembly.

Figure 10:
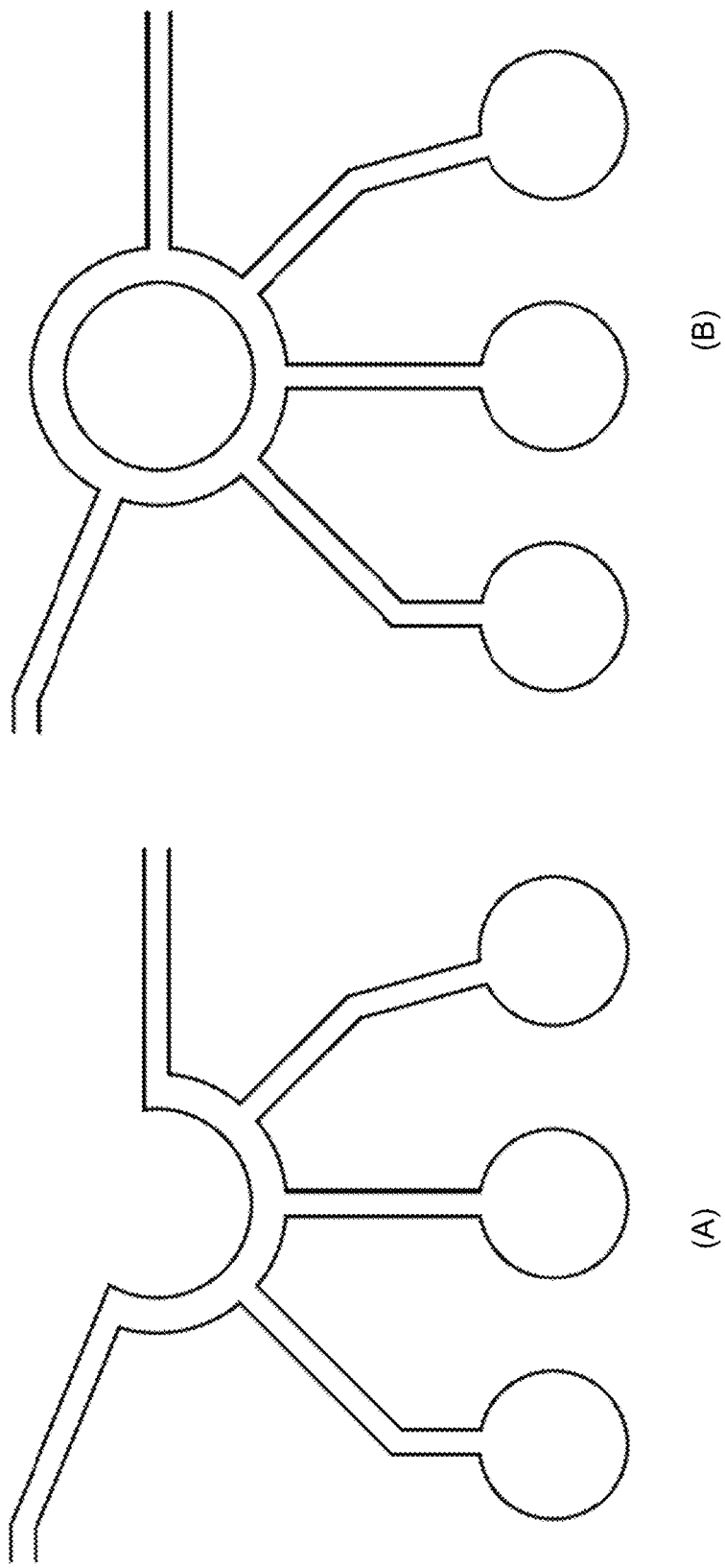

FIG. 10 shows schematically two channel layouts (A) and (B) of a valve design according to two embodiments of the invention, with the arc removed in (A) to lower fluid dead volume.

Figure 11:
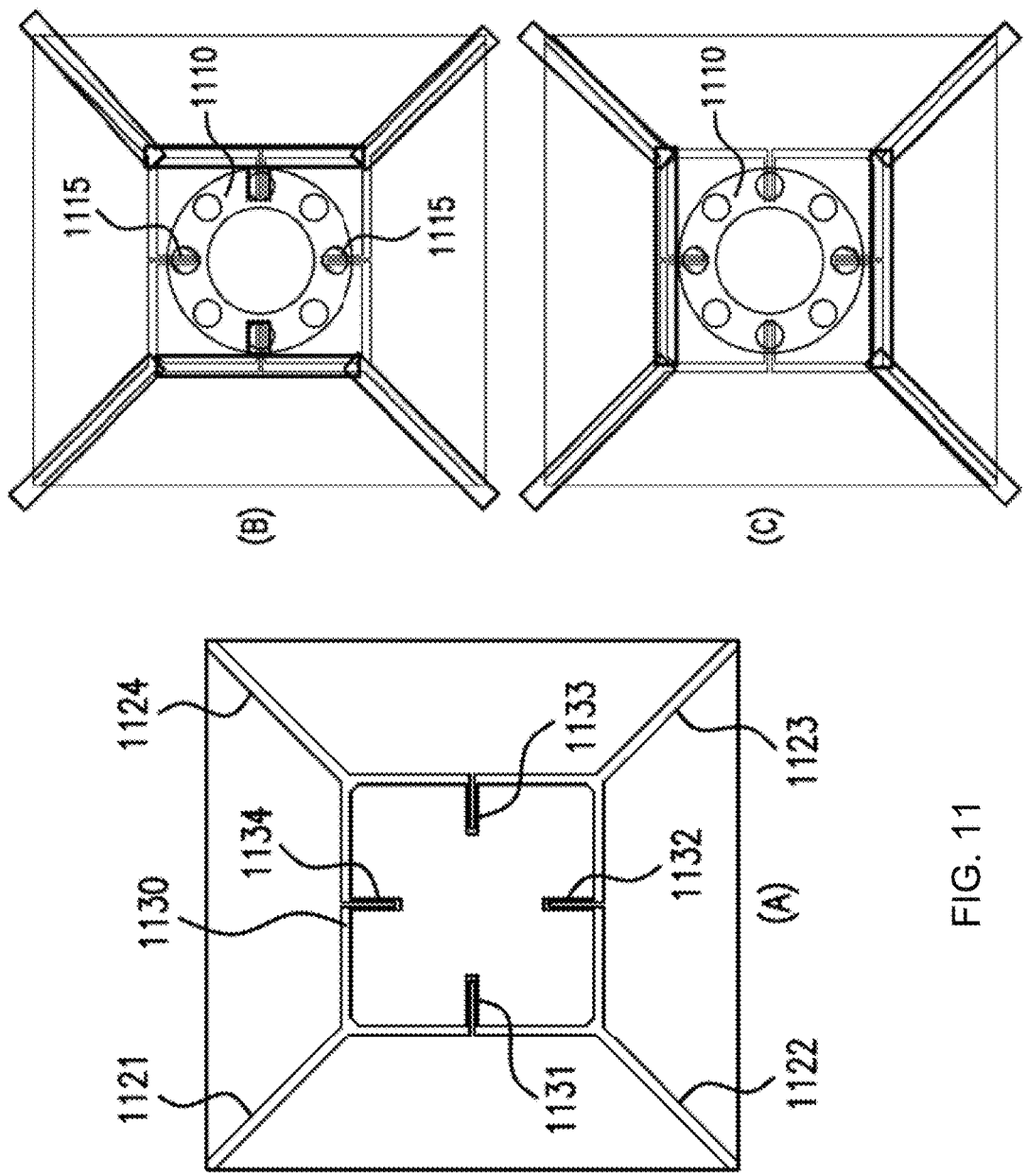

FIG. 11 shows schematically a four-way double-pole double-throw valve with positions illustrated in (B) and (C) according to one embodiment of the invention, (A) a schematic layout of channels.

Figure 12:
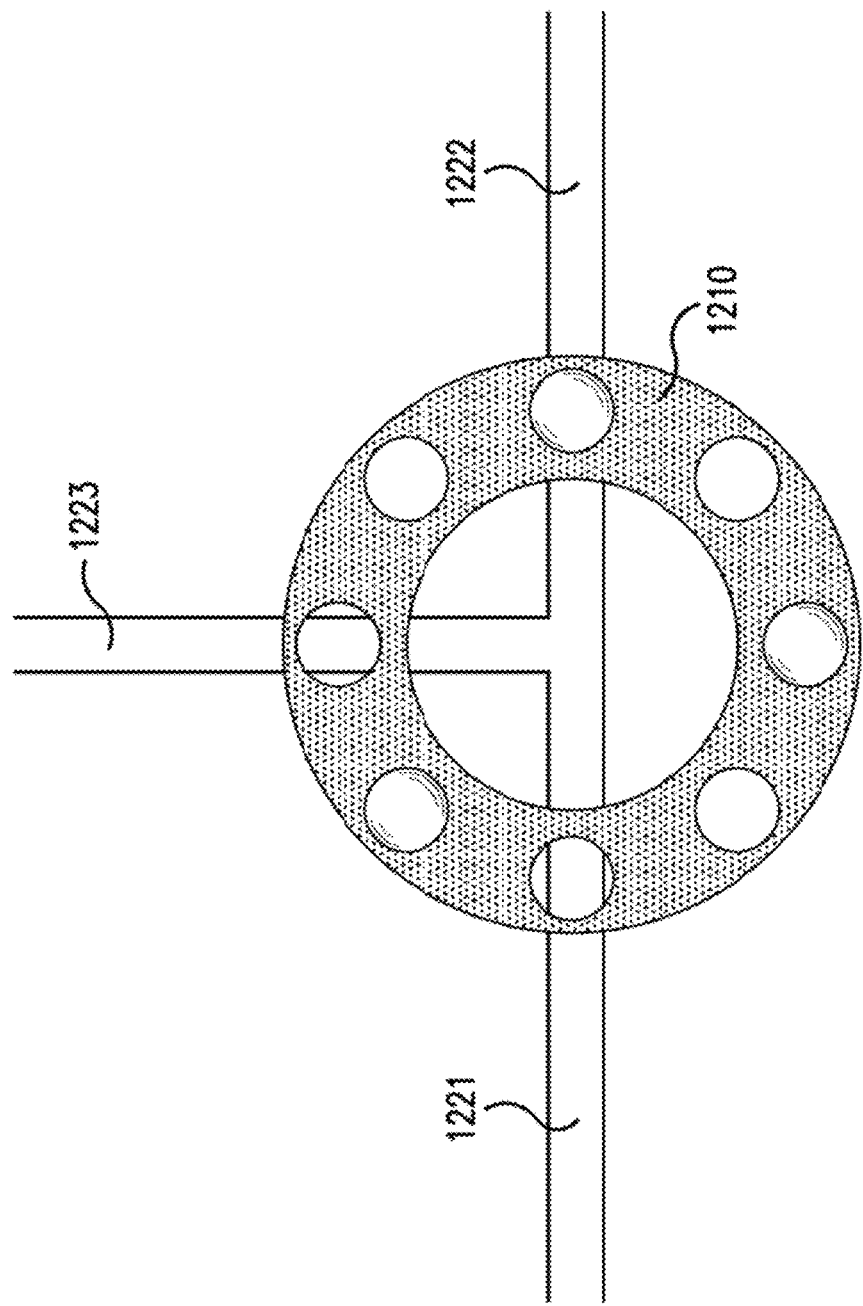

FIG. 12 shows schematically a right, left, or through T-valve configuration according to one embodiment of the invention.

Figure 13:
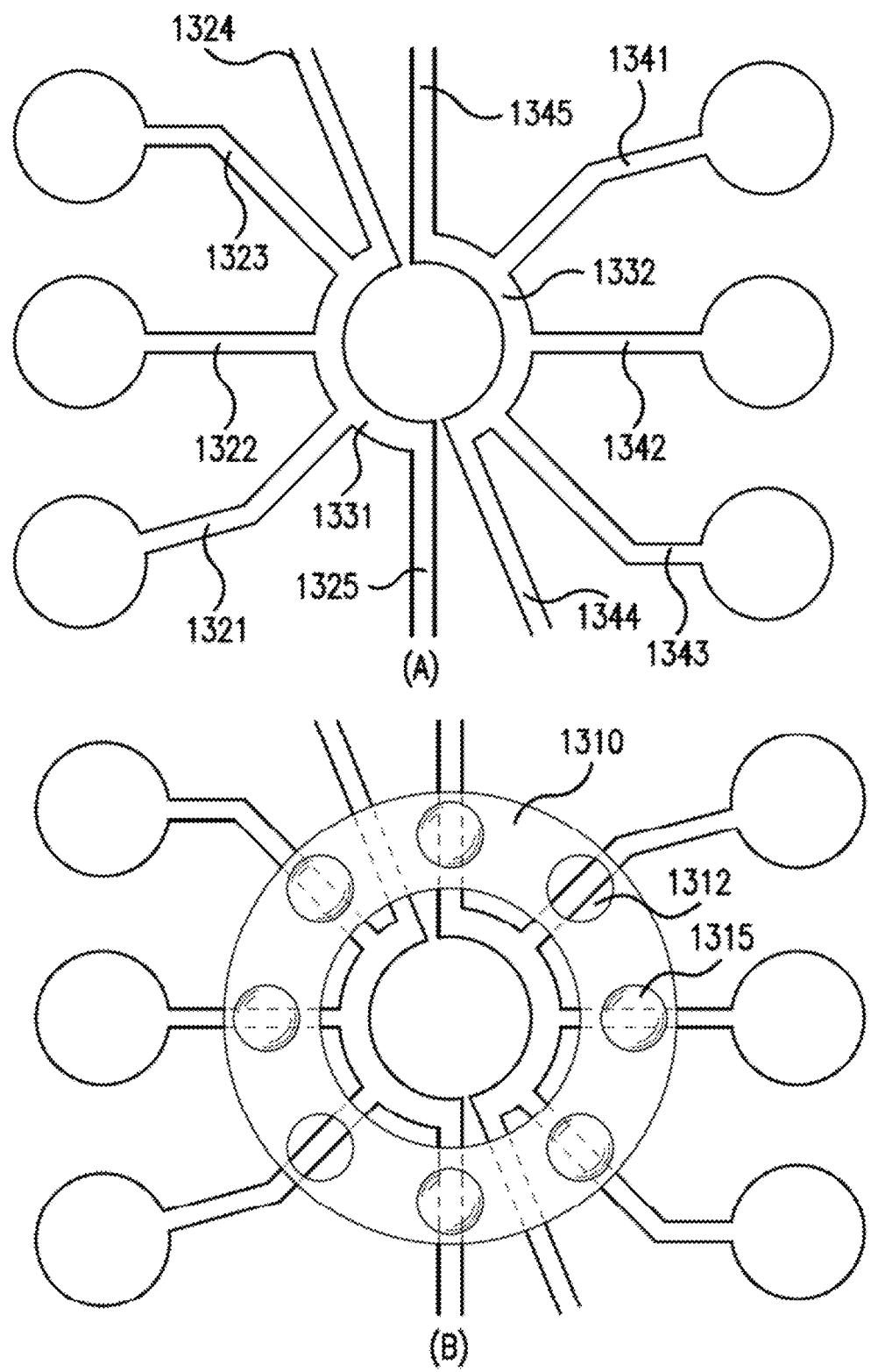

FIG. 13 shows schematically a double valve operated with a single ball cage (B) according to one embodiment of the invention, (A) a schematic layout of channels.

Figure 14:
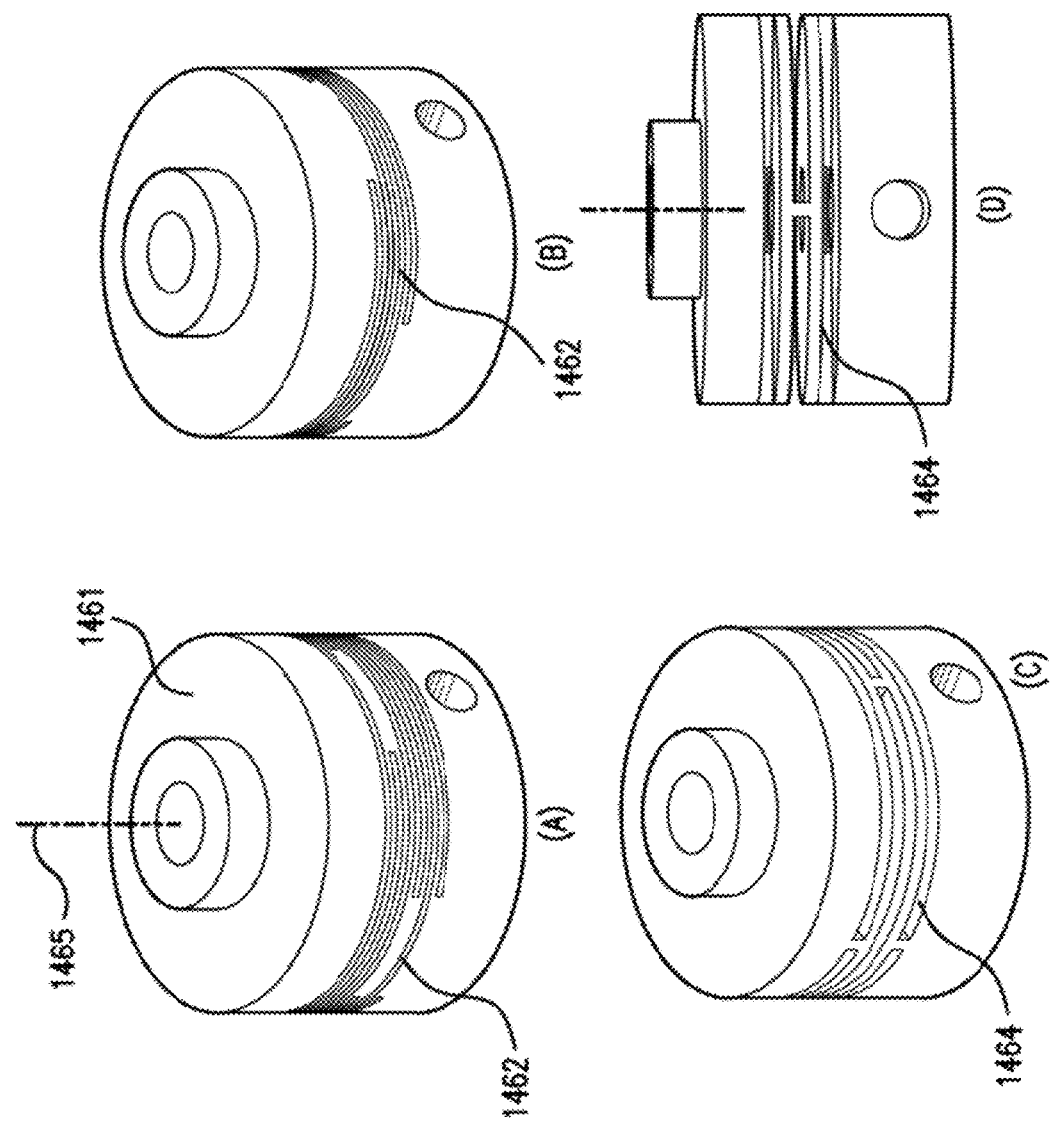

FIG. 14 shows a self-tensioning motor head for supplying constant force to the IOM Chip according to four embodiments (A)-(D) of the invention.

Figure 15:
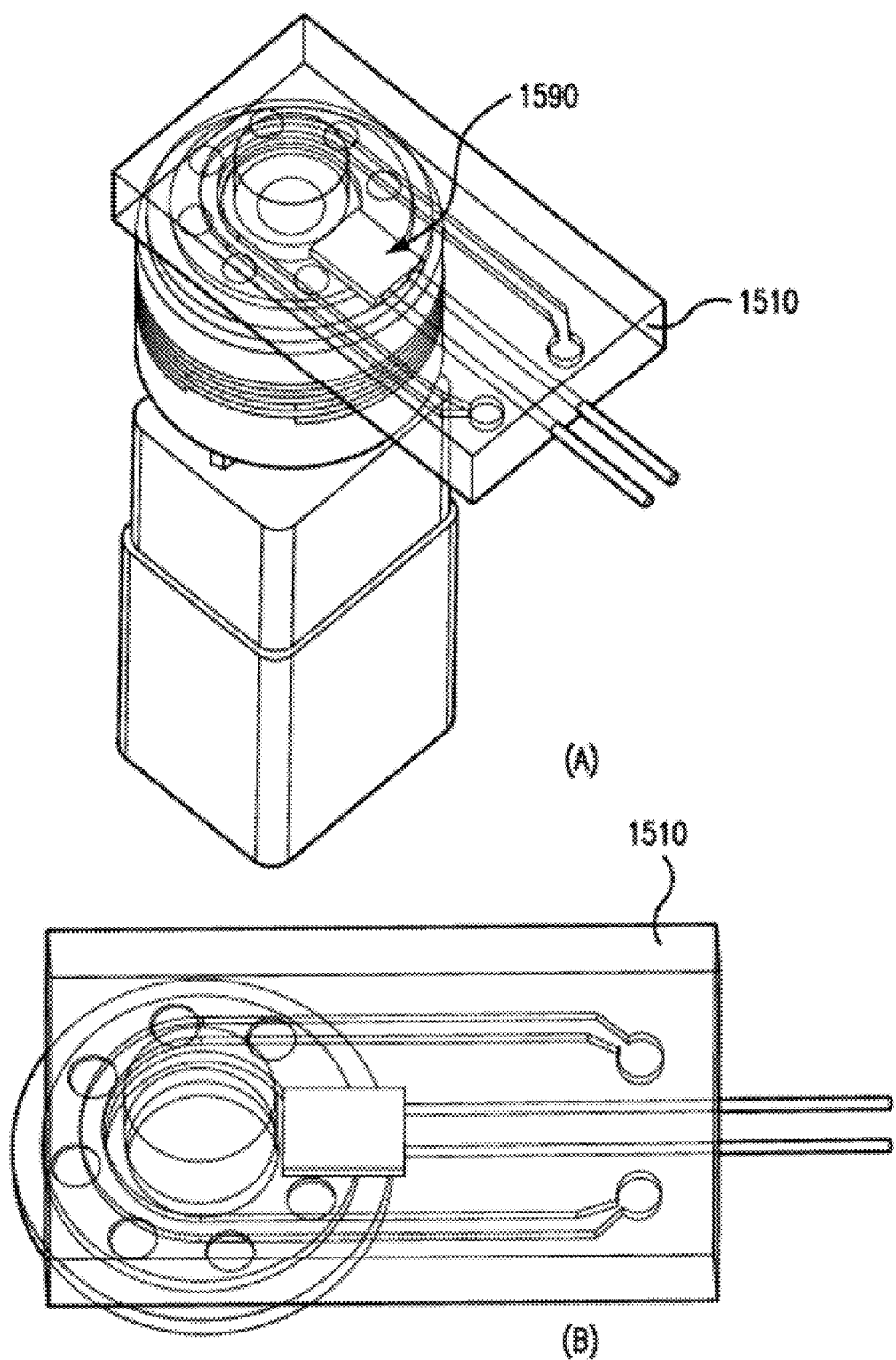

FIG. 15 shows schematically two views (A) and (B) of a RPPM having an embedded strain gauge in PDMS for observing the positions of the ball bearings according to one embodiment of the invention.

Figure 16:
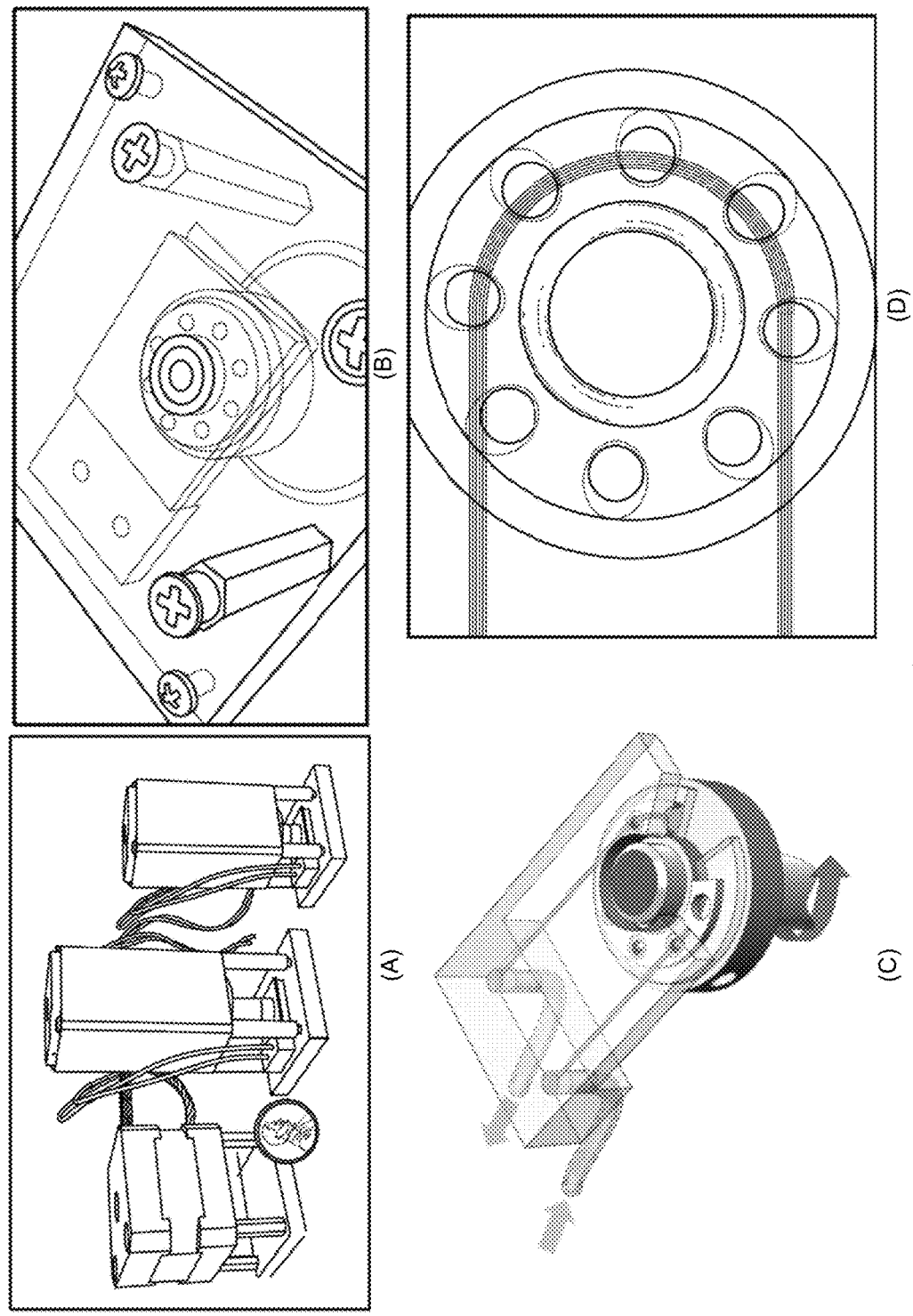

FIG. 16 shows various implementations (A)-(D) of a rotary planar peristaltic micropump according to embodiments of the invention.

Figure 17:
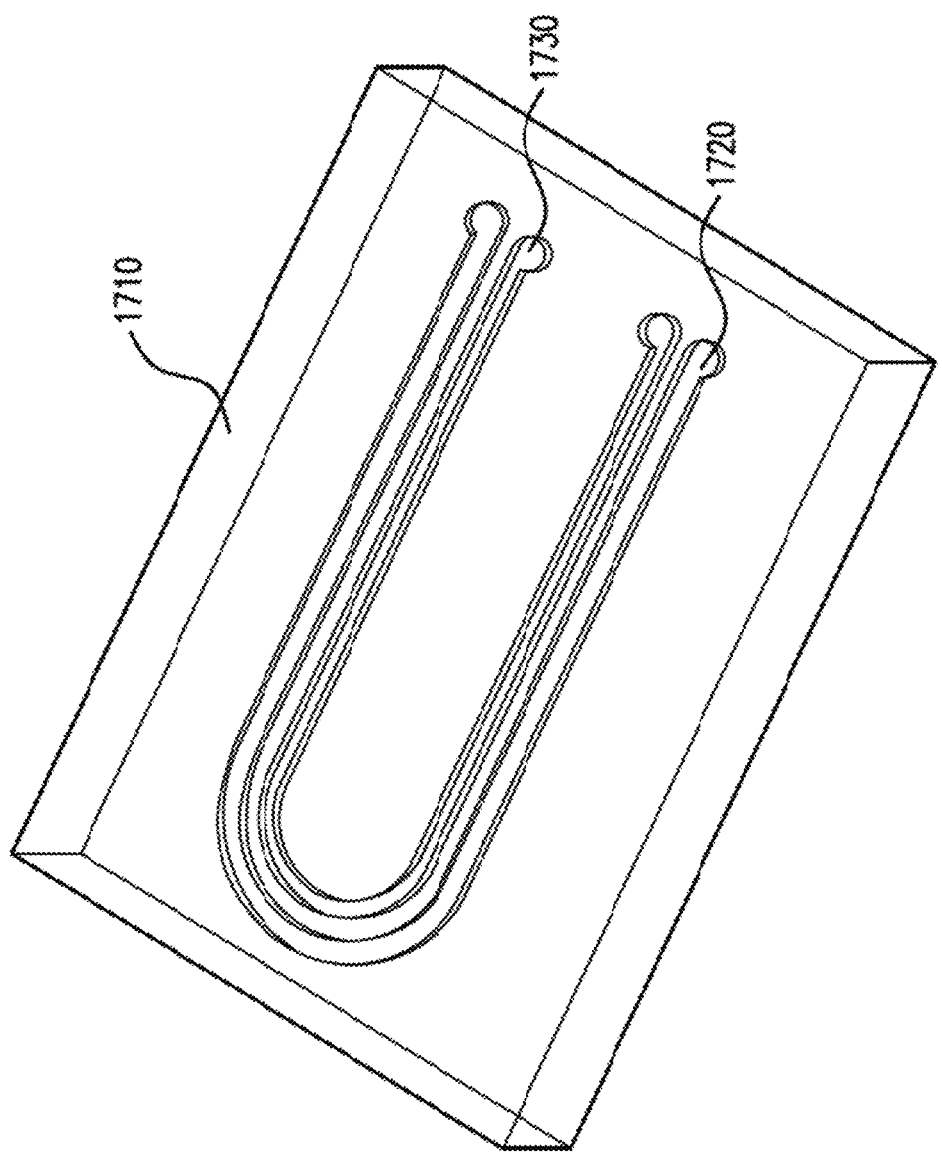

FIG. 17 shows schematically a double channel pumphead according to one embodiment of the invention.

Figure 18:
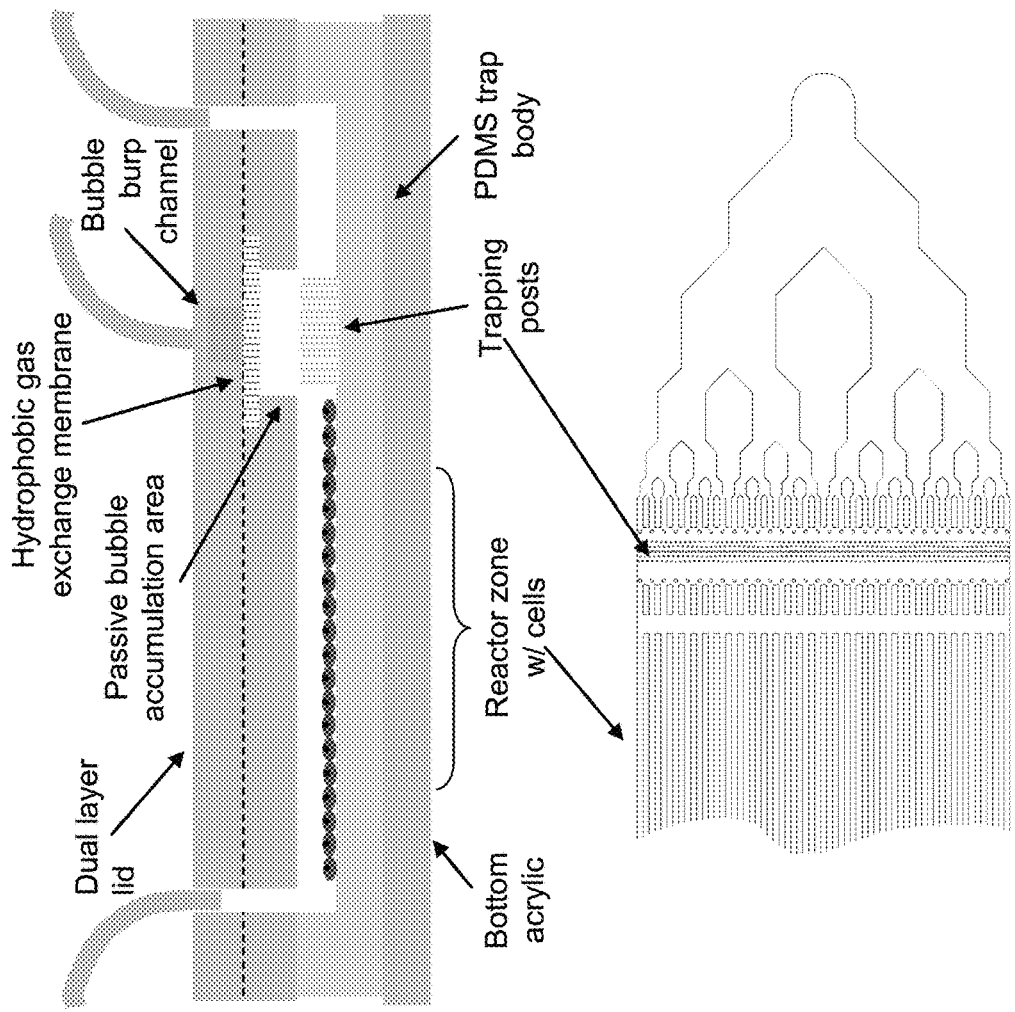

FIG. 18 shows schematically a parallel capillary vascular bioreactor with built-in in-line bubble trap according to one embodiment of the invention.

Figure 19:
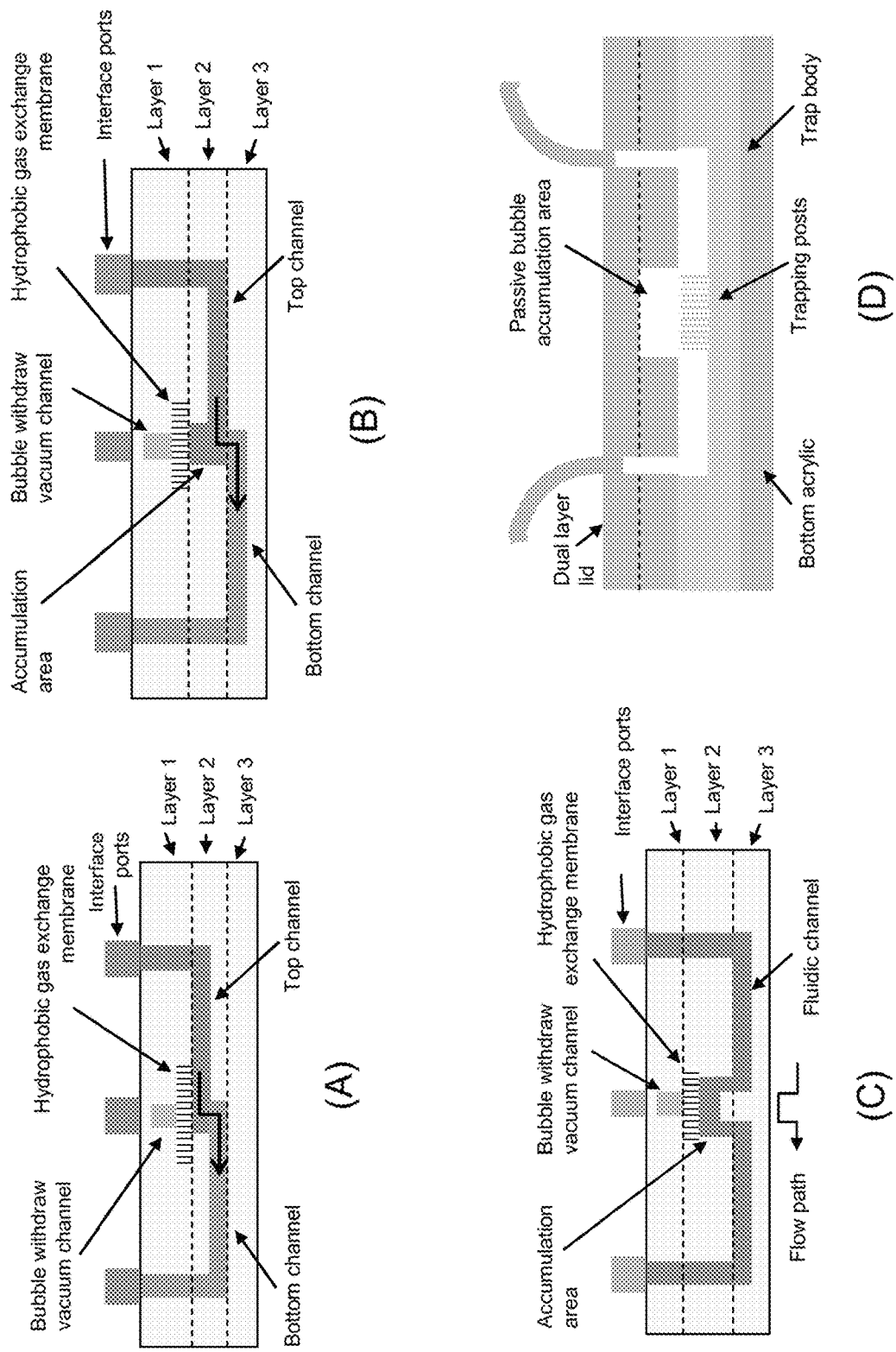

FIG. 19 shows schematically four stand-alone microfluidic bubble traps (A), (B), and (C) utilizing straight channels and (D) with pillars and bubble accumulation chambers according to one embodiment of the invention.

FIG. 20 shows a bubble trap implementation of a microfluidic bubble trap with straight channels according to one embodiment of the invention.

Figure 21:
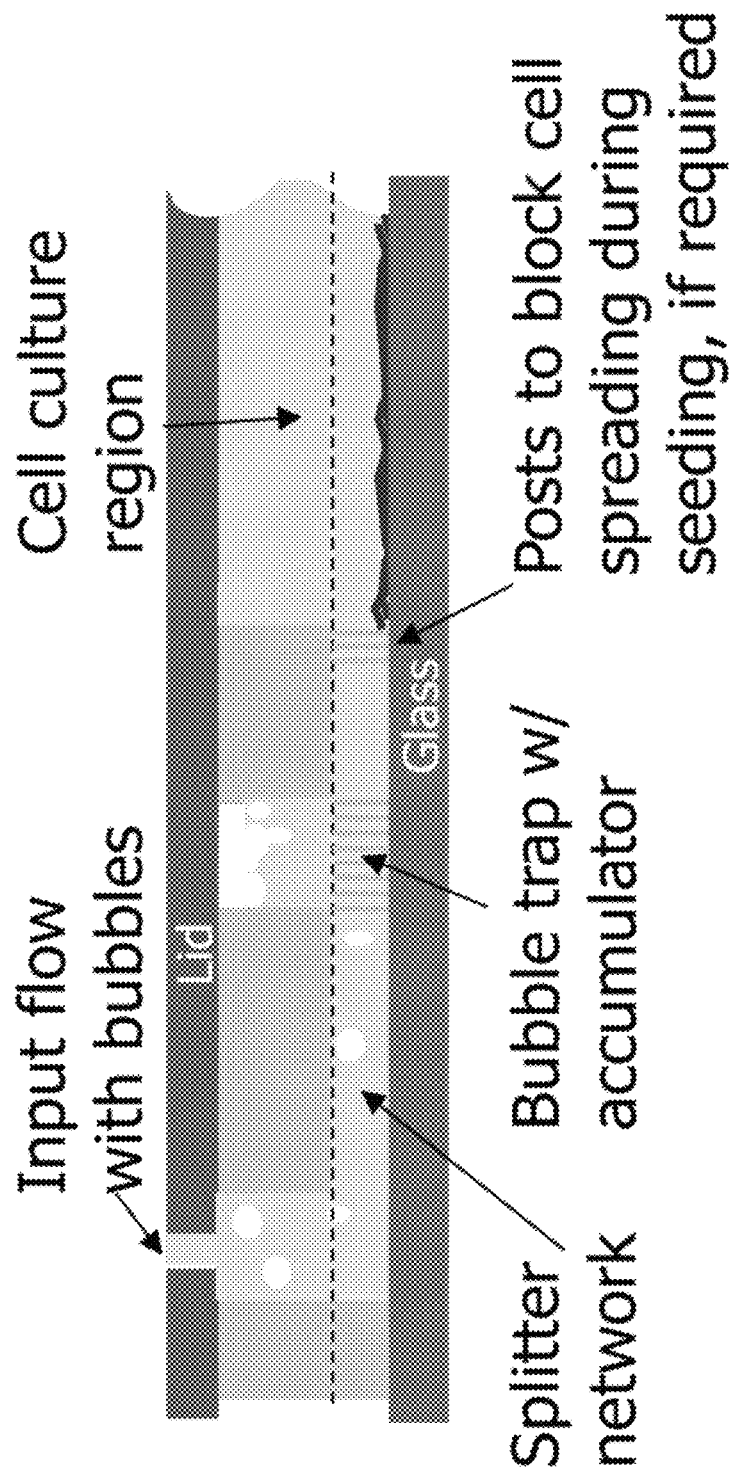

FIG. 21 shows schematically a bubble trap for incorporation into a perfusion controller, a microclinical analyzer, or an organ chip, according to one embodiment of the invention.

Figure 22:
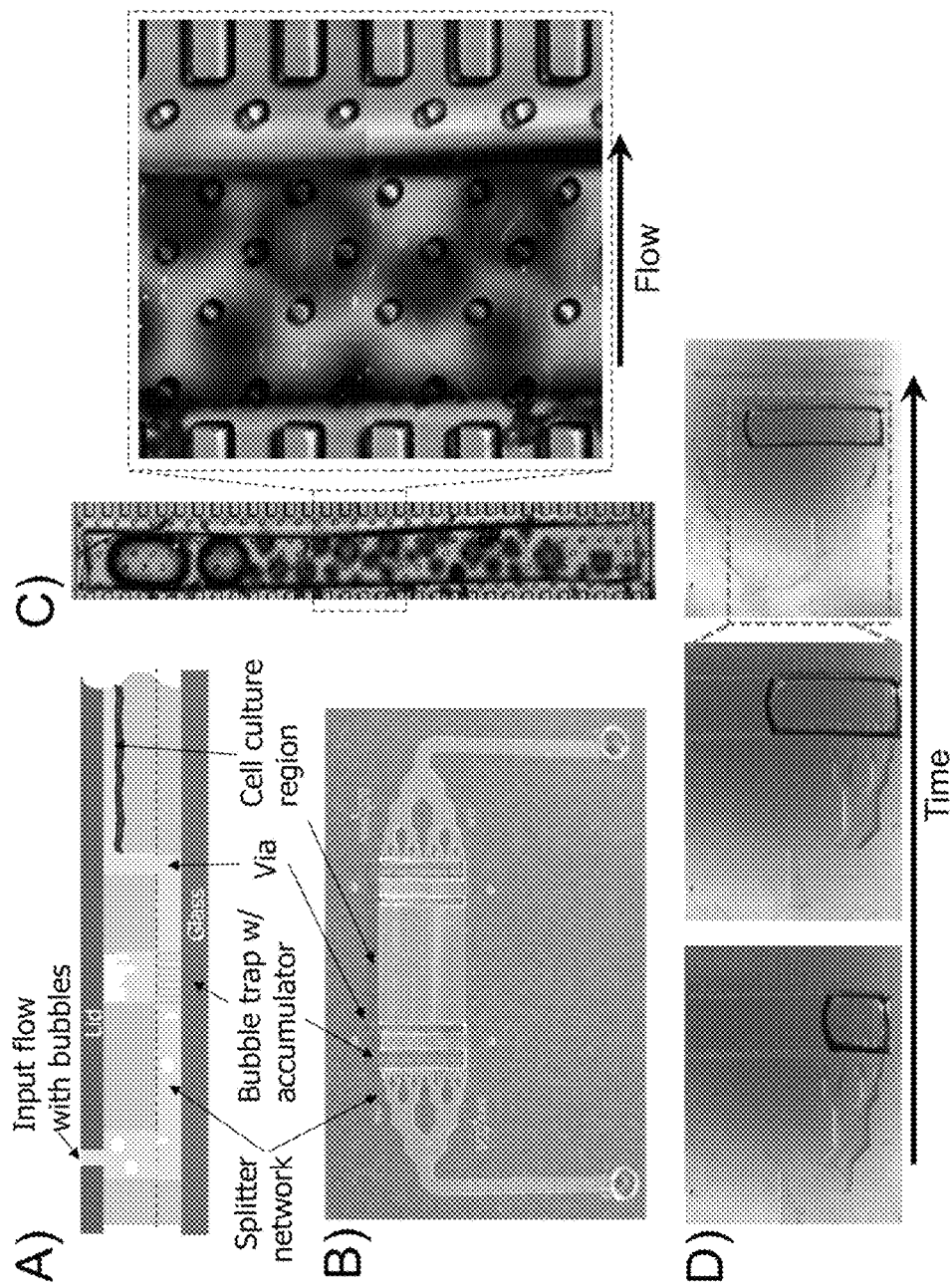

FIG. 22 shows schematically an alternative configuration of a microfluidic bubble trap according to one embodiment of the invention. (A) Block diagram of bioreactor containing a bubble trap. The lower layer contains a splitter to evenly distribute flow throughout the device and a forest of posts to arrest bubbles. Above the forest of posts is an accumulation volume into which bubbles rise after being trapped. (B) Picture of fabricated cell culture device/bioreactor containing a bubble trap. (C) A composite image of the bubbles (out of focus) that have risen into the accumulation volume above the posts, with flow passing undisturbed underneath as indicated by the in-focus comet trails of fluorescent beads suspended in fluid that is passing around the posts. (D) A test of accumulation of bubbles in the bubble trap by introducing a stream of bubbles with a bubble generator coupled to the bubble trap. Practical maximum volume of bubbles is approximately 80% of the accumulation volume. If the accumulation volume reaches capacity, a separate channel (not shown) can be used to aspirate them from the trap.

Figure 23:
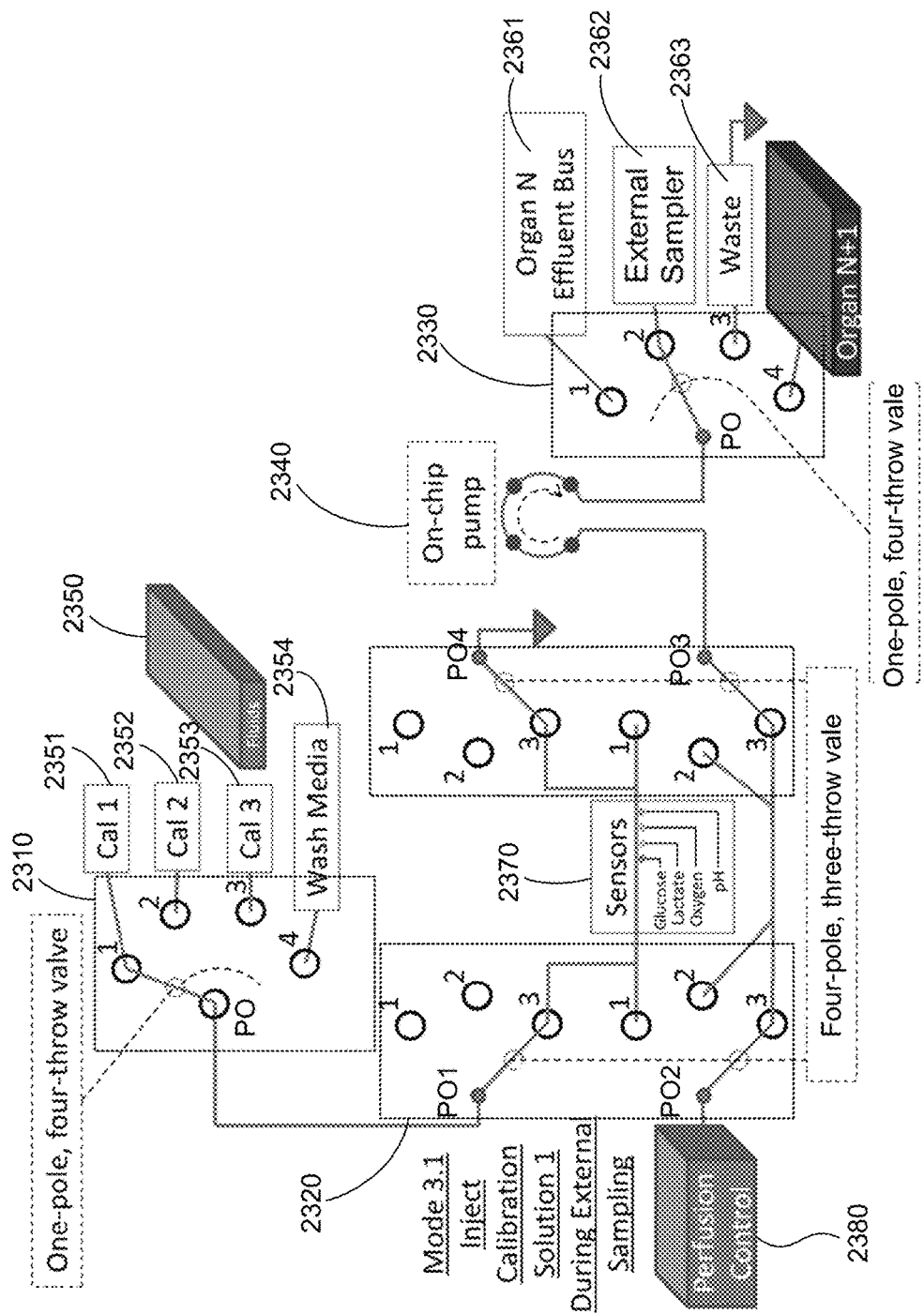

FIG. 23 shows schematically a microclinical analyzer according to one embodiment of the invention. There are three operational modes enabled by the four-pole three-throw valve in this system: (1) the Organ Output passes over the sensor array for electrochemical measurements of metabolites. (2) The Organ Output bypasses the sensor array, and the sensor array is isolated to prevent sensor fouling by proteins in the perfusate during those intervals of time for which the sensor array is not in use. (3) The Organ Chip perfusate bypasses the sensor array, allowing the sensor array to be calibrated with three or more calibration solutions or loaded with wash media by means of a one-pole four-throw valve, with the waste sent to drain to protect all organs from calibration fluids.

A one-pole four-throw valve allows the effluent from Organ N to pass onto the perfusion bus for that organ, to be delivered to an external sampler, or to Organ N+1. Additional poles on the switches would enable additional modes.

Figure 24:
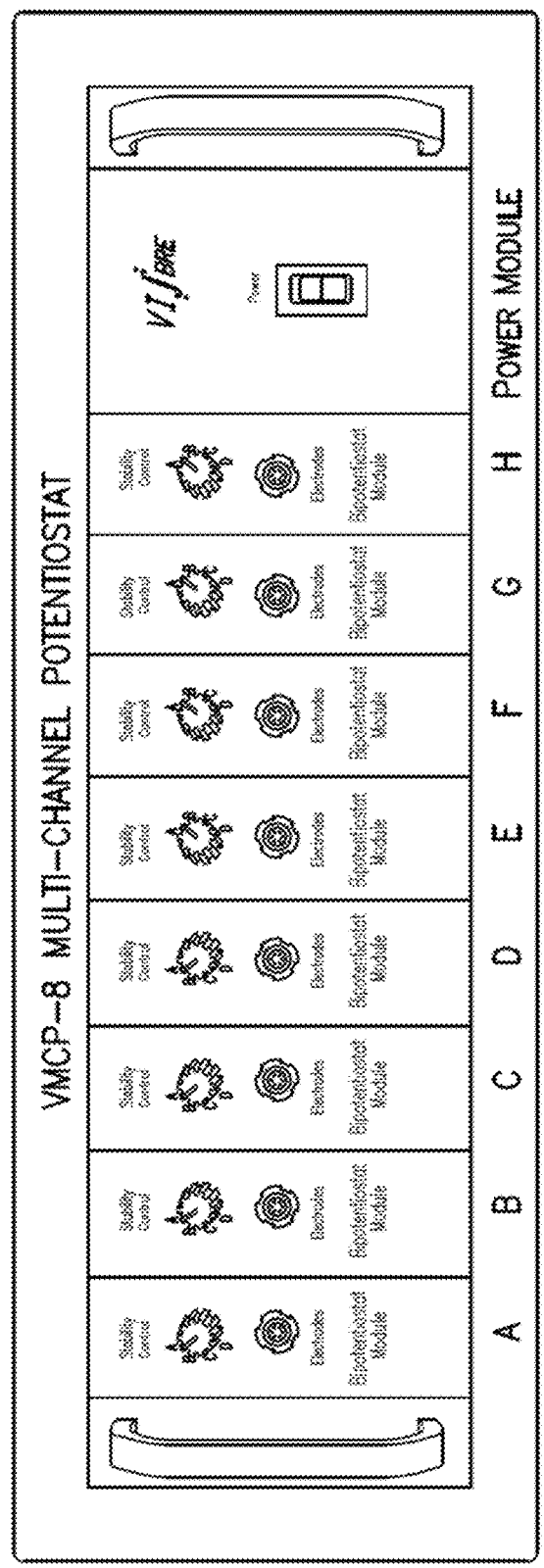

FIG. 24 shows schematically VIIBRE multichannel multipotentiostats. The electronics in this instrument are connected to electrochemical sensors in a microclinical analyzer and used to sense the metabolic state of multiple organs-on-chip according to one embodiment of the invention.

Figure 25:
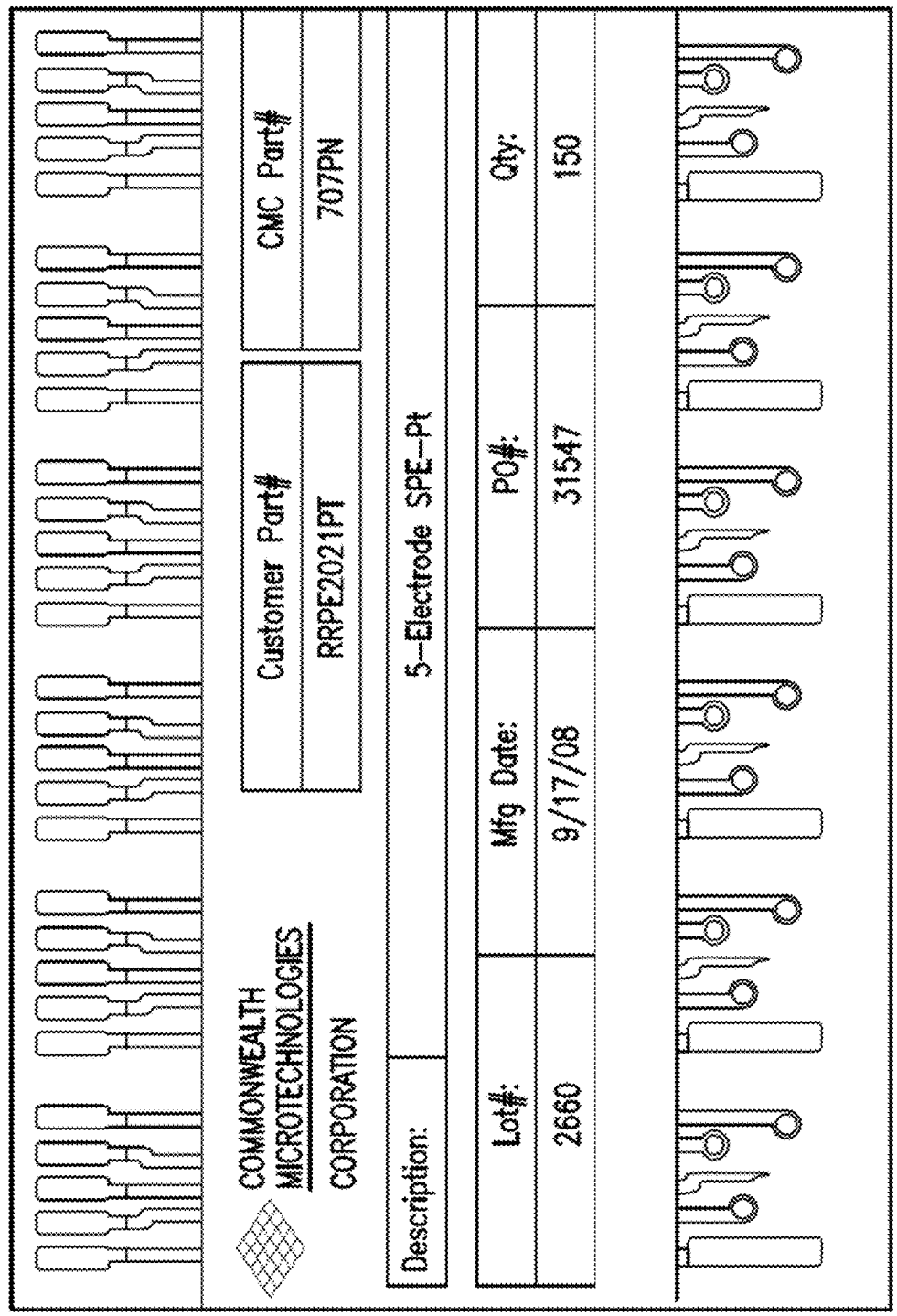

FIG. 25 shows schematically a sensor array chip for the microclinical analyzer. This figure shows sensors for six microclinical analyzers that each have five platinum electrodes for Glucose, Oxygen, Lactate, pH sensors, and a counter electrode.

FIG. 26 shows schematically tissue/cellular studies in the multianalyte microphysiometer.

Figure 27:
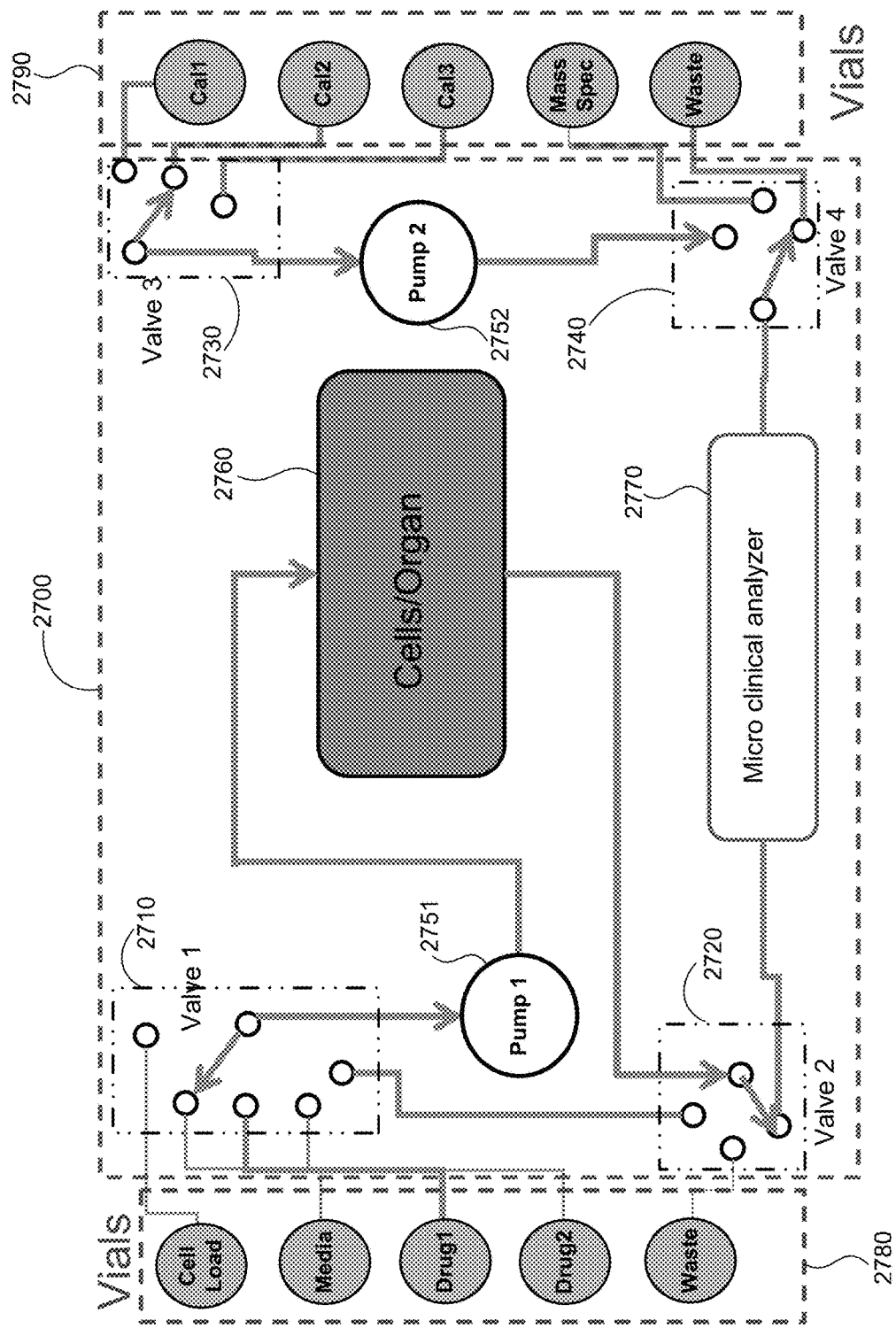

FIG. 27 shows a schematic of fluidic routing in an IOM chip according to one embodiment of the invention. Areas 2780 and 2790 are off-chip stock solution storage vials, and area 2700 is all part of the fabricated, disposable IOM chip.

Figure 28:
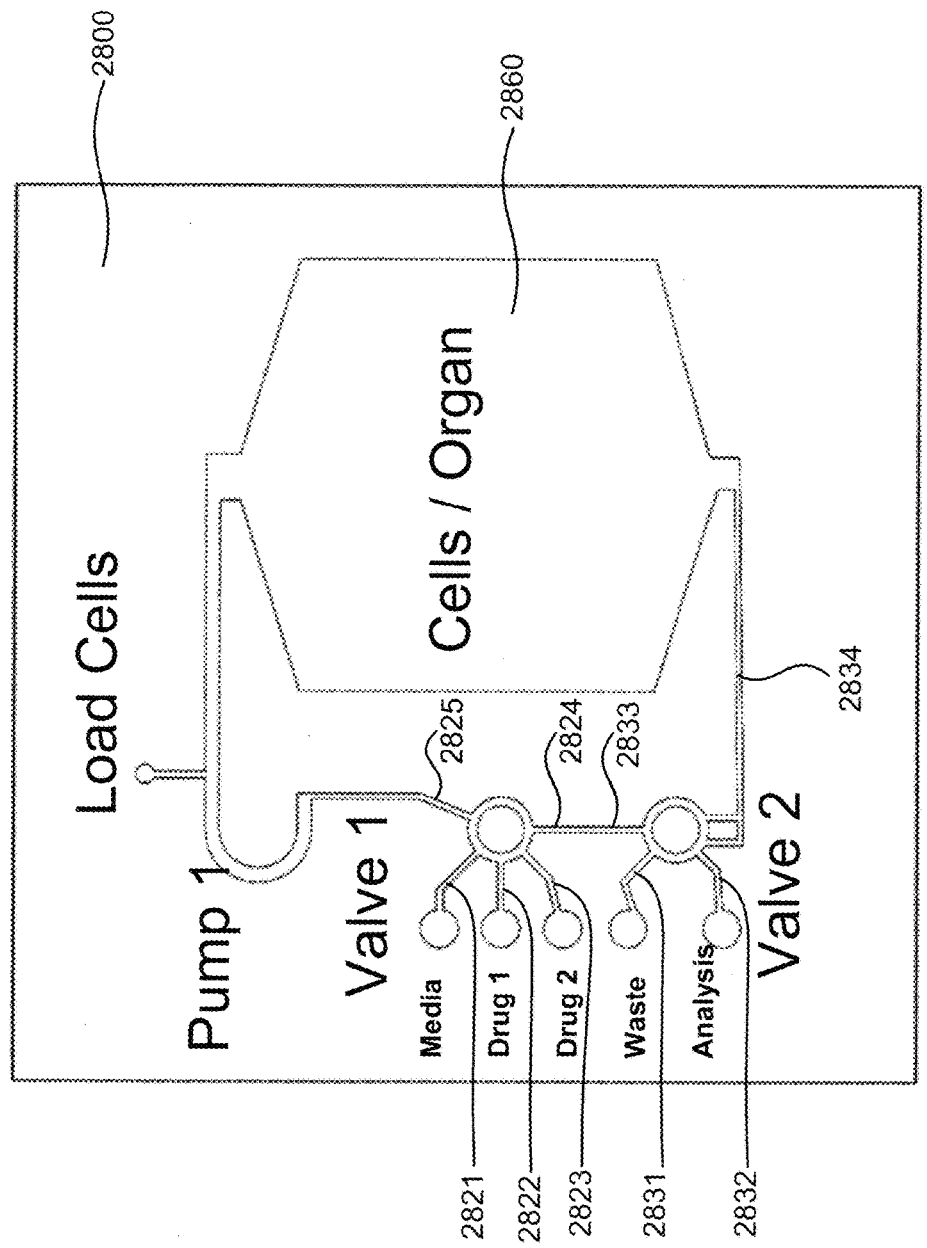

FIG. 28 shows a schematic of a single organ IOM chip with one pump, two valves, and a central area for the cells/organ according to one embodiment of the invention. The IOM chip supports cell loading, reperfusion, and sample retention for analysis.

Figure 29:
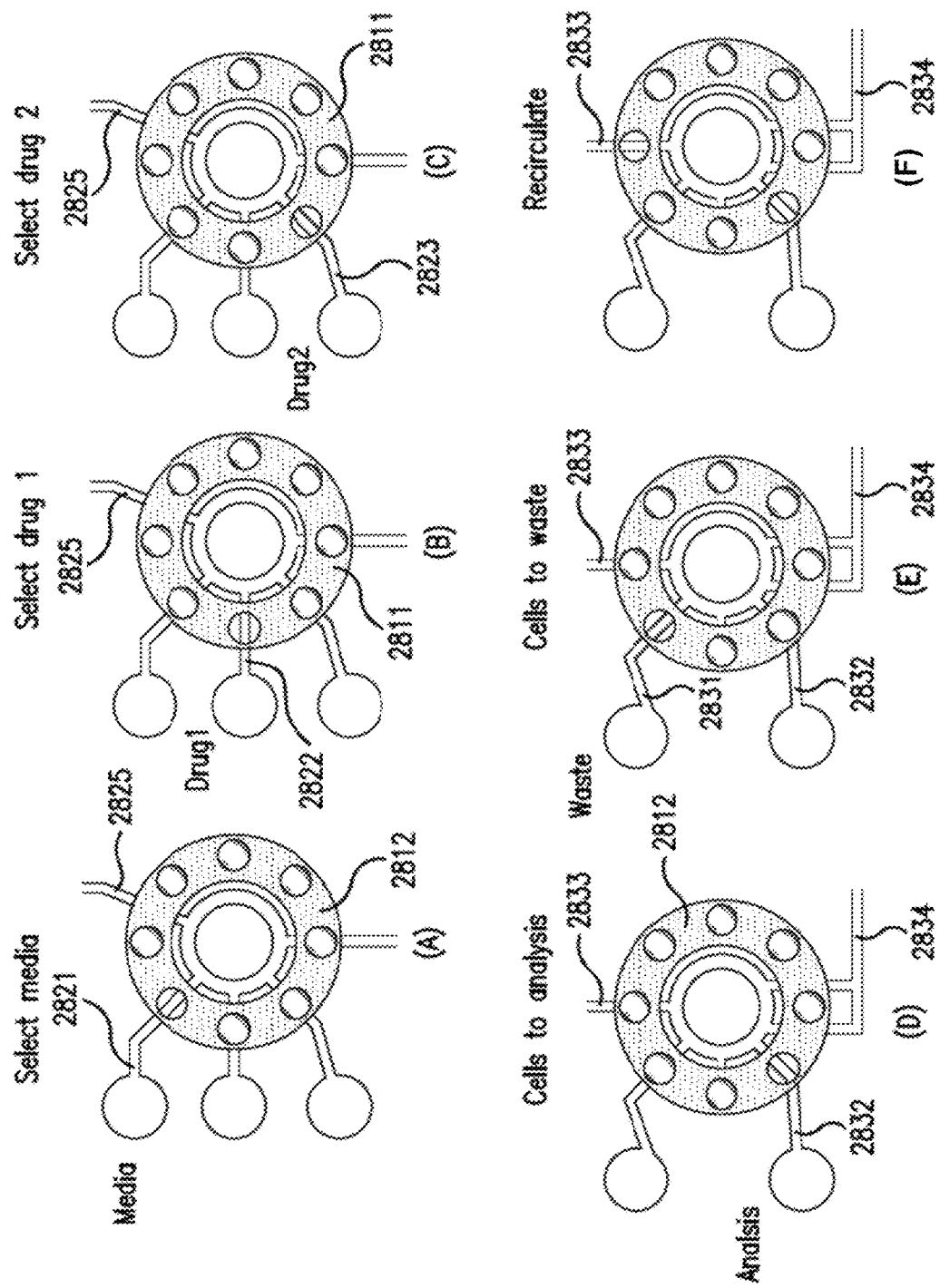

FIG. 29 shows schematically various valve configurations of Valve 1 (A)-(C), and Valve 2 (D)-(F), of the signal organ IOM chip shown in FIG. 28.

Figure 30:
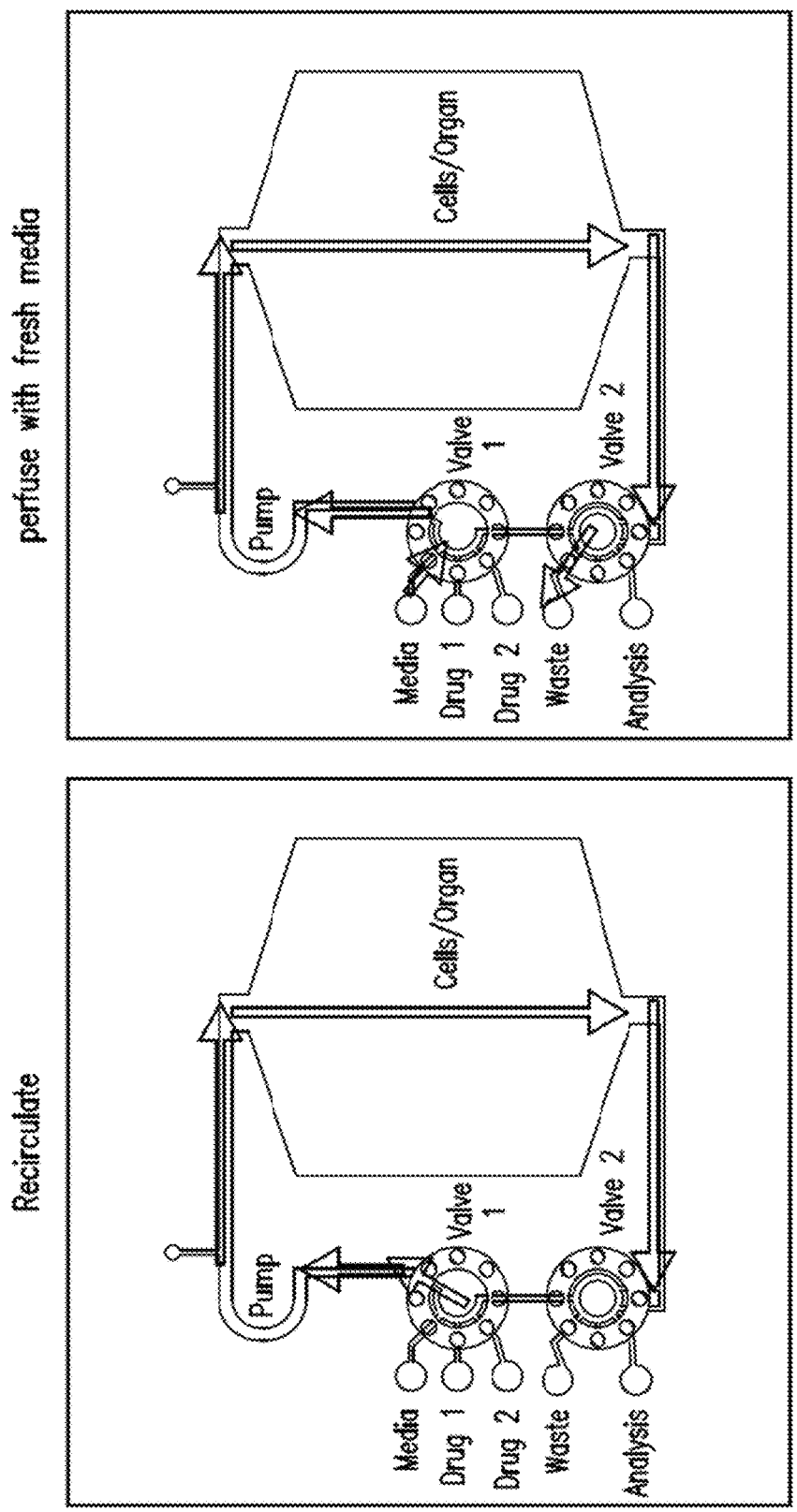

FIG. 30 shows schematically valve configurations when recirculating cell media (A) and applying media to biosample with overflow to waste (B) of the signal organ IOM chip shown in FIG. 28.

Figure 31:
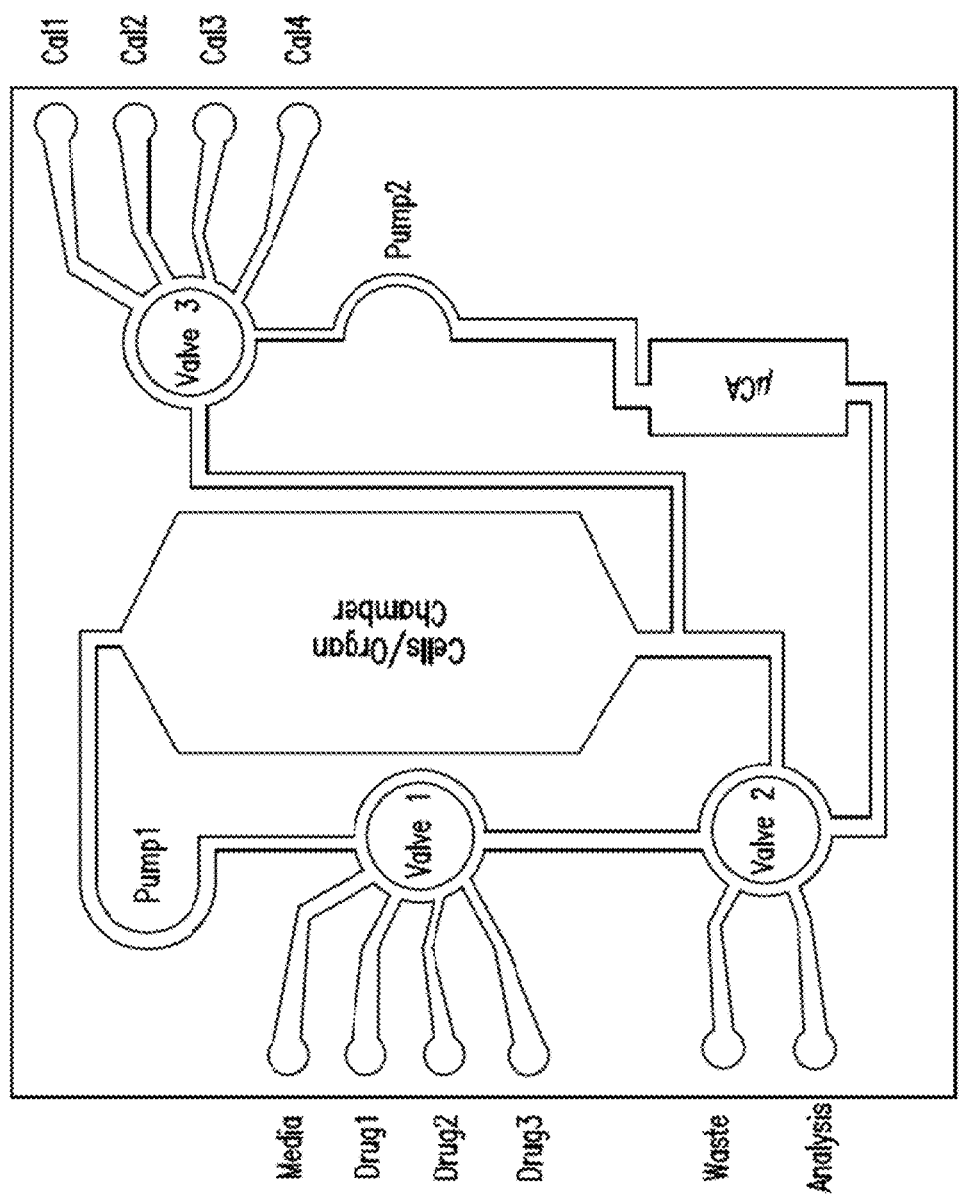

FIG. 31 shows a schematic of an organ IOM chip with a built-in microclinical analyzer according to one embodiment of the invention. Appropriate fluidic connections for calibration solutions, recirculation, and cellular efferent analysis are included in this design.

Figure 32:
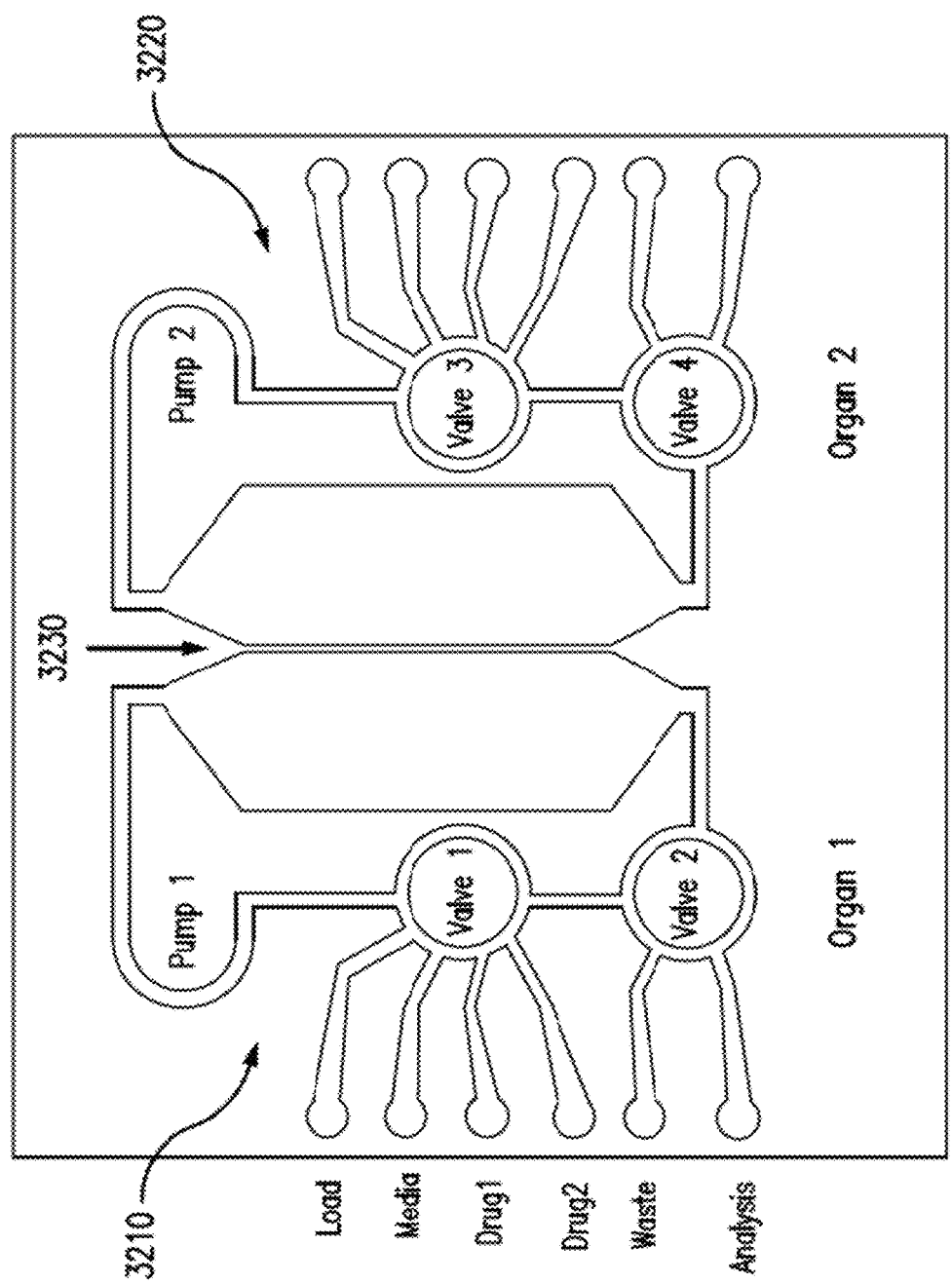
Figure 33:
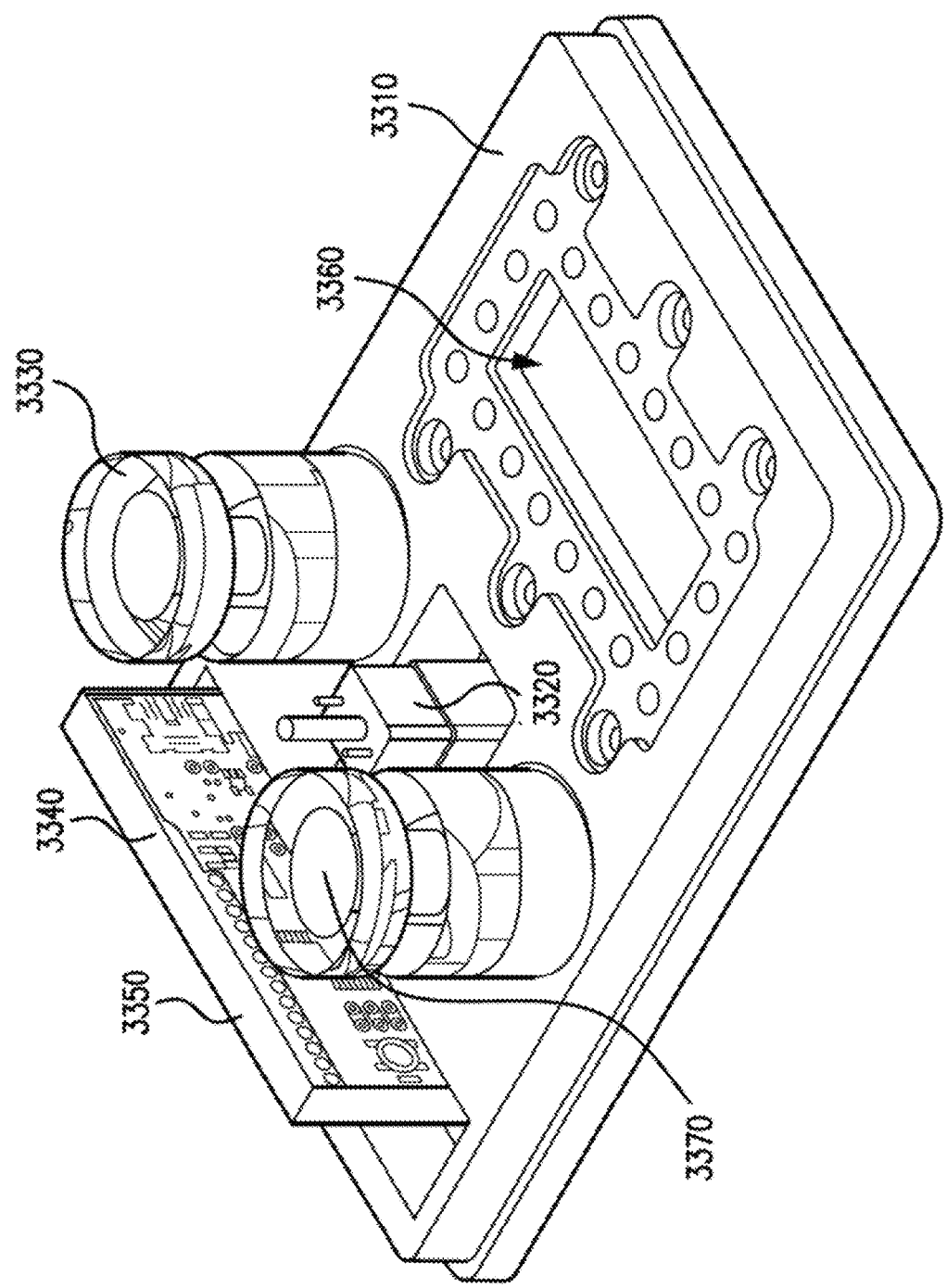

FIG. 32 shows a schematic of a double organ IOM chip with two pumps, four valves, and a thin membrane (3230) separating the two organs according to one embodiment of the invention FIG. 33 shows a theoretical embodiment of an intelligent chip carrier in SBS format according to one embodiment of the invention.

Figure 34:
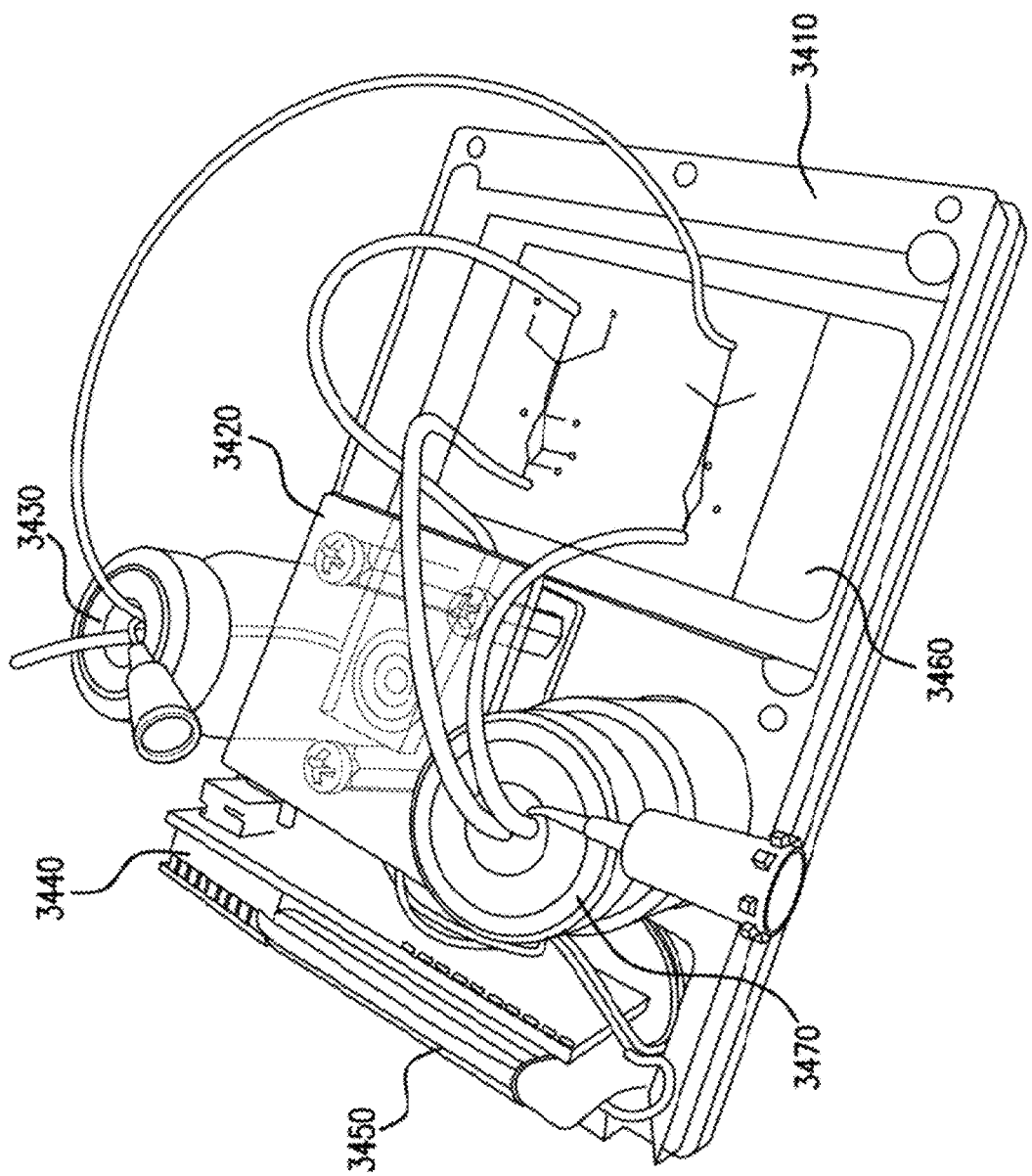

FIG. 34 shows an implementation of an intelligent chip carrier in SBS format according to one embodiment of the invention.

Figure 35:
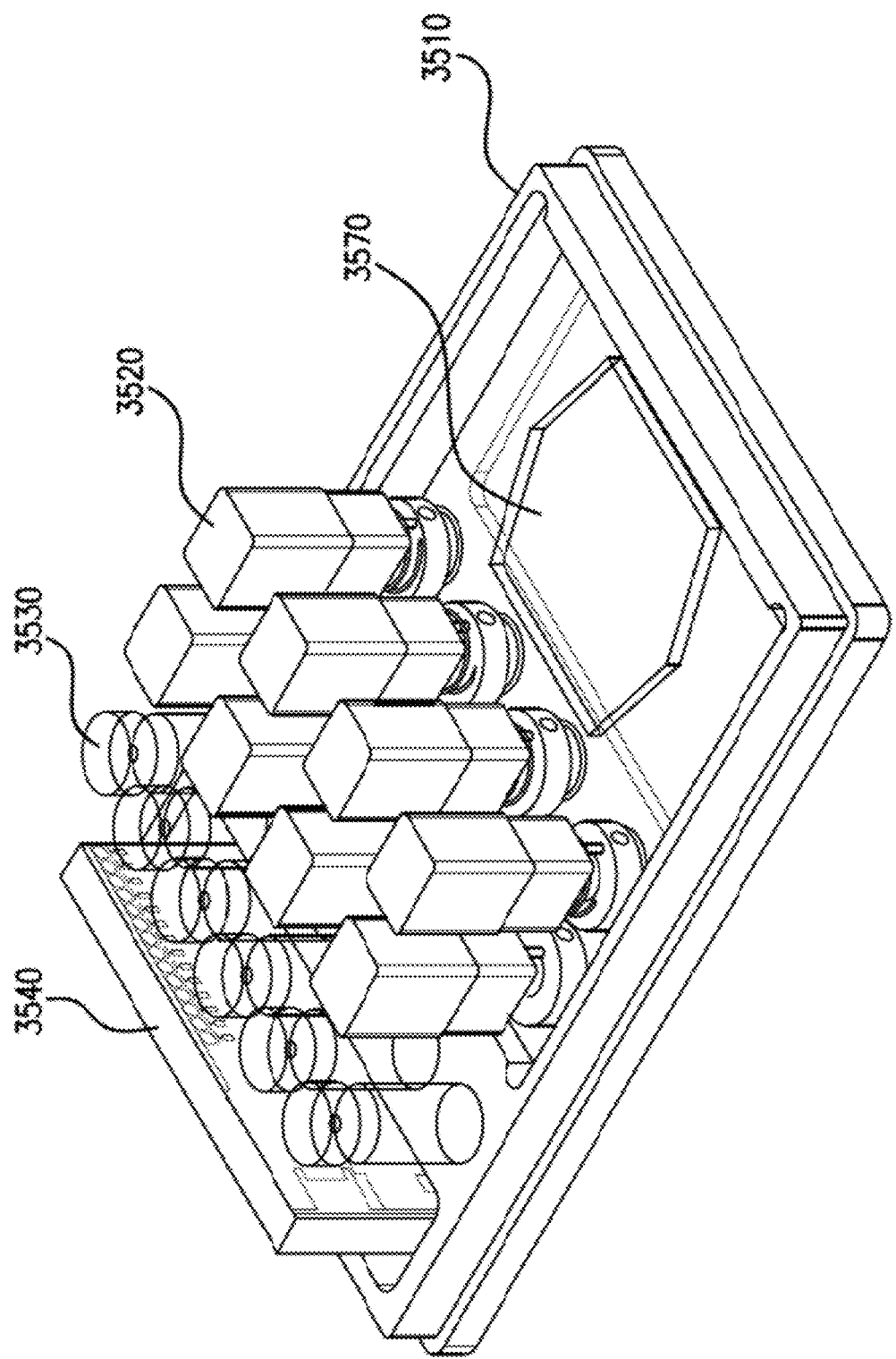

FIG. 35 shows a theoretical embodiment of an IOM chip with supporting chip carrier/cartridge according to one embodiment of the invention. This exemplary IOM chip has 8 microfluidic pumps or valves and controlling electronic hardware, with the pumps or valves interfaced to the IOM chip.

Figure 36:
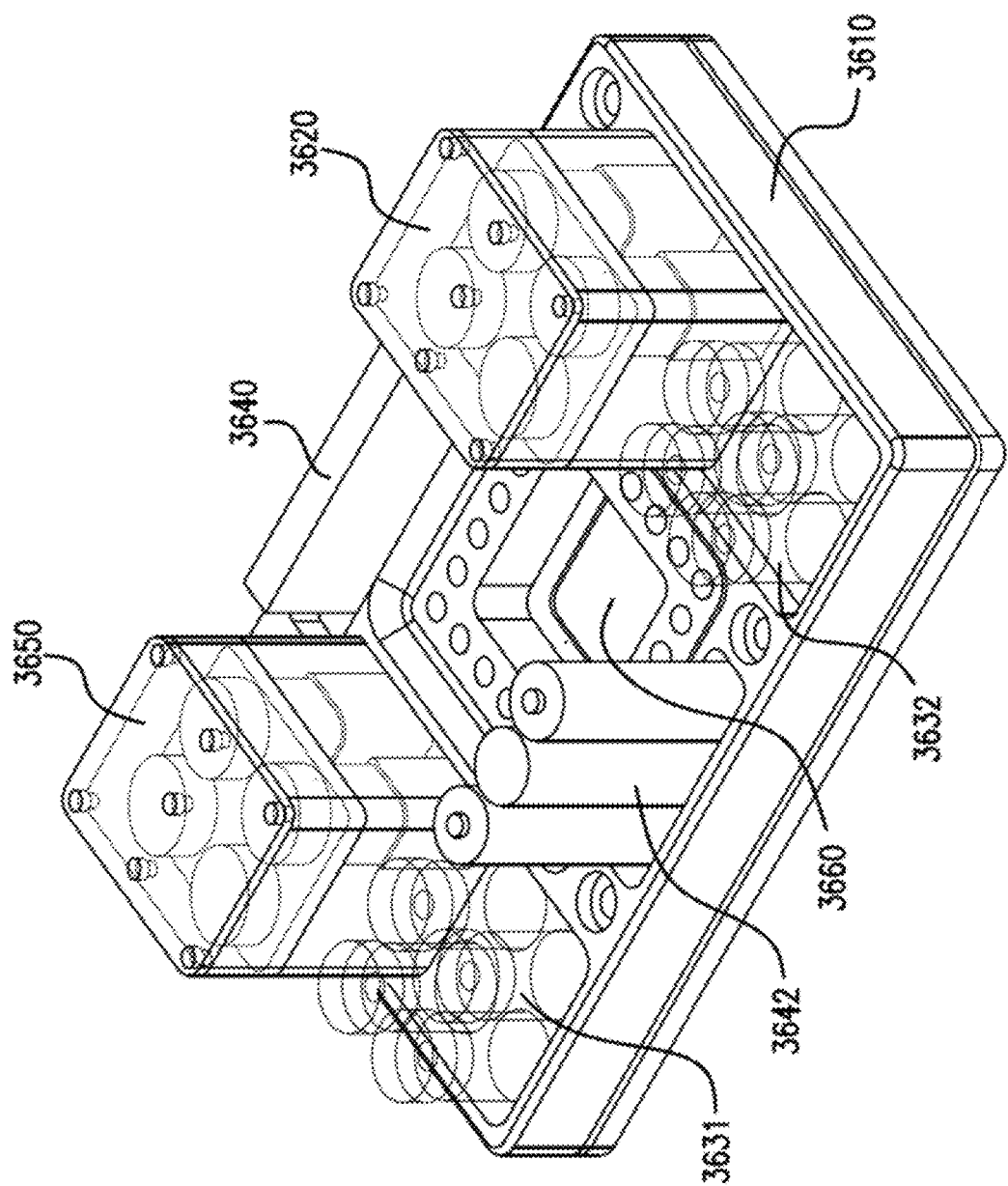

FIG. 36 shows a schematic of an intelligent chip carrier in SBS format configured as a perfusion controller/microclinical analyzer (PC/μCA) according to one embodiment of the invention.

Figure 37:
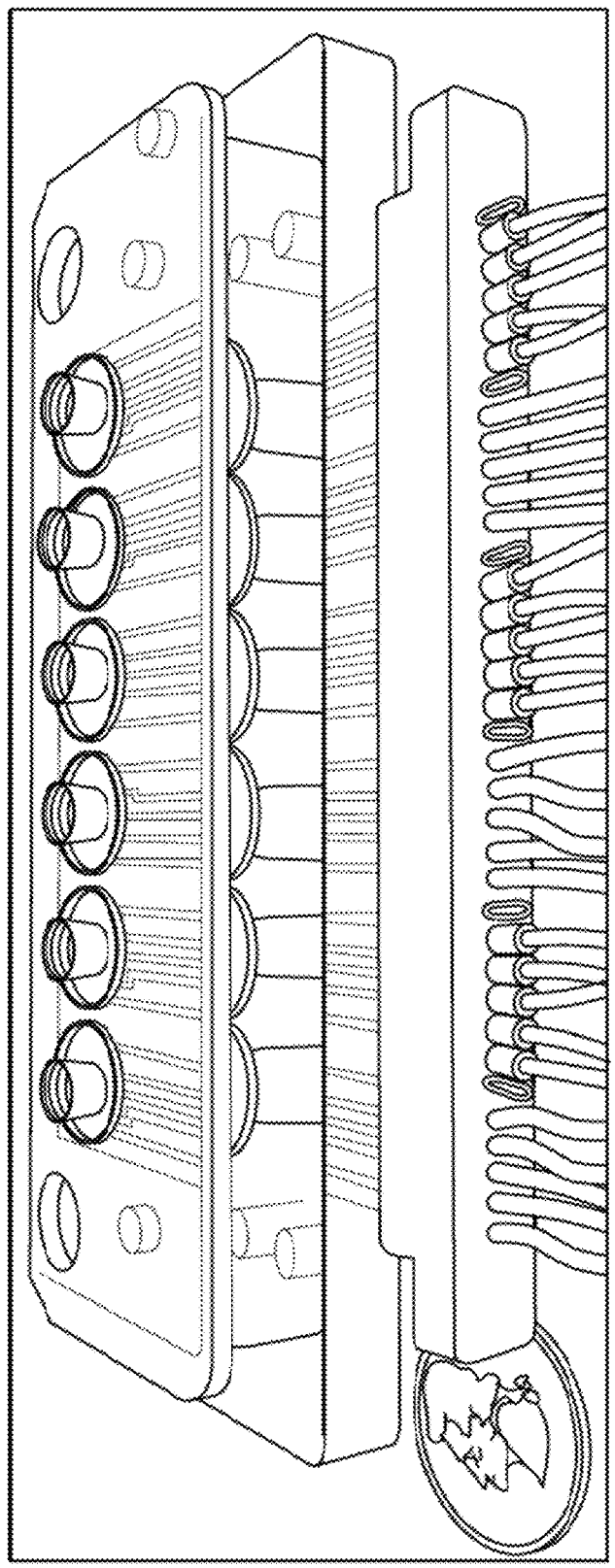

FIG. 37 shows a six-channel μCA screen-printed sensor array with a custom-manufactured fluidic housing.

Figure 38:
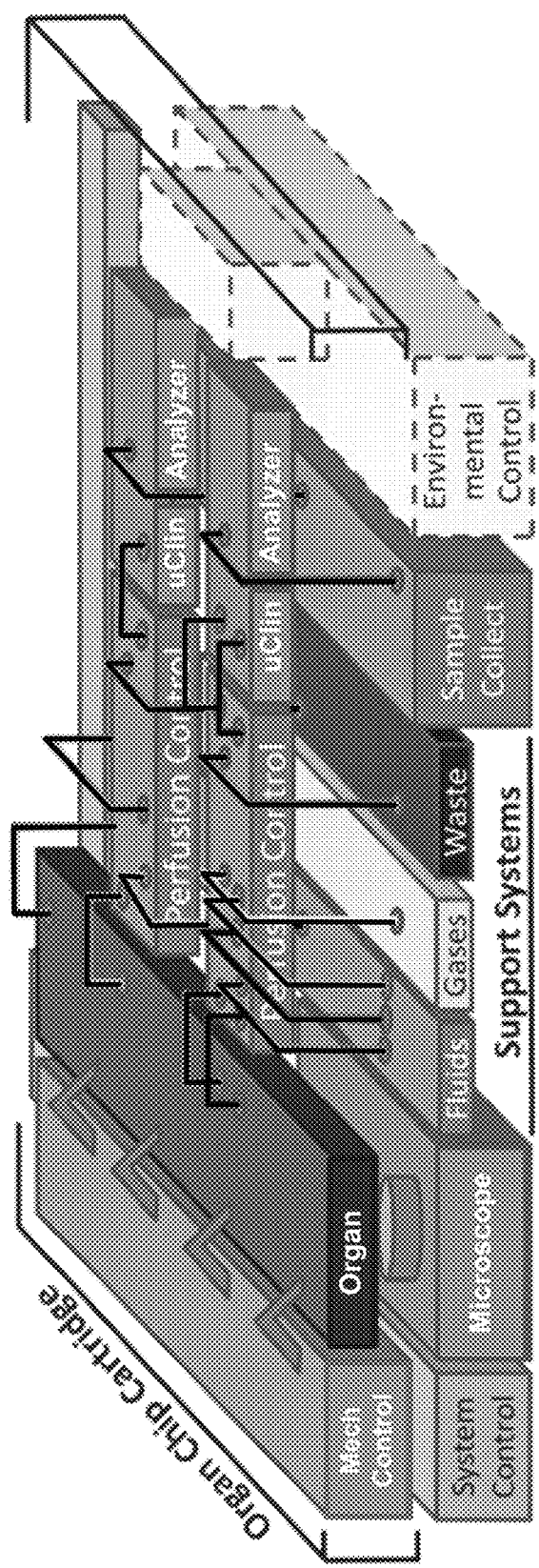

FIG. 38 shows schematically an Organ Cartridge that does not require the microfluidic microvasculature or the microfluidic interstitial space according to one embodiment of the invention. This example illustrates an arrangement of sub-assemblies, including a mechanical controller that senses strain and applies either pneumatic or mechanical stresses to the organ chip. The perfusion controller (PC) contains the pumps, pressure sensors, and microfluidics for perfusion, sample collection, drug delivery, and waste disposal. The microclinical analyzer (μCA) uses a commercial, low-cost, screen-printed electrochemical electrode array to make regular measurements of glucose, lactate, pH, and oxygen to track organ metabolic activity and health. For systems with two compartments, e.g., a tissue interstitium and a microvasculature or a bronchial space and a microvascular space, there will be parallel PCs and μCAs for each compartment. The fluid bus contains both the arterial and venous systems and other fluids, e.g., nutrients, drugs. The gas supply will deliver $O_2$, $N_2$, $CO_2$, etc. The small connecting tubing will in fact be in the form of custom interconnects. Electrical wiring uses a cartridge electrical bus that connects to a multi-organ experimental platform. The connection could also be done with a wireless communication protocol.

Figure 39:
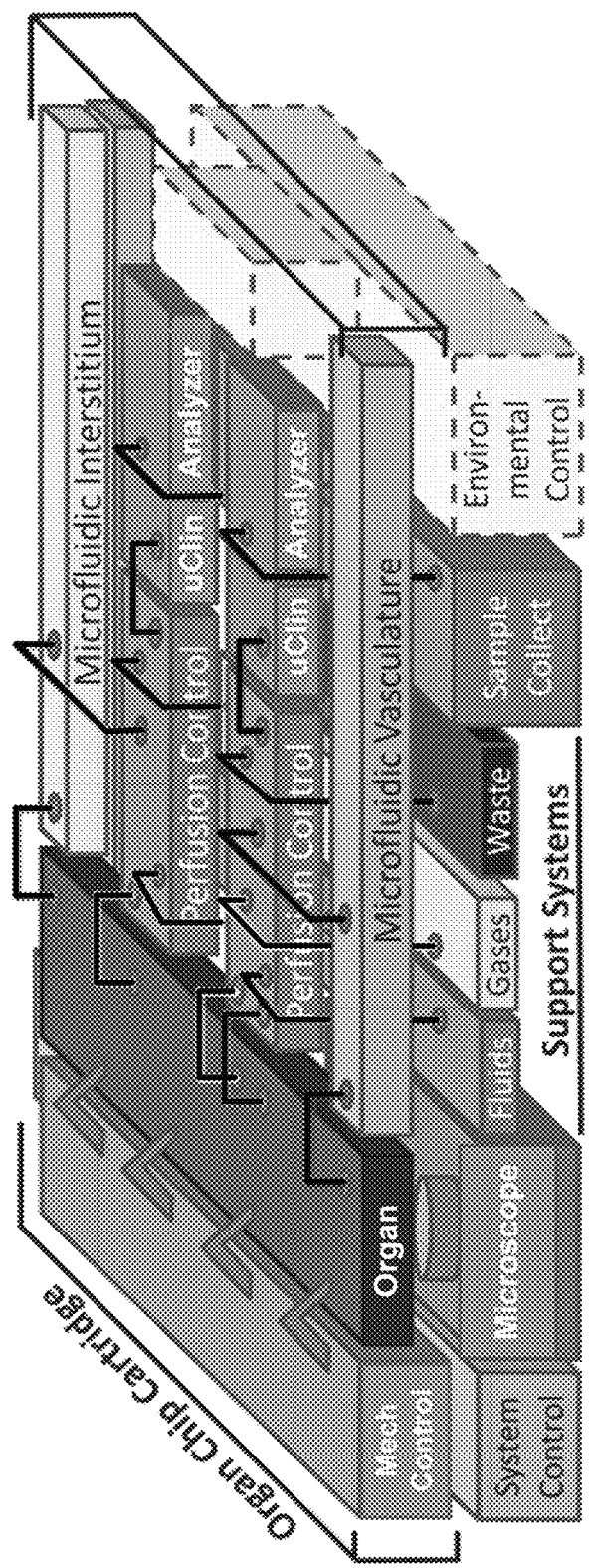

FIG. 39 shows a schematic diagram of an organ cartridge according to one embodiment of the invention. The cartridge contains a Mechanical Controller (MC) that senses strain and applies either pneumatic or mechanical stresses to the Organ Chip (OC). The perfusion controller (PC) contains the pumps, pressure sensors, and microfluidics for perfusion, sample collection, drug delivery, and waste disposal. The microclinical analyzer (μCA) can utilize a commercial, low-cost, screen-printed electrochemical electrode array or other type of electrode array, connected to a multichannel multipotentiostat to make regular measurements of glucose, lactate, pH, and oxygen to track organ metabolic activity and health. For systems with two compartments, e.g., an interstitium and a microvascular space or a bronchial space and a microvascular space, there will be parallel PCs and μCAs for each compartment. The microvasculature and microfluidic interstitium are disposable interconnects that may incorporate the discrete tubing shown interconnecting the various components. The underlying support systems include a Master Electronic System Controller or microcontroller, a Microscope, a Fluid Supply for nutrients, drugs, etc., a Gas Supply for $O_2$, $N_2$, $CO_2$, etc., a Waste line, a means for Sample Collection, and an Environmental Controller that adjusts $O_2$, $CO_2$, humidity, temperature, etc.

Figure 40:
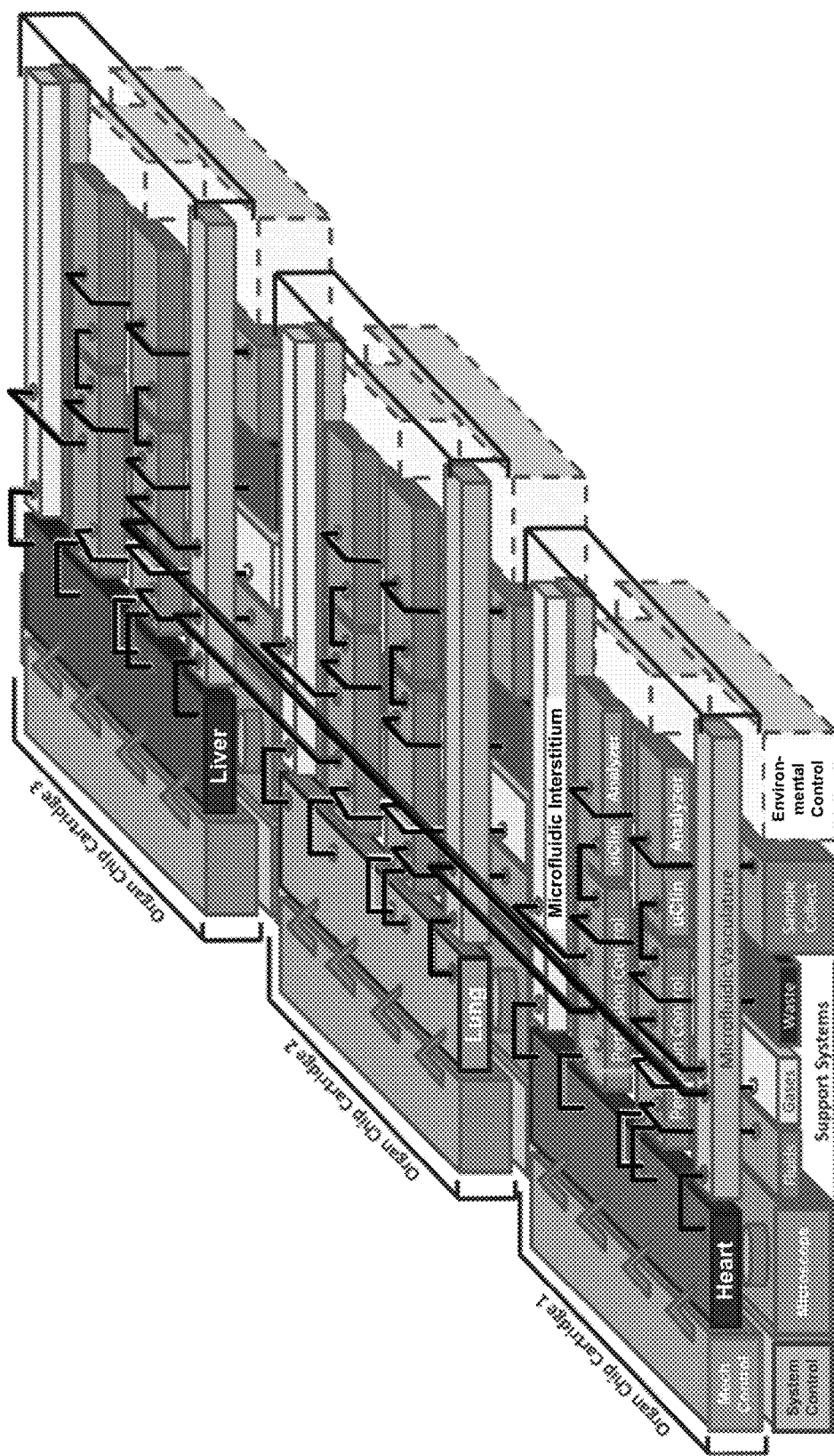

FIG. 40 shows a schematic diagram of an array of Organ Cartridges according to one embodiment of the invention. The individual organ cartridges can be connected together to form a multi-organ system in which fluids from one Organ Cartridge can be connected to other Organ Cartridges. In this example, the Heart module is shown as delivering fluids to the Lung module and the Liver module. The Lung and Liver are shown to be connected via a separate fluid connection. The underlying support network supplies fluids, gases, and waste removal according to the programmed status demands of each individual organ's Perfusion Control subsystem.

Figure 41:
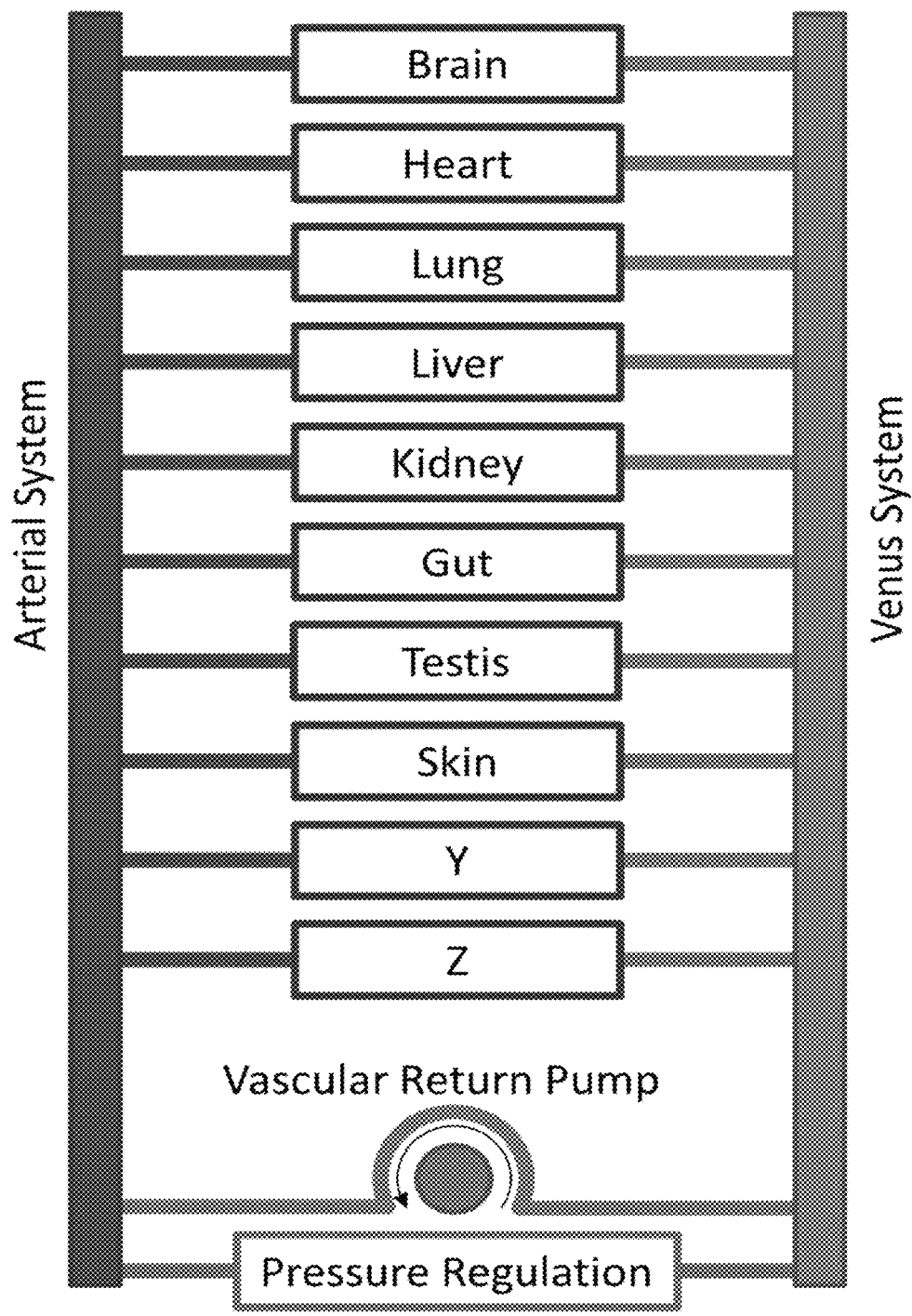

FIG. 41 shows schematically a parallel configuration of Organs-on-a-Chip according to one embodiment of the invention. The input to each organ-on-chip is connected to the common "arterial" supply line, and the effluent from each organ is connected to the common "venous" line. Each organ chip as shown could also include an individual perfusion controller and microclinical analyzer, with the pumps being either in series with the organ or in parallel. One or more vascular return pumps, with pressure regulators, return the venous flow to the arterial circulation, with gas exchange being provided by either a discrete membrane gas exchanger or another such device, or through the gas permeable properties of the material out of which the microfluidic device is constructed.

Figure 42:
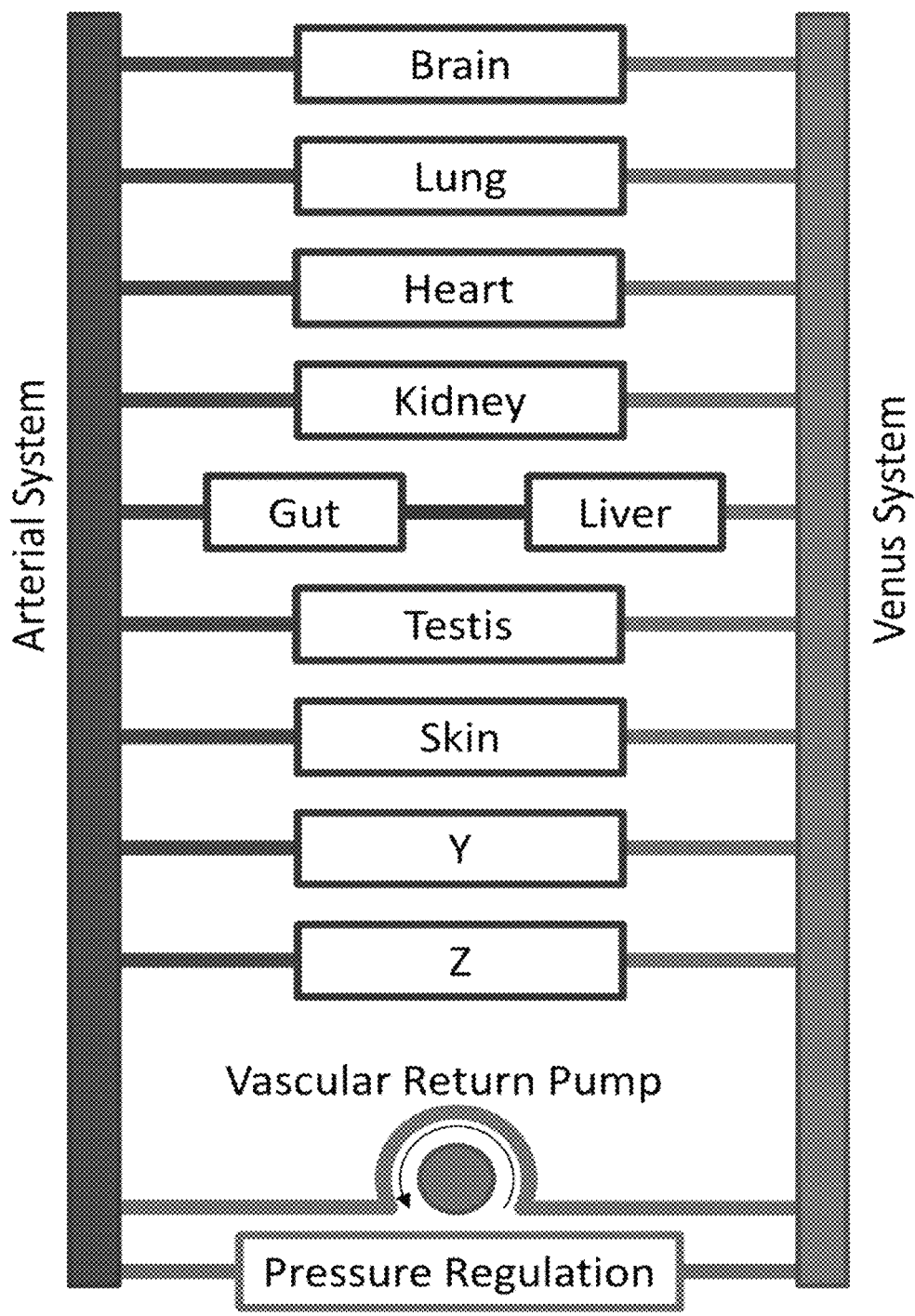

FIG. 42 shows schematically a parallel-series configuration of Organs-on-a-Chip according to one embodiment of the invention. The input to each organ-on-chip is connected either to the common "arterial" supply line, and the effluent from each organ is connected to the common "venous" line, in parallel mode, or two or more organs can be connected in series, here shown by the effluent from the gut entering the liver and then being passed to the common venous line. Each organ chip as shown could also include an individual perfusion controller and microclinical analyzer, with the pumps being either in series with the organ or in parallel. One or more vascular return pumps, with pressure regulators, return the venous flow to the arterial circulation, with gas exchange being provided by either a discrete membrane gas exchanger or another such device, or through the gas permeable properties of the material out of which the microfluidic device is constructed.

Figure 43:
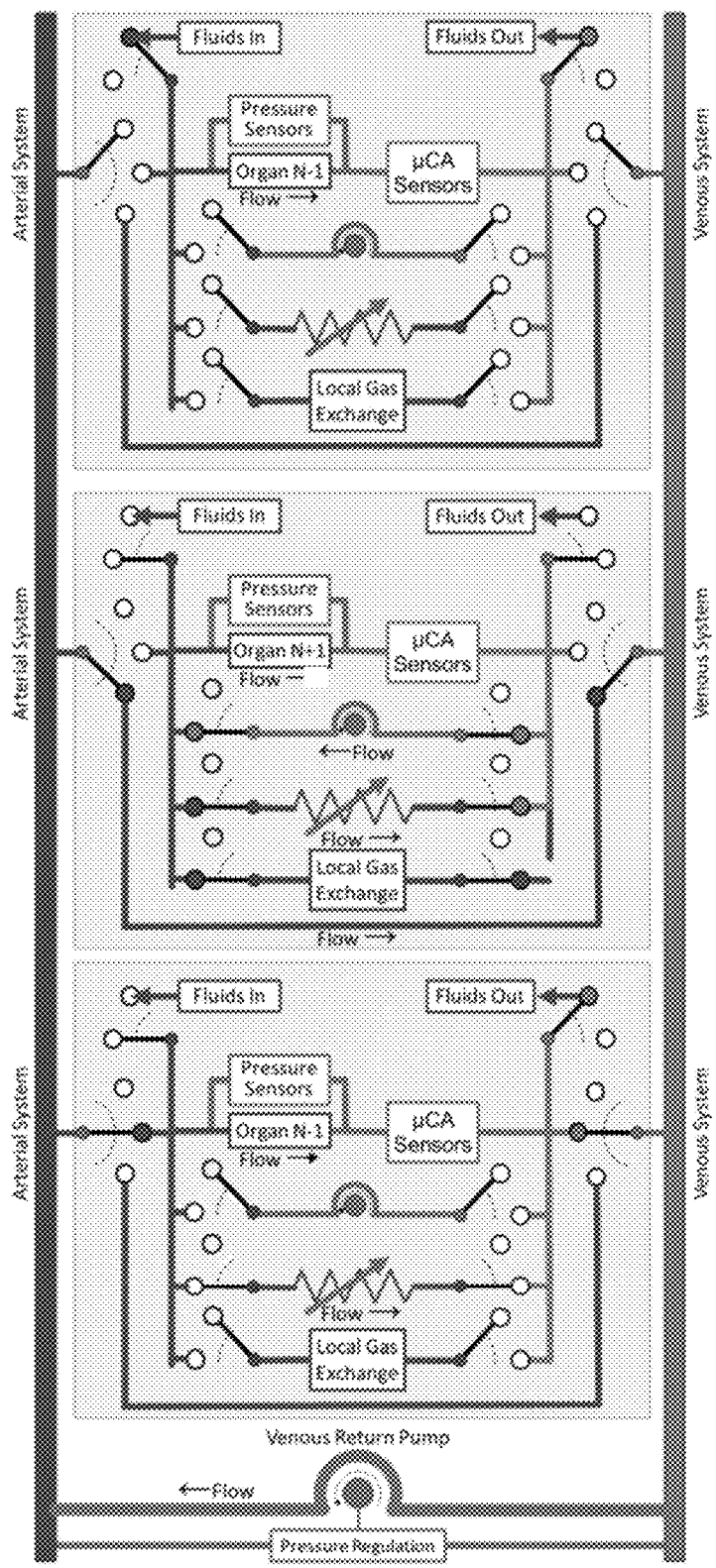

FIG. 43 shows schematically three perfusion controllers in an array of Organs-on-Chip according to one embodiment of the invention. The figure shows three different interconnected Organs. Upper: Introduction of fluid in Organ N–1 with the effluent going to a Fluids-Out port for either analysis or disposal. Middle: The cartridge for Organ N running on internal recirculation with local gas exchange and internal shunt to regulate the flow. The Arterial circulation bypasses the cartridge to maintain homeostasis of other organs. Lower: Organ N+1 is connected between the arterial and venous circulations with the variable low impedance shunt regulating the organ flow for the given arterial-venous pressure difference. A sample is being withdrawn for external analysis. At the bottom of the figure, a pump provides venous return. Organ-level gas exchangers or a master gas exchanger could be inserted if required.

Figure 44A:
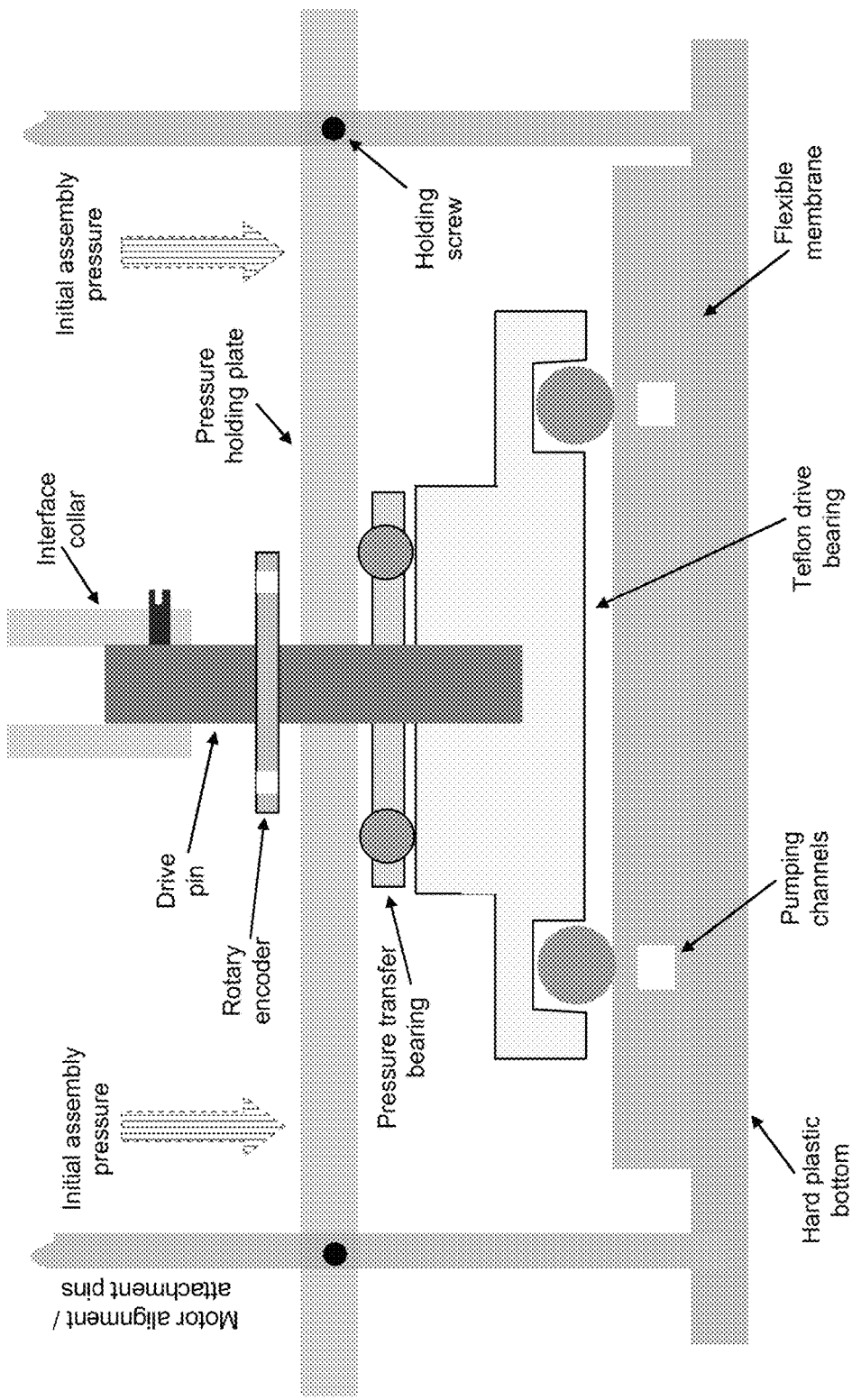

FIG. 44A shows schematically a design of one particular microfluidic compatible rotary planar device with design features that can be used either for use as a pump or as a valve. Two key advantages of this design are: 1) the critical pre-use tensioning of the roller balls against the flexible membrane is easily achieved by simply placing a known weight or force against the rigid pressure holding plate; and 2) the ball bearing cage is implemented as ball containing sockets directly and rigidly attached to the drive pin. For pre-tensioning, once appropriate pressure has been added (possibly via a calibrated donut shaped weight) then simply tightening the holding screws will establish a known compressive force underneath the ball bearings to actuate the desired pump or valve functionality. The pressure transfer bearing located under the pressure holding plate acts to enable low friction rotation of the Teflon or other low-friction drive bearing while at the same time providing uniform downward force pressure on the Teflon drive bearing. Since the shaft rotation is rigidly linked to the Teflon drive bearing, it allows for direct transfer of the rotation delivered either from a motor or a hand crank via interface collar to the fluid driving ball bearings. When the central shaft is rotated, typically via a motor or a hand crank, the rotary force is transferred to a Teflon or other low friction material which holds individual ball bearings captive in ball cages. Alternatively shafted roller bearings could be used to transfer force into the deformable membrane. A rotary encoder assembly can be used to provide electronic verification of ball speed and precise ball location—a critical parameter when the device is utilized as a rotary planar valve assembly.

Figure 44B:
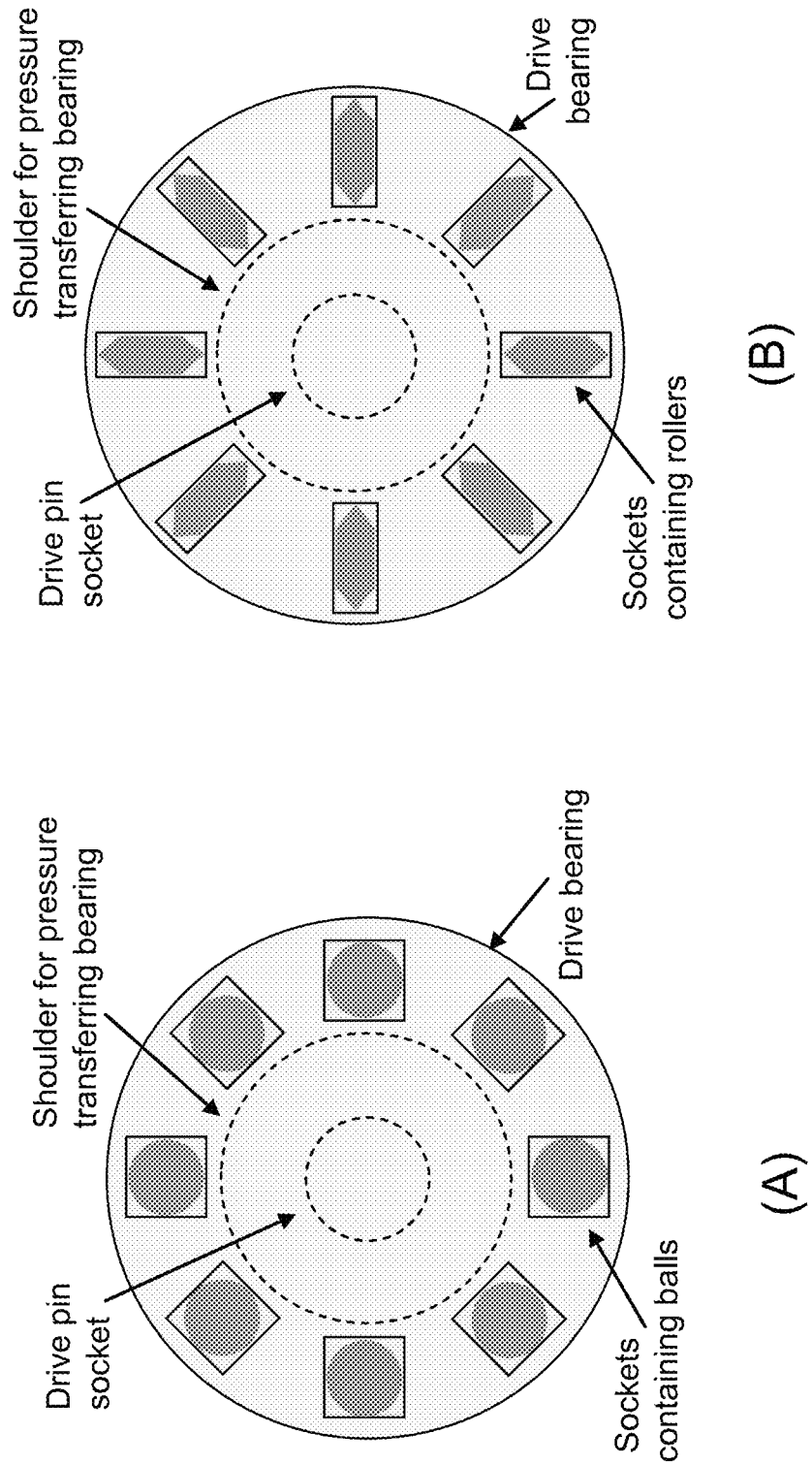

FIG. 44B shows bottom views of a drive bearing indicating that (a) balls and (b) rollers are housed within the sockets, according two embodiments of the invention. The drive bearing is utilized in the rotary planar device shown in FIG. 44A.

Figure 45:
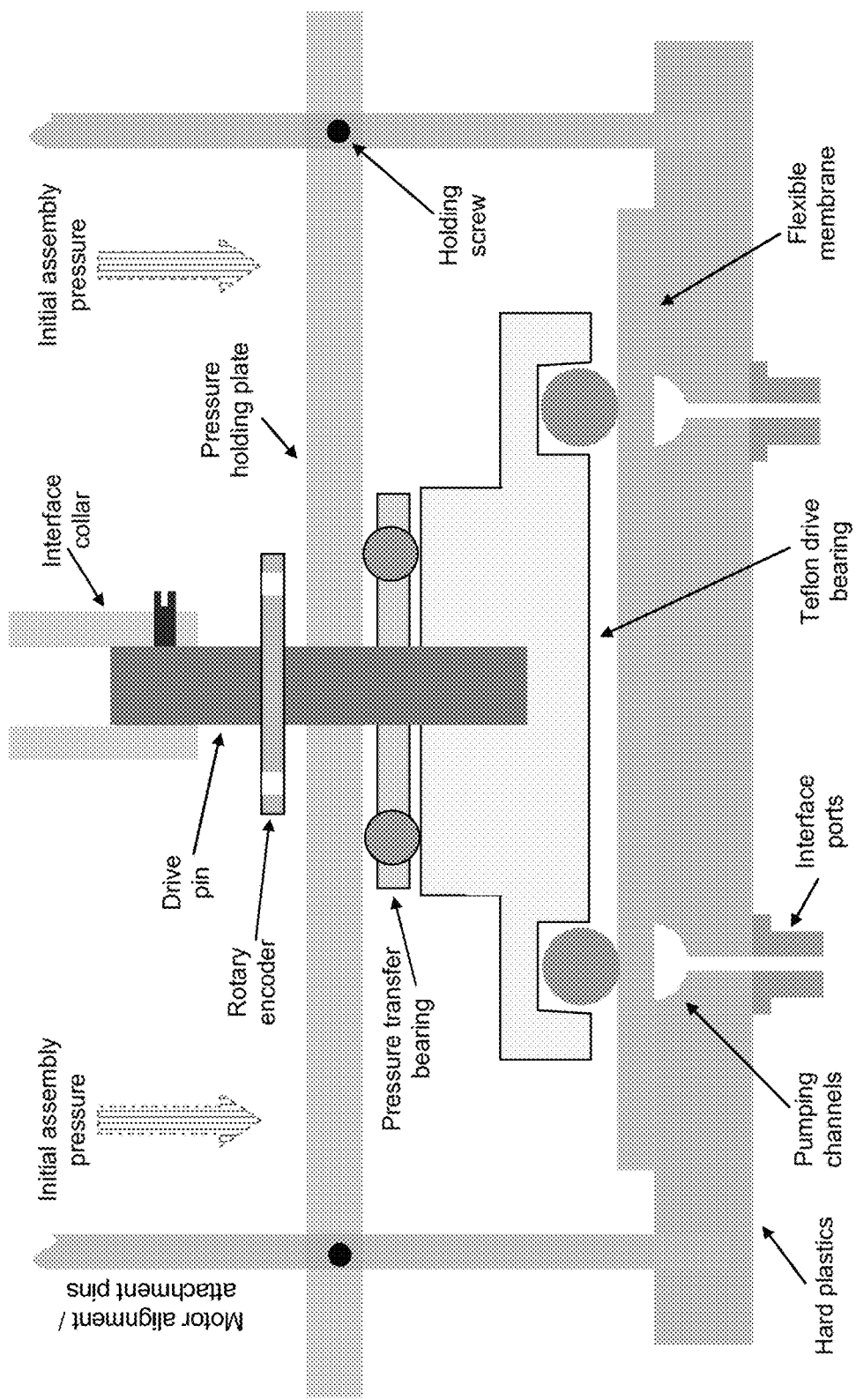

FIG. 45 shows a variation of the pumping module shown in FIGS. 44A and 44B where pumping channels are fabricated in hard plastics and covered with a flexible membrane forming one of the microfluidic channel sides. The membrane allows for channel closure when pressure is delivered by a rolling ball bearing. The hard plastic fluidic channel can be fashioned with semi-circular cross section to facilitate valve sealing.

Figure 46:
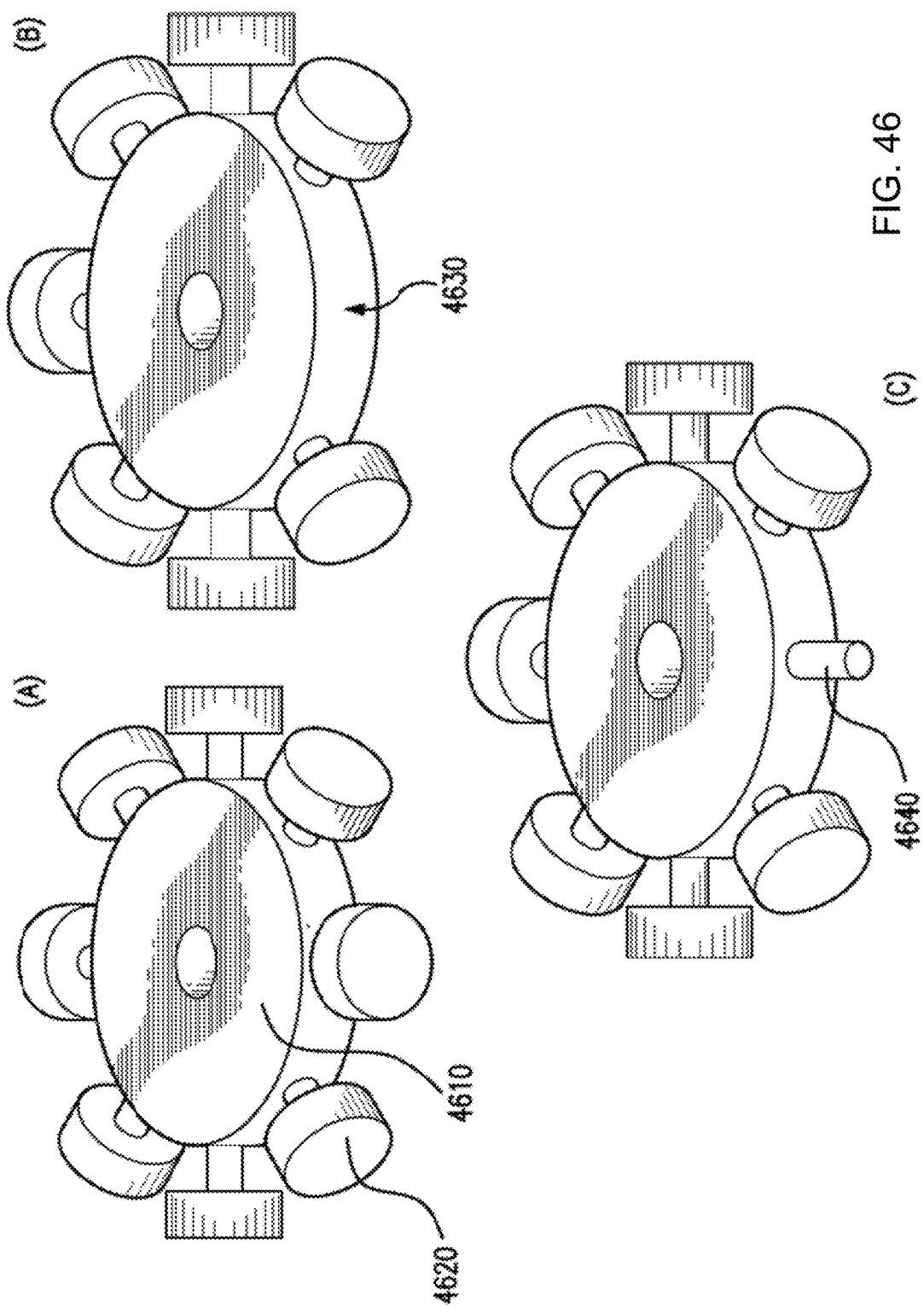

FIG. 46 shows various implementations of an axle-driven, cam-follower-bearing type actuator used to implement the RPPMs and RPVs according embodiments of the invention, (A) with cam followers spaced-equally mounted onto the cam, (B) with one missing cam follower at a location; (C) with a position indicator at the location in which the cam follower is missed.

Figure 47:
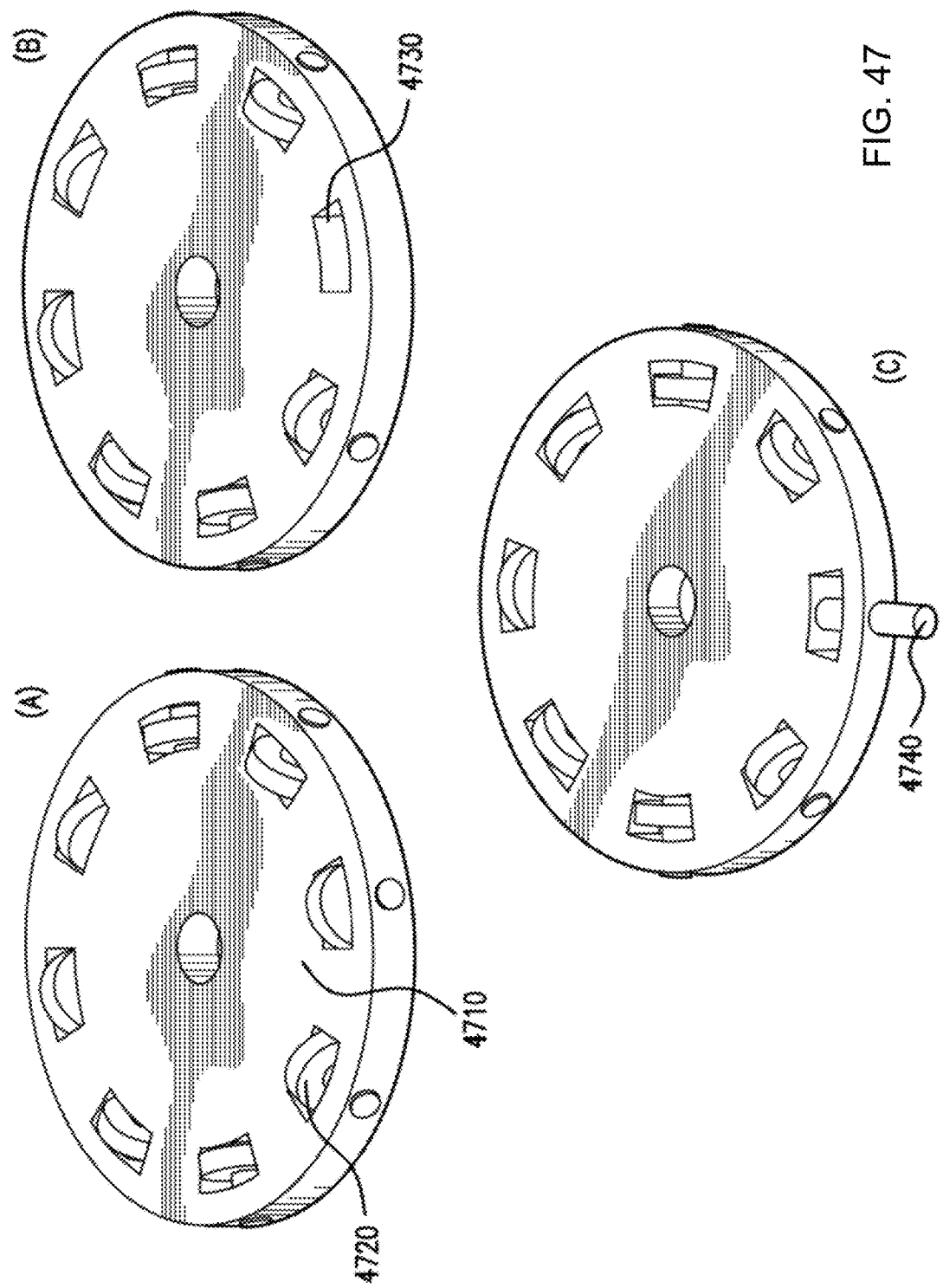

FIG. 47 shows various implementations of an axle-driven, roller-bearing type actuator used to implement the RPPMs and RPVs according embodiments of the invention, (A) with rollers mounted into the spaced-equally sockets, (B) with one roller missed in a socket; (C) with a position indicator at the location in which the roller is missed.

Figure 48:
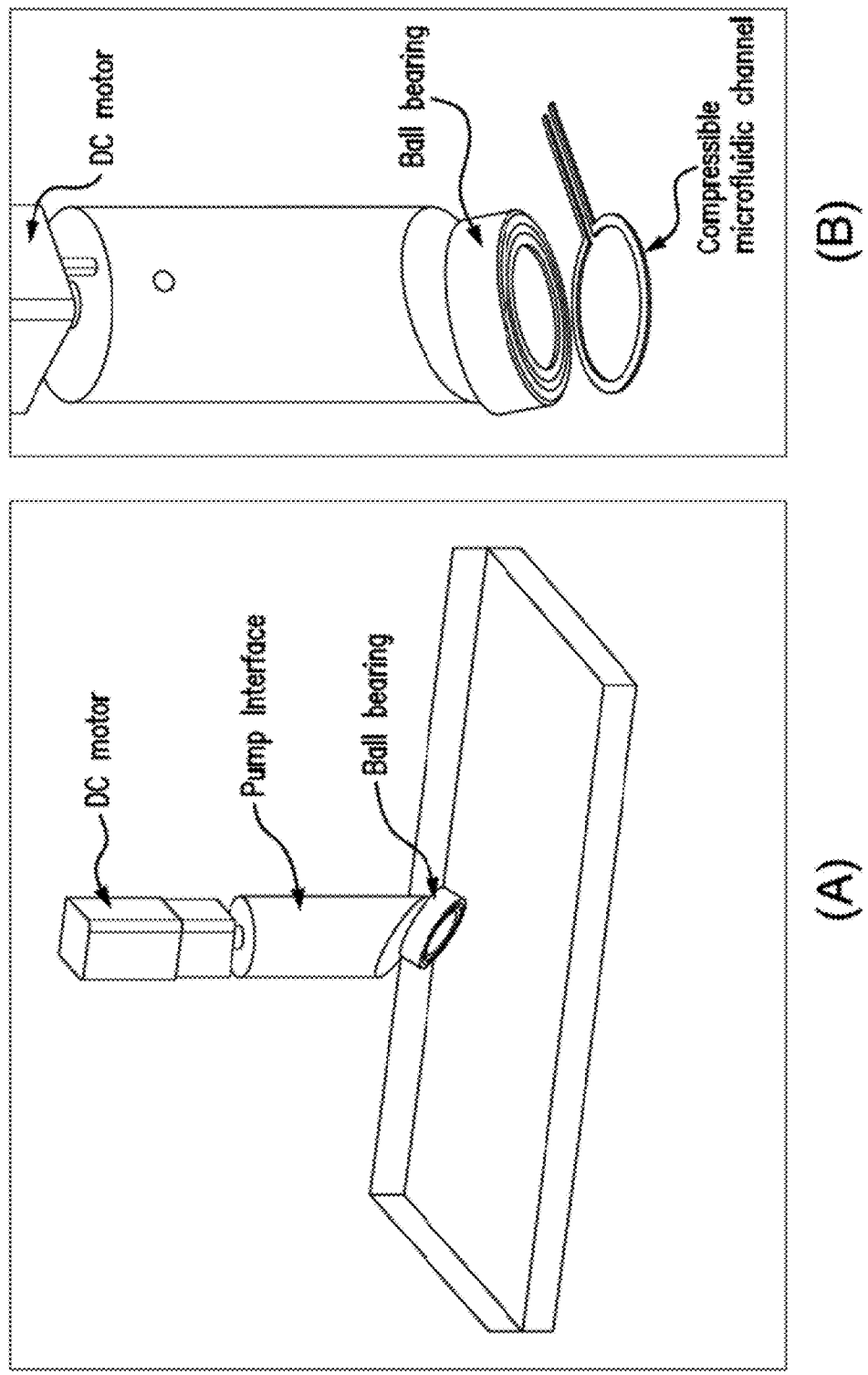

FIG. 48 shows the design of a roller or ball bearing caster pump assembly that can be used to create a peristaltic pump when used in conjunction with a planar microfluidic channel covered by a flexible membrane. The design incorporates a roller bearing mounted at an approximate 45 degree angle on a motor driven shaft. As the motor shaft rotates, the portion of the roller bearing in contact with the planar flexible membrane will trace a circular path on top of the embedded fluidic channel. Only one rounded edge of the roller or ball bearing outer rim will be in compressional contact with the flexible membrane, and the rolling rim bearing action will exert minimal frictional sliding force on the flexible membrane, thus creating as a very efficient long lived pump. This approximate 45 degree rotary caster design can also be used to provide rotary actuation of planar valve assemblies. An important feature of this design is that rotary shaft encoders can be easily attached to the rigid shaft coupling to provide exact information as to which portion of the circular arc contact region is currently compressed—thus facilitating exact control over planar fluid switch connection modes.

Figure 49:
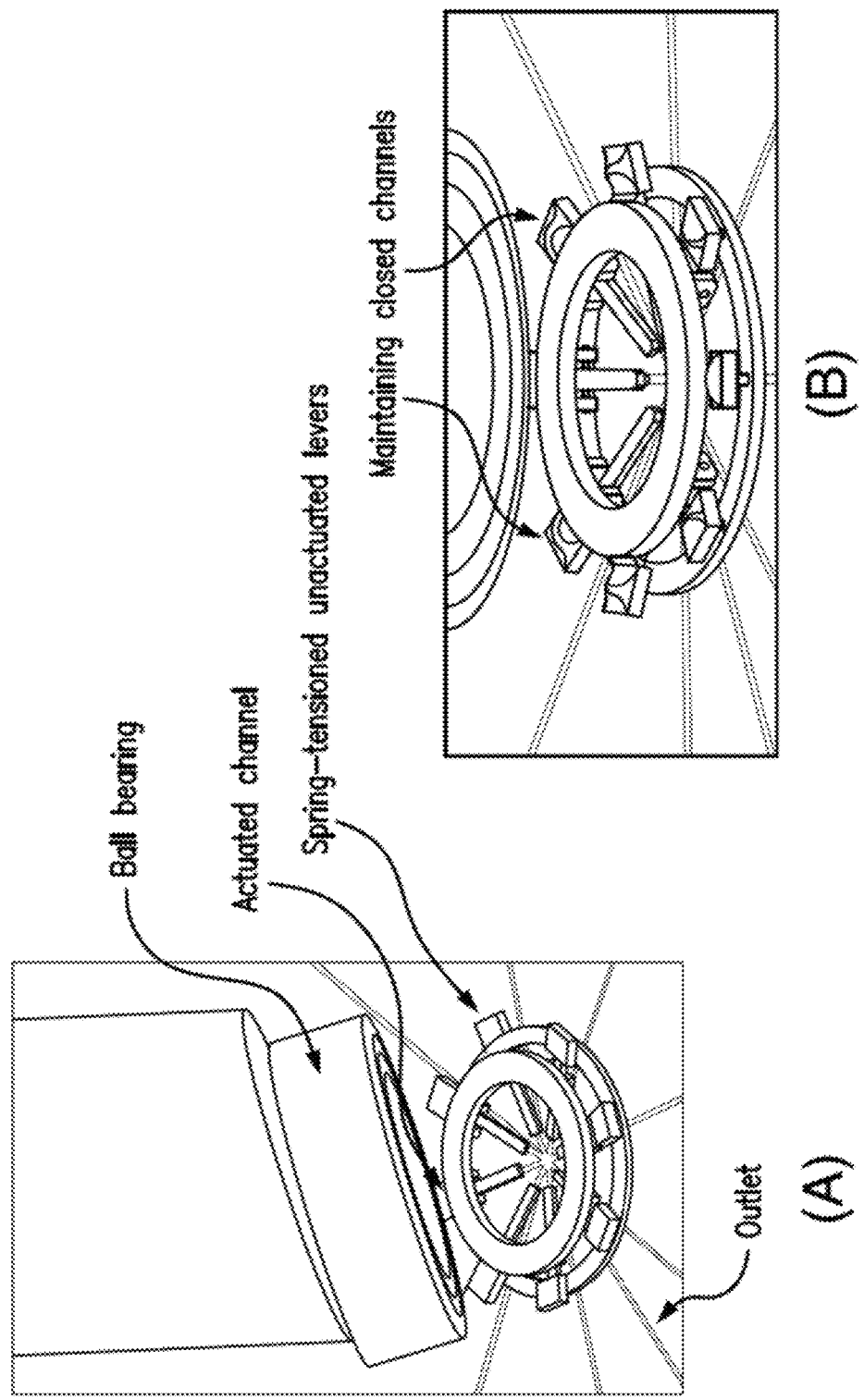

FIG. 49 shows the conceptual design of a spring loaded pressure inverter which is comprised of a rotary array of actuators that can be used to provide a plurality of normally-closed fluidic channel connections which are driven by a central motorized rotary device, such as that illustrated in FIG. 46, or alternatively by any of the ball bearing cage RPV actuators described previously. The device operates on the basis of an embedded or otherwise rigidly mounted fulcrum which can transform the downward pressure associated with a tensioned ball bearing, or roller bearing into an upward force that can open a normally closed microfluidic valve. In this conceptual visualization eight Normally Closed (N.C.) microfluidic valves are located in the central region of the planar assembly.

Figure 50:
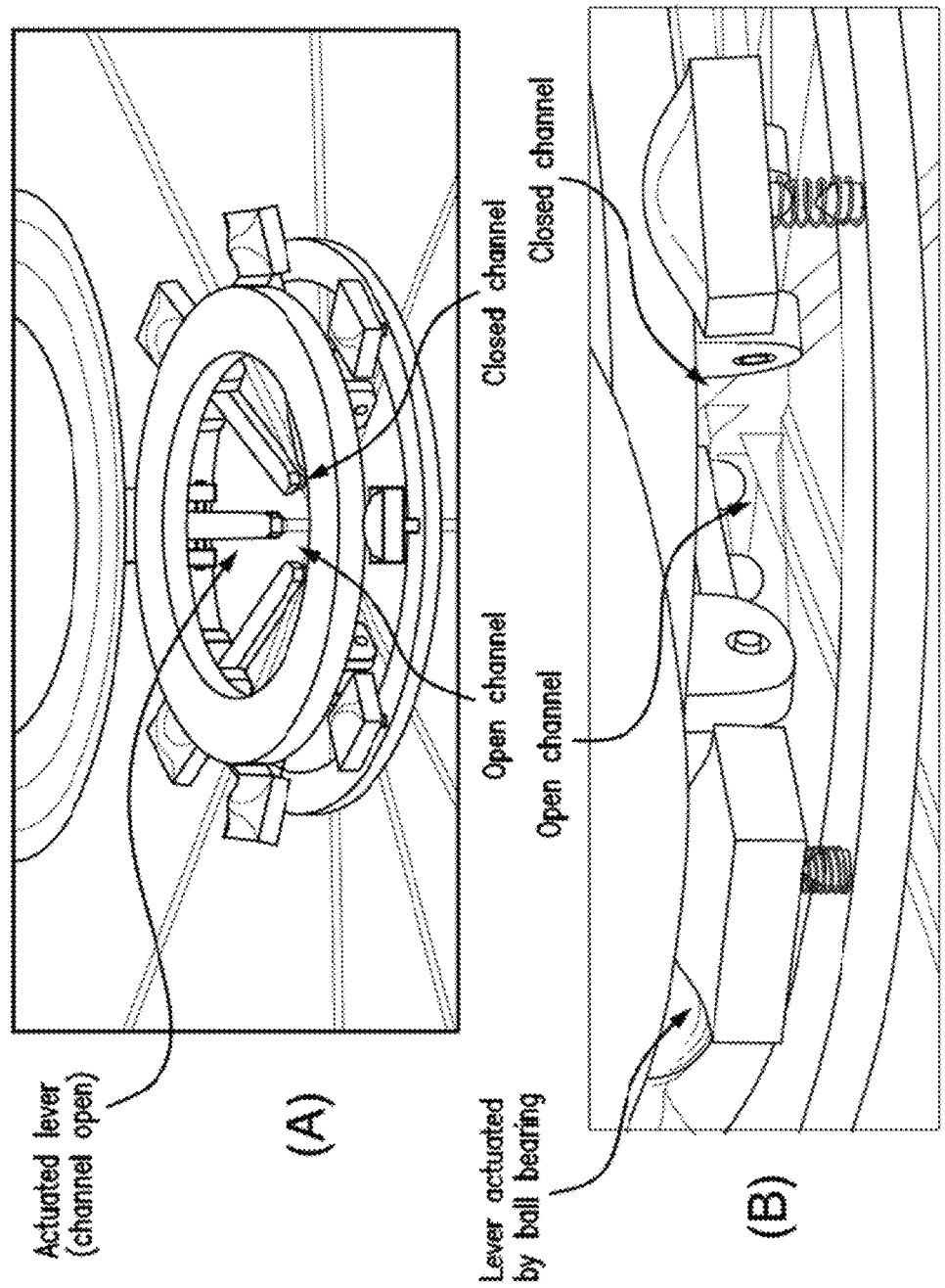

FIG. 50 shows additional views of the conceptual design for a spring loaded pressure inverter actuation device for opening normally closed microfluidic valves. Note that the illustrated conceptual compression springs provide a force which is translated via a fulcrum mounted lever to provide the downward force that keeps a microfluidic channel closed. Only when external force is applied to a lever by a rotary actuator element will the associated microfluidic valve location be opened. Note especially that this is a conceptual diagram, and that actual physical implementation of the assembly might utilize flexible elastomers to provide spring forces and one-piece integrated fulcrum flexure units to act as levers.

DETAILED DESCRIPTION OF THE INVENTION

The present invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term are the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top", may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower" can, therefore, encompass both an orientation of "lower" and "upper", depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about", "substantially" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the invention.

As used herein, the terms, "microclinical analyzer", "microchemical analyzer", and its abbreviation "μCA" are exchangeable.

The description is now made as to the embodiments of the present invention in conjunction with the accompanying drawings. In accordance with the purposes of this invention, as embodied and broadly described herein, this invention relates to perfusion controllers, microclinical analyzers, integrated bio-object microfluidics chips and systems utilizing the perfusion controllers and the microclinical analyzers and applications of the same.

It is naïve to assume that a collection of organs-on-a-chip will exist in a stable equilibrium. Excess metabolic activity of one region without concomitant increases in oxygenation and nutrients will lead to acidification and/or unwanted downstream effects. In living systems, homeostasis is maintained by a plethora of chemical, neural, and biomechanical signals. An organ-on-a-chip system will require an equivalent regulatory system.

The central hypothesis is that humoral factors are critical for maintaining the viability of each organ-on-a-chip. However, the vast majority of the secreted factors and their actions on specific organs remain poorly understood to date.

Figure 1:
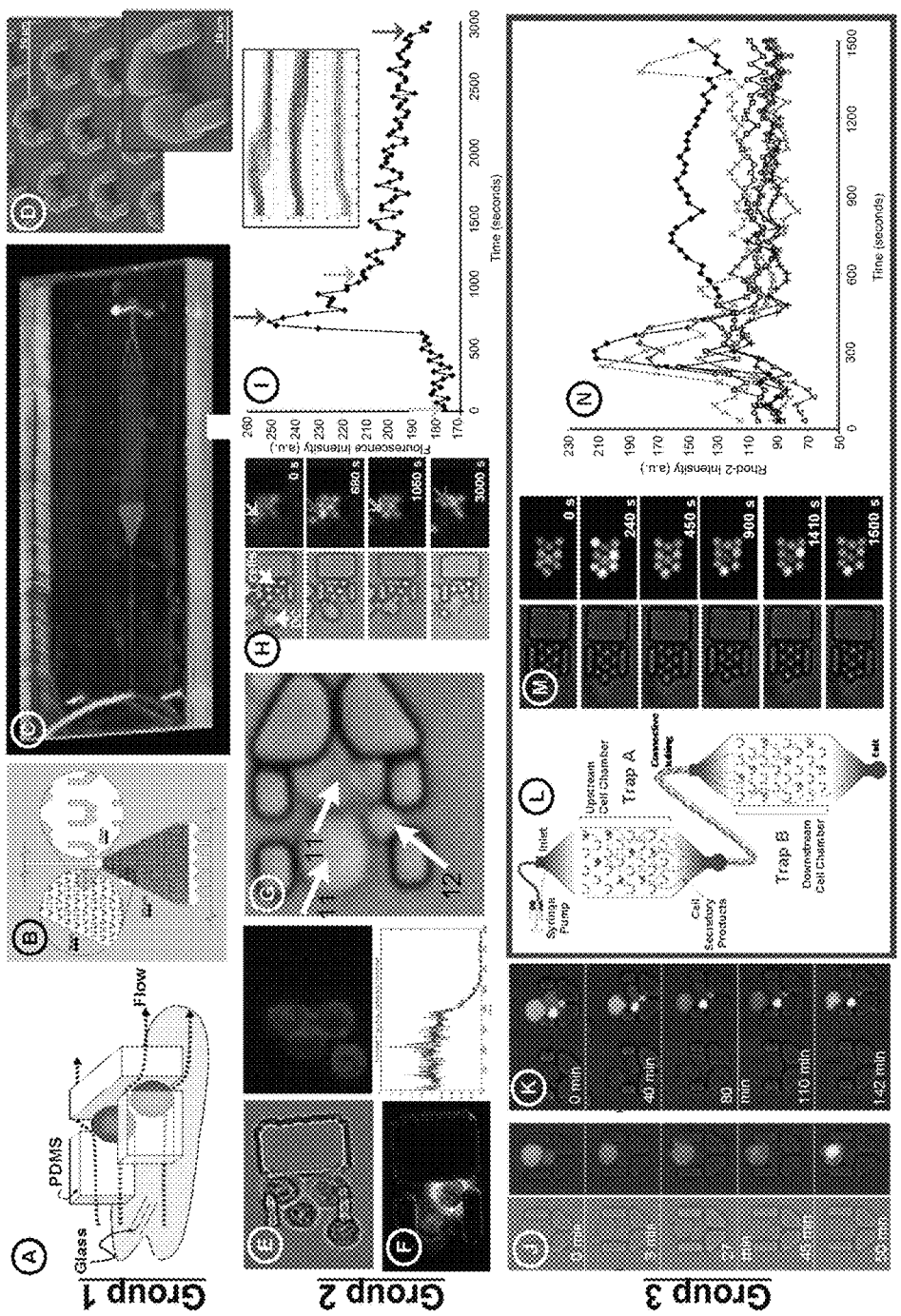
FIG. 1 shows schematically single-cell dynamics and cell-cell communication in VIIBRE (Vanderbilt Institute for Integrative Biosystems Research and Education) Multitrap Nanophysiometers (MTNP). An example of the types of data that can be obtained using living cells in microfluidic chips, and microfluidic chips connected in series. Group 1—MTNP design: (A) Single-trap schematic. (B) Mask layout. (C) Fluoroscein-filled microfluidic channels. (D) Trap SEM. Group 2—T-cell dynamics: (E) Brightfield and fluorescence images of Jurkat cells with quantum-dot marker of IL2 receptor α. (F) Cellular kinetic activity measured by differential video microscopy, with summation of differential images vs. time showing toxin effect. (G) Primary human mature dendritic cells (DC) (red arrows 11) and naive CD4+ T-cells (green arrow 12) in a MTNP. (H) Time-series of brightfield and $Ca^{2+}$ images. (I) $Ca^{2+}$ response by a single, DC-stimulated T-cell, marked by arrows in (H) Inset: automated cluster analysis of 447 ionomycin-stimulated T-cells, identifying three populations that would not have been separated by FACS. Group 3—Dynamic apoptosis assay: (J) Normal and (K) chronic myeloid leukemia (CML) CD34+ hematopoietic stem cells (HSC) exposed to 150 nM dasatinib. In contrast to normal HSCs, the CMLs were drug resistant. Group 4—Non-contact paracrine signaling: (L) Daisy-chained MTNPs with mature DCs upstream and naive T-cells downstream. M) $Ca^{2+}$ activation in downstream T-cells immediately after the two MTNPs were connected. (N) Time course of $Ca^{2+}$ transients from 7 T-cells in (M) demonstrating non-contact paracrine signaling between DCs and T-cells [14, 15].

FIG. 1 shows examples of how soft lithographic microfabrication can be used to create microfabricated devices to study immune cell function. By utilizing this technology to create an artificial lymph node on a chip, it provides an unprecedented opportunity to maintain immune cells with a physiologically realistic rate of media superfusion. The very small volume of the chamber ensures that the neurotransmitters, paracrine and autocrine factors, and metabolites are not diluted and can mimic in vitro the humoral interactions that occur in the body. Extracellular matrix (ECM) can be added to the chambers as required.

Figure 2:
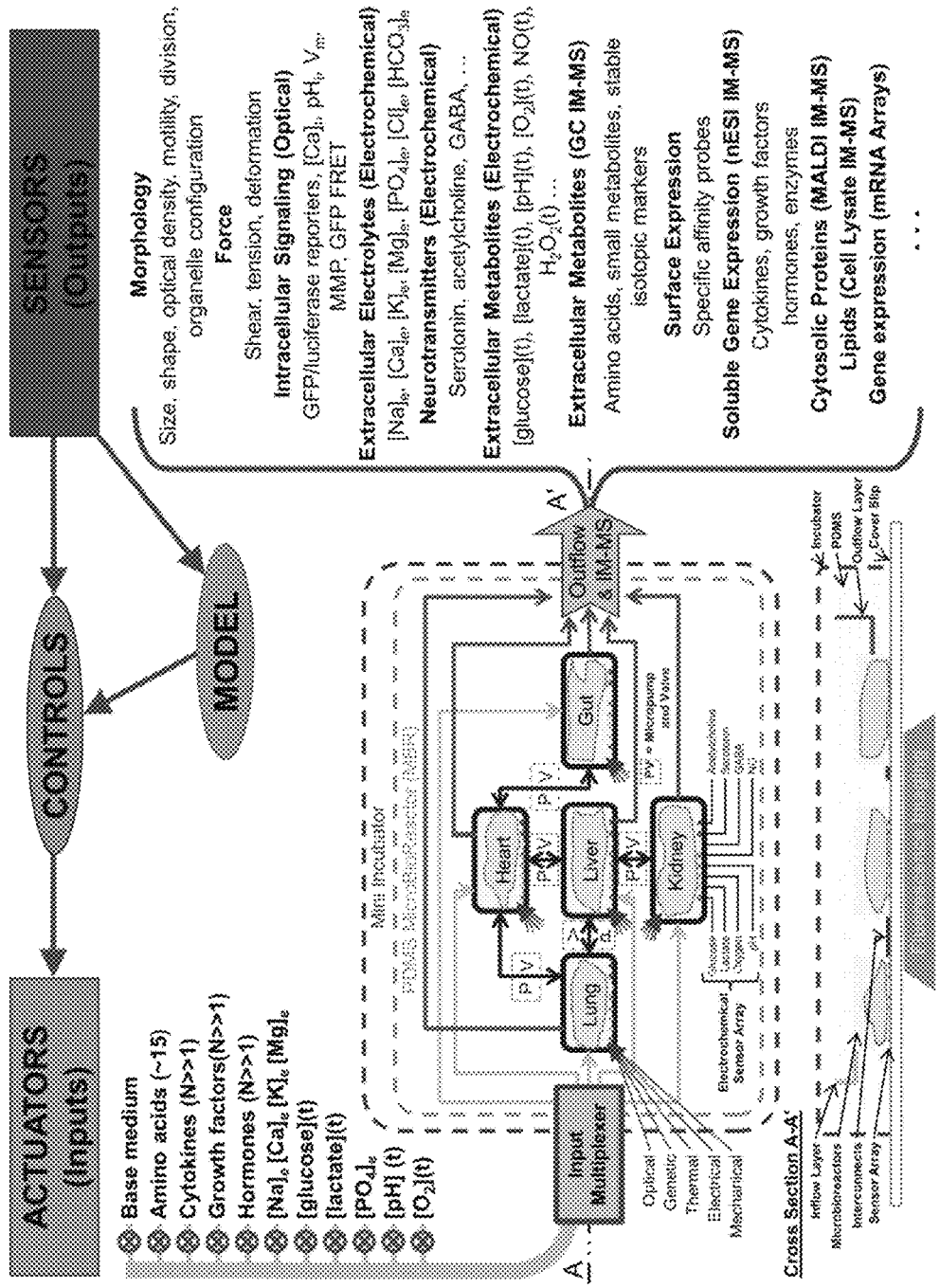
FIG. 2 shows schematically Omni-Omics: a monitoring, control, and diagnostic system for a five-organ-on-a-chip system according to one embodiment of the invention. Each highly instrumented microbioreactor (MBR) or Organ-on-a-Chip allows real-time image analysis and in-chamber fluorescent and electrochemical sensors that provide the control algorithm with dynamic output signals reporting the metabolic and morphological state of the cells under study. A downstream ion mobility-mass spectrometer (IM-MS) provides near-real-time metabolomic and proteomic data from cellular secretions to characterize tissue physiological state and response to drugs and toxins. On the order of a hundred computer-controlled microfluidic valves serve as actuators to deliver control inputs to specific MBRs to dynamically regulate the extracellular microenvironment. Micropumps and valves between chambers control signaling between organs. Optogenetics could be used to extend the control to inside the cell. The systems model would drive the multiple input-multiple output (MIMO) controls that close the loop between the sensors and the actuators, ultimately allowing control over development.

To understand multimodal chemical communication between organs, the invention allows us to study the interactions of different organs as a function of time. The uniqueness of the Omni-Omics approach is shown in FIG. 2. A series of interconnected bioreactors are instrumented and controlled to an unmatched level, providing over 100 simultaneous biological readouts in near real time, and the ability to control, at the same time, dozens of experimental parameters.

With this Omni-Omics system, among other things:
(1) the soluble and bound factors that are produced by the individual organs-on-a-chip can be identified;
(2) the role of individual secreted molecules on organ function can be understood;
(3) the transcriptomic, proteomic, and metabolic changes that arise as a result of exposure to selected drugs and toxins can be quantified;
(4) a high-throughput assay for screening therapeutic agents against the insults listed under (3) can be developed; and
(5) the effects of targeted interventions across various in vitro and in vivo transgenic models can be verified, which opens the avenue for preclinical trials.

The power of this approach is the breadth of dynamic information that is obtained from organs-on-a-chip using mass spectrometric measurements of soluble and bound proteins and metabolites, electrochemical measurements of metabolic activity, optical imaging of fluorescent reporters and cellular phenotype, and of course various omics assays, the most important being transcriptomics, and the ability to control this system with advanced, machine-learning software.

According to the invention as shown in FIG. 2, one can create interconnected, low-volume, microfabricated chambers for each organ; control the fluidic inputs into each chamber so that the outflow of one chamber is the input to another; use electrochemical sensors to measure metabolic activity and state-of-the art mass spectrometry to identify the molecular species in the fluid flowing between the various chambers; use real-time fluorescent imaging of all chambers to characterize cellular and molecular activities within each developing explant; and at the end of each extended experiment conduct extensive characterization of all of the tissues. The miniature pumps and valves disclosed in the invention allow us to control drug and chemical delivery to each chamber.

Bioreactors: Microfabricated bioreactors (MBRs) offer the unprecedented opportunity to maintain tissue explants in a close-to-physiological environment [56], wherein the extracellular volume and fluid interconnectivity between brain regions are sufficiently well controlled to study paracrine and autocrine signaling phenomena. We will use standard microfabrication technologies for polydimethylsiloxane (PDMS) or other polymers or materials to construct an interconnected network of five or more bioreactors, each of which will maintain a small explant from the brain of a developing mouse. Each MBR will be designed to allow us to record hundreds of biological parameters from each brain region we are studying, including, but not limited to, those shown in FIG. 2. Cellular microbioreactors are routinely fabricated in the laboratory, and the existing designs can be readily adapted for the proposed experiments with brain explants. Most important, the flow rates utilized to maintain tissues in small MBRs are well matched to the flow rates of nanoelectrospray, ion mobility-mass spectrometers (nESI-IM-MS) (100-500 nL/min), so that we can sample the fluid being exchanged between organs with time resolutions of one minute. The low cost and small size of these reactors will let us study many MBRs in parallel using a microfabricated multiplexer.

Analysis: The interconnecting chambers allow us to sample the humoral factors with nESI-IM-MS. Beyond this, we also have the capability to examine the molecular distributions within organs with a wide variety of methods (MALDI-IM-MS, transcriptome profiling, etc.). Selected reaction monitoring (SRM) with mass spectrometry will allow us to track the changes of molecules that demonstrate the most differential activity between the five regions studied. Other methods of analysis are depicted in FIG. 2.

Ion Mobility-Mass Spectrometry (IM-MS): Many important questions about cell signaling, cell-matrix interactions, and metabolomics defy current analytical instrumentation and controls. Real-time measurement is critical for biological system control. In particular, the simultaneous high-frequency dynamic measurements of protein expression and the generation of metabolites and other signaling molecules exceed current capabilities. For example, normal mass spectrometry (MS) of tissue or the media from cell culture or tissue perfusion would detect a large number of isobaric species that could not be differentiated solely upon mass-to-charge ratio (m/z). High performance liquid chromatography (HPLC) can separate isobaric species through an interaction with a chemically selective stationary phase tailored for particular analytes (e.g., hydrophobic or hydrophilic), but a single HPLC separation can require an hour or more, and this precludes real-time control of the system while probing metabolic dynamics.

The biggest problem with the application of mass spectrometry to a large collection of organs-on-a-chip is that it takes 30 minutes to an hour for a single HPLC run, depending upon the separation column utilized. This means that one can sample each organ two to four times a day in a 10-organ system. If one wants to track four 10-organ experimental platforms, one needs to analyze 40 cuvettes a day and is able to read out each organ only once a day. For a one month pharmacokinetics/pharmacodynamics run, one acquires a large number of cuvettes, requiring a large number of LC columns and lots of MC time.

There are advantages to stop-flow collection of a single organ at a time so that the metabolites and biomarkers being tracked are concentrated. Off-line analysis requires that the collection of larger volumes can be stored and handled (a microliter is a small amount of fluid in the bottom of a cuvette). This creates a growing backlog of cuvettes to analyze, at 30-60 minutes each. The alternative enabled by these inventions is to utilize a perfusion controller that controls external sample collection directly into microfluidic tubing connected to a mass spectrometer.

Figure 3:
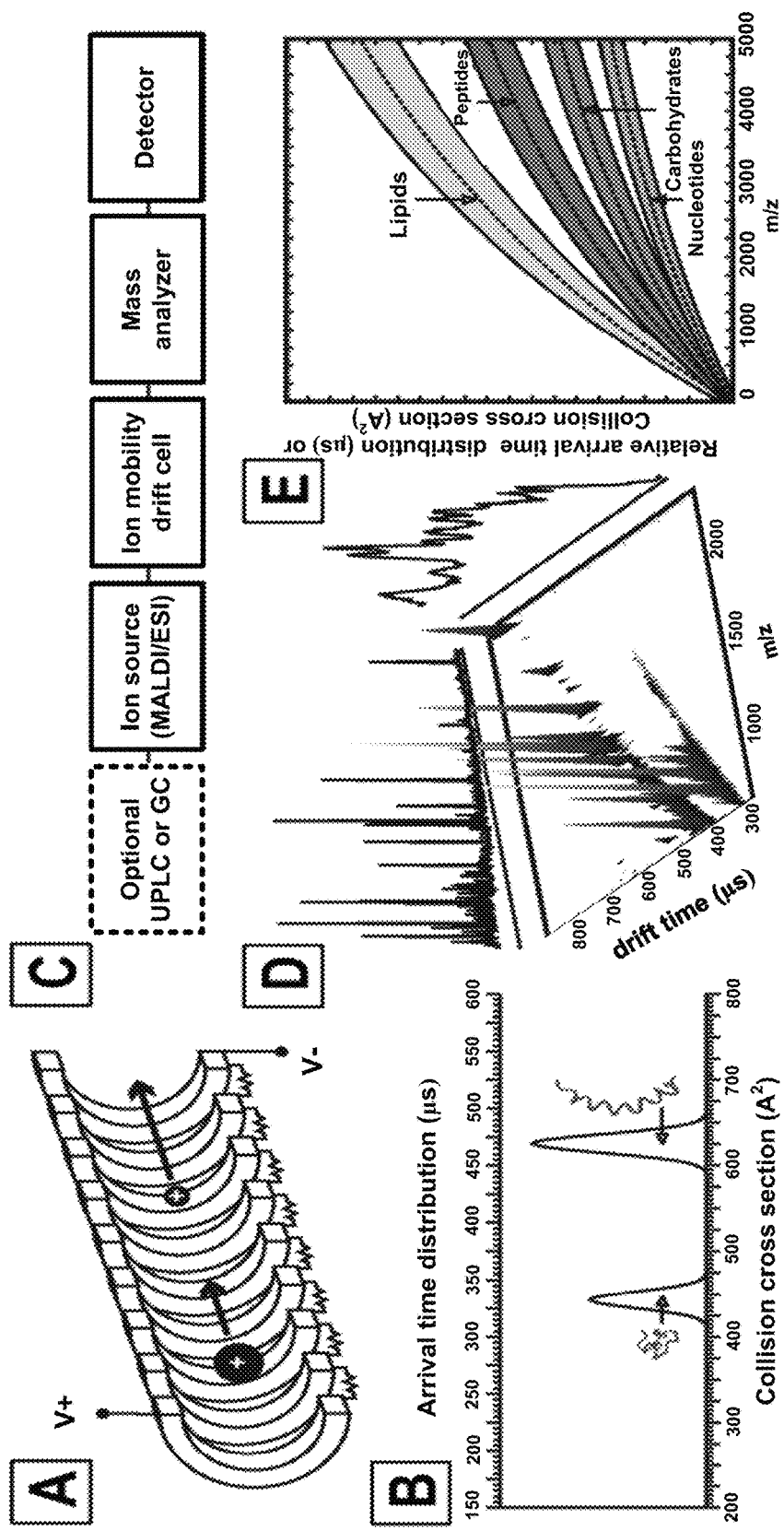
FIG. 3 shows schematically Ion Mobility-Mass Spectrometry (IM-MS). The chemical communication between different organs in a multi-organ-on-a-chip system can be studied using IM-MS. (A) The principle of an IM drift cell: a stack of ring electrodes creates an electric field gradient that supports gas phase electrophoresis. (B) A hypothetical IM separation for peptide ions exhibiting two distinct structural sub-populations corresponding to globular (left) and to helical (right) conformations. The observed arrival time distribution (ATD) data (top axis), can be transformed to a collision cross-section profile (bottom axis). (C) IM-MS block diagram. (D) 3D MALDI-IM-MS conformation space plot for a complex protein digest, showing projections of the mass spectrum without IM (back) and the electropherogram (right) to the right with IM alone. (E) A theoretical depiction of where singly charged analytes of different molecular classes are observed in IM-MS conformation space, providing the basis for simultaneous omic experiments with minimal sample pretreatment and purification [3-13].

As a major innovation in mass spectrometry for understanding the physiology of coupled biological systems, a collaboration between the Wikswo and McLean groups at Vanderbilt, the Lipson group at Cornell, and Vallabhajosyula at CFDRC is applying symbolic regression [1], machine learning [2], electrochemical [3] and optical sensing, and nanoelectrospray and MALDI ion mobility-mass spectrometry [4-24] to infer the equations underlying metabolic and signaling dynamics [25-29], ultimately to control biological systems [29, 30]. Ion Mobility-Mass Spectrometry (IM-MS), the keystone technique in this omni-omics effort, utilizes a post-ionization gas-phase electrophoretic separation on the basis of structure prior to m/z determination. This technology enables three-dimensional separations (analyte structure, mass-to-charge, and signal intensity) to be completed on a timescale of milliseconds [4, 6, 7, 31-38]. The details of the IM-MS approach are shown in FIG. 3.

Another reason for high-speed mass spectrometer analysis is to allow multiplexing of the analysis of effluent from a large number of different organs individually sampled at a much lower rate. But to obtain speed, one needs to desalt without waiting for a standard LC separation that does not require desalting. The invented perfusion controller and microclinical analyzer can readily include on their outputs modules that would provide on-line desalting, for example with a one-minute desalting process for a 100 nL sample feeding directly into the nanoelectrospray (nESI) port on a Waters Ion Mobility-Mass Spectrometer (IM-MS). The great feature of IM-MS is that the IM gas-phase electrophoresis structural separation accomplishes in 1 ms what HPLC can do in 60 minutes and UPLC can do in 30. The bandwidth increase of five orders of magnitude is reduced by a factor of about 50 by the time required to desalt, but the advantage of this approach is that the 1 minute desalting might allow one to look at every organ in a 10 Cartridge Experimental System once every 10 minutes. Alternatively, rapid desalting might be possible by using a miniature microdialysis desalter.

Advanced Microfluidic Systems for Cellular Control: According to the invention, one can exploit the capabilities of microfluidic devices to provide restricted dimensions to localize small cell populations; low flow rates; a high ratio of cell volume to media volume; the ability to rapidly change media; and proximity of in situ, in-line, and downstream sensors. The development of compact, low-cost, and easy to use microformulators allows rapid changes to the relative concentrations of up to 16 different chemical reagents in the media superfusing the cells under study.

Figure 4:
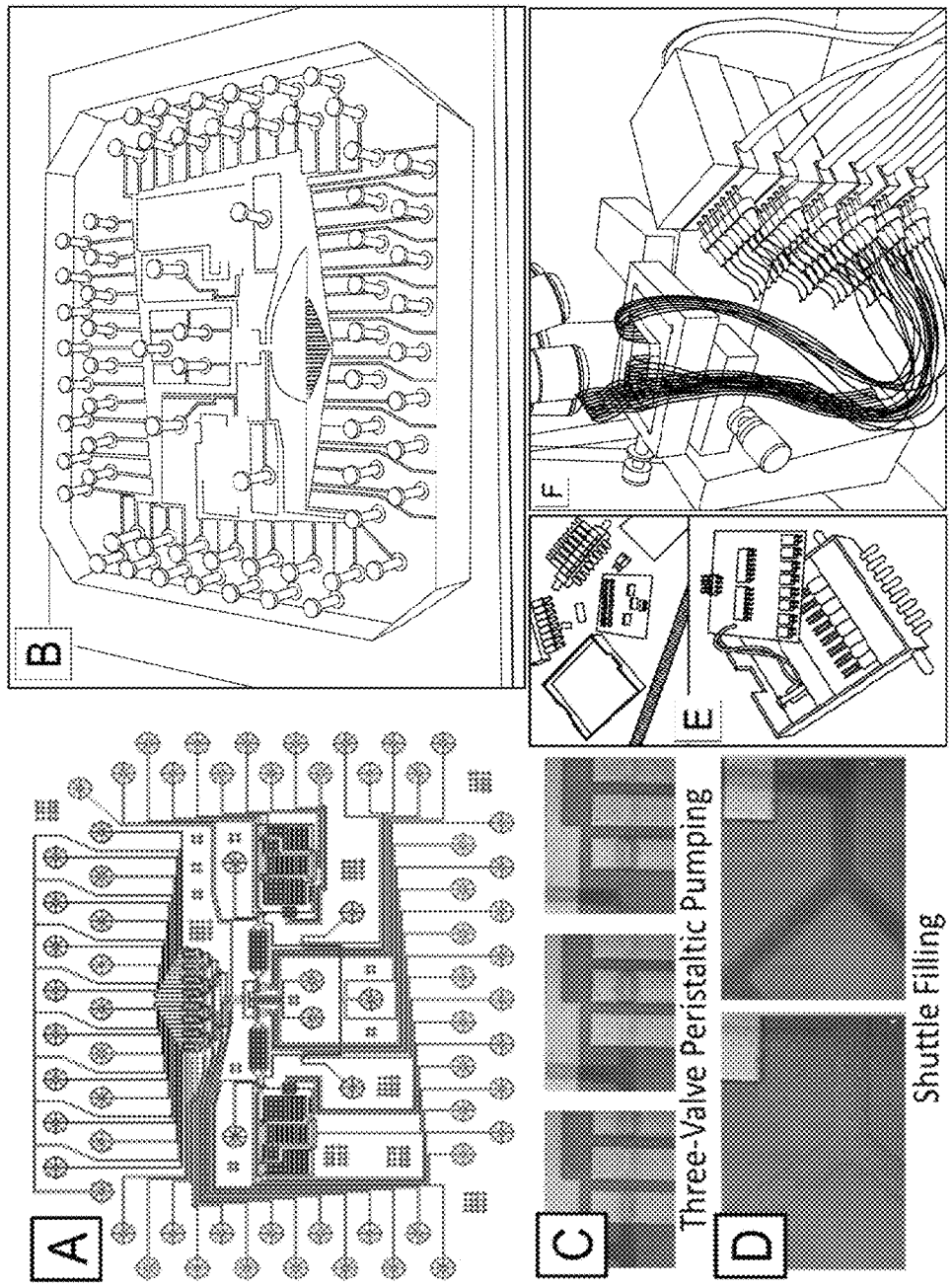
FIG. 4 shows schematically a Microformulator for real-time preparation of Organ-on-Chip perfusion media. The real-time control of the chemical make-up of a micro-organ perfusion system requires the formulation of very small volumes of precise mixtures of custom perfusate prepared in real time in response to the changing physiological states of organs in the system. This system shows the pneumatically controlled microformulator. (A) AutoCAD layout of the microformulator based on the design of Hansen et al. [1, 2], but capable of assembling and mixing a larger volume of fluid. The device has 45 control channels, shown in red, and 16 fluid inputs, shown in blue. (B) Functional microformulator. (C) Valve actuation in the device. (D) Peristaltic pumping. (E) and (F) The custom solenoid valve banks.

Microformulators for MIMO Bioreactor Control: The ability of biologists to control temporally the chemical and fluidic environment around adherent or suspended cells in vitro is limited by the available technologies: bulk fluid changes, possibly including centrifugation and resuspension; peristaltic and syringe pumps; manual and multihead pipettes; and fluid-handling robots. The speed with which each approach can change the fluid environment is limited, and the required instruments can be costly and quite bulky. Microfluidic devices have proven useful for studies of chemotaxis and cell-cell interactions, but these devices often utilize either multiple syringe pumps costing $2,000 or more each [39-47], or on-chip peristaltic pumps that require precise microfabrication, multiple solenoid valves, and an external source of pressurized gas at a cost of about $500 per pump [48-50]. Hence biologists seldom have the ability to simultaneously control the concentrations of multiple chemicals, a MIMO prerequisite. Hansen and Quake accomplished this with a microformulator for protein crystallization, albeit with an 80 pL stroke volume, a five nL mixer and a ten nL/min flow rate [51-53]. FIG. 4 shows VIIBRE's implementation of this approach, but designed to have a 160 pL stroke, a 0.5 µL mixer, and 0.5 µL/min flow rate— matched to typical VIIBRE microbioreactors and the nESI-IM-MS. However, chip and tubing complexity and size and the fabrication cost of the solenoid valve controller in FIG. 4F (about $6,000) limits the use of this technology.

Figure 5:
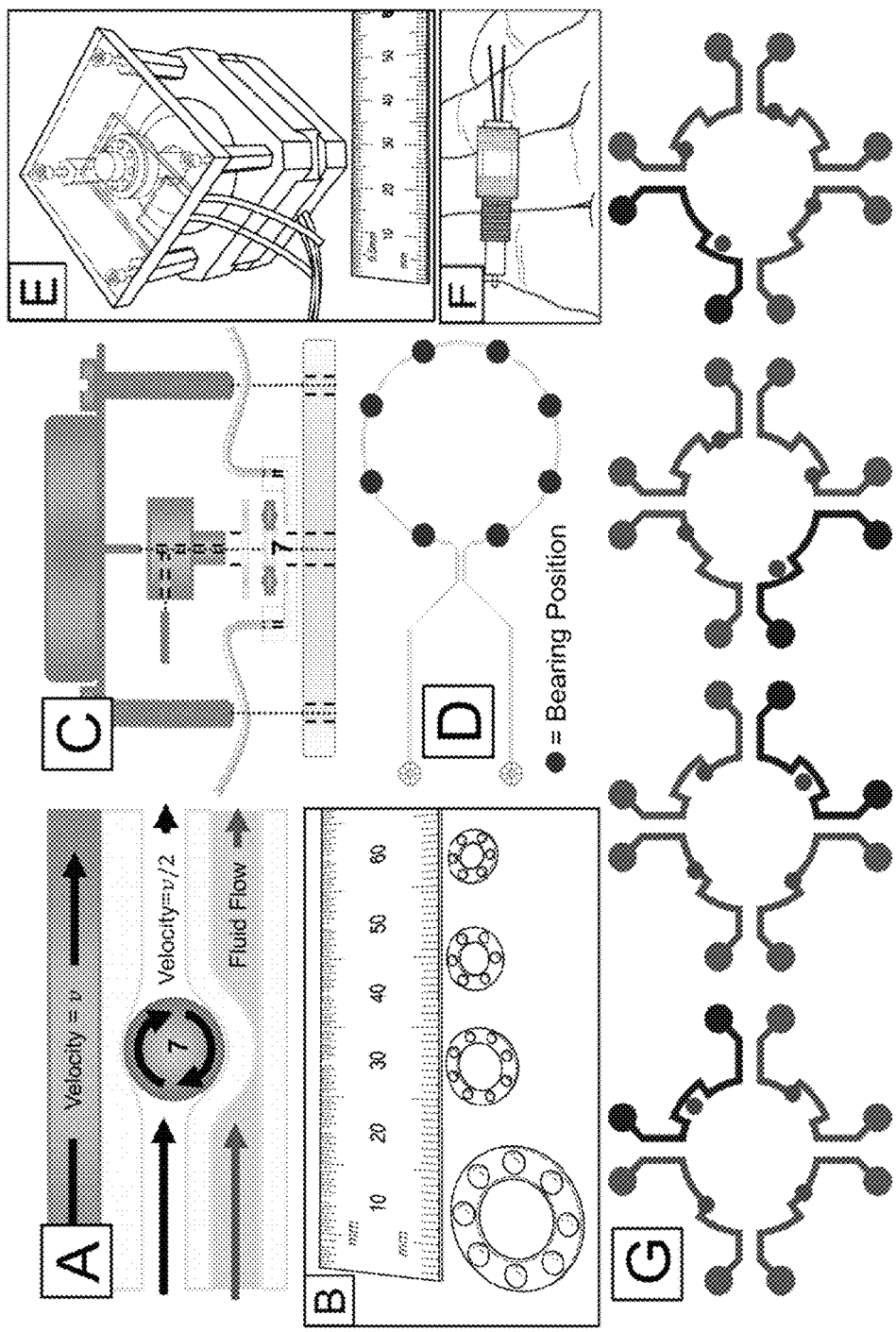
FIG. 5 shows schematically a Rotary Planar Peristaltic Micropump (RPPM) and Rotary Planar Valve (RPV) according to embodiments of the invention. (A) A schematic of fluidic flow generated by rotatably moving the ball bearing 7 on the fluidic channel. (B) Actuators with ball bearings. (C) A schematic of a motor head with an actuator. (D) A schematic of a RPPM. (E) A stand-alone peristaltic pump having stepping motor and microcontroller controller and pump cartridge. (F) A miniature gearhead of the stepping motor connected to a miniature RPPM. (G) A schematic of channel layout for a RPV that selects one of four channels by a 15° rotation.
Figure 6:
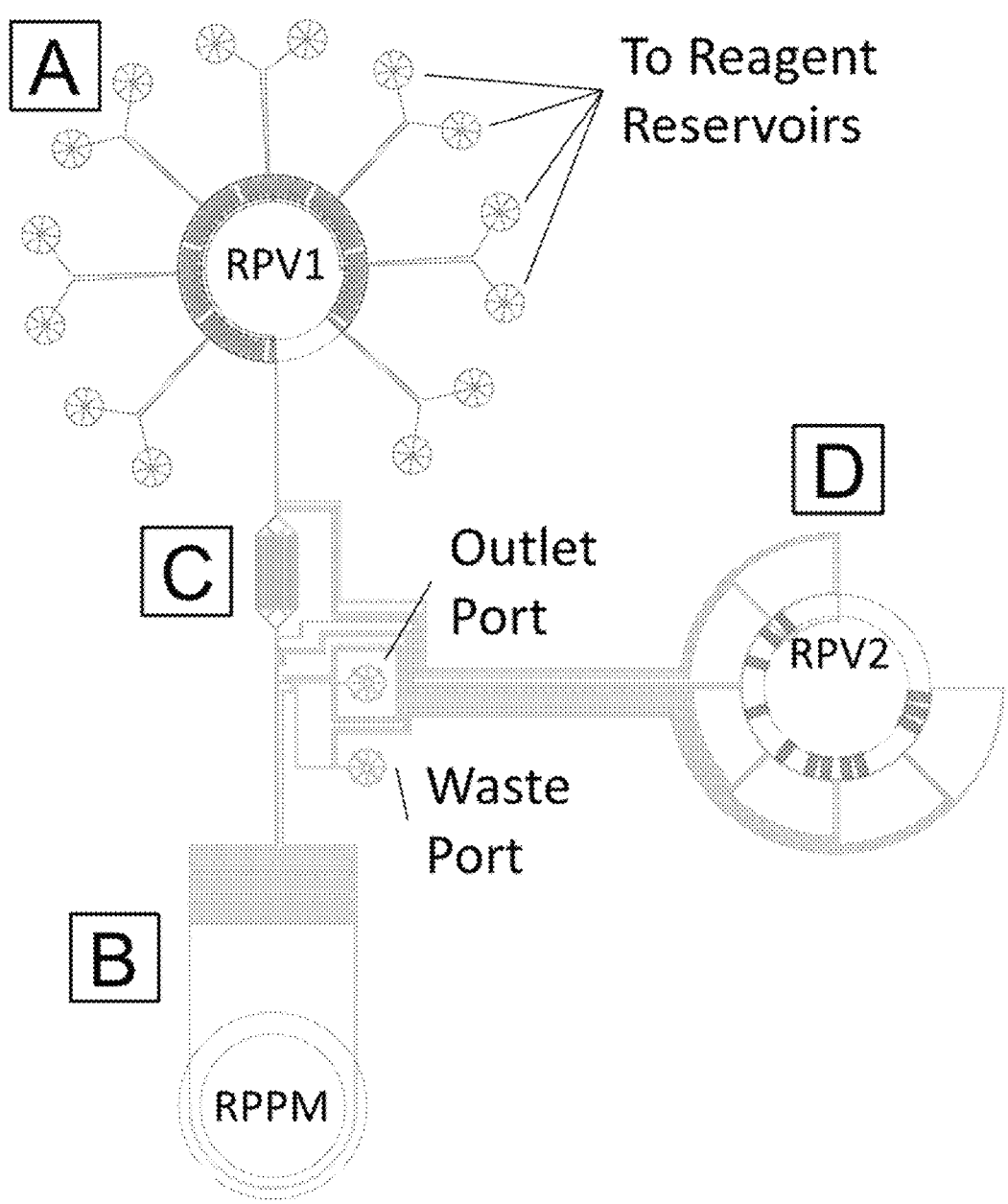
FIG. 6 shows schematically the RPPM-RPV batch-mode microformulator. A fourteen-port RPV1 (A) selects the reagent to be drawn from one of 14 reservoirs by the RPPM (B) to load the shuttle (C). RPV2 (D) controls washout, loading, mixing, and delivery of custom solutions.

The inventors introduced a new on-chip peristaltic pump that requires purchase of only a miniature geared stepping motor (about $200) and a controller (about $100) but was somewhat labor intensive to fabricate (about 1 person-hour pump) [54]. This led the inventors to invent an entirely new class of rotary, planar peristaltic micropumps (RPPMs), as shown in FIG. 5. At about $20 to $45 per channel, they cost at least an order of magnitude less than commercial instruments used for precise temporal control of biological fluids [55]. These are precise, easy-to-use pumps. The simple motor/thrust bearing geometry developed for the RPPM also enables a new class of rotary planar valves (RPVs) as shown in FIG. 5, which cost $1 to fabricate and whose motor and controller cost about $90. One RPPM and two RPVs can be combined to create a simple microformulator, as shown in FIG. 6, for $1/20^{th}$ of the cost of the valve controller in FIG. 4F. This will deliver on-demand custom solution mixtures as required for MIMO microenvironmental control.

Modeling and Control: Real-time control of a quantity requires its measurement in real time. Measurement of acidification alone is not sufficient, and it is necessary to measure in addition glucose, oxygen, and lactate fluxes to understand core carbon metabolism. But organ metabolism also involves the secretion and consumption of a plethora of other biological molecules. Current analytical capabilities cannot provide the needed simultaneous measurements of protein expression, metabolites, and other signaling molecules generated by cells. Ion Mobility-Mass Spectrometry (IM-MS) offers the potential to be the next transformative systems biology technology. IM-MS yields five orders of magnitude increase in systems throughput over liquid-chromatography mass spectrometry (LC-MS) by utilizing a post-ionization gas-phase electrophoresis separation on the basis of structure prior to m/z determination [4, 6, 7, 31-38]. Nano-electrospray ionization (nESI), matrix-assisted laser desorption ionization (MALDI), ultraperformance liquid chromatography (UPLC), or gas chromatography (GC) provide IM-MS inputs.

Figure 7:
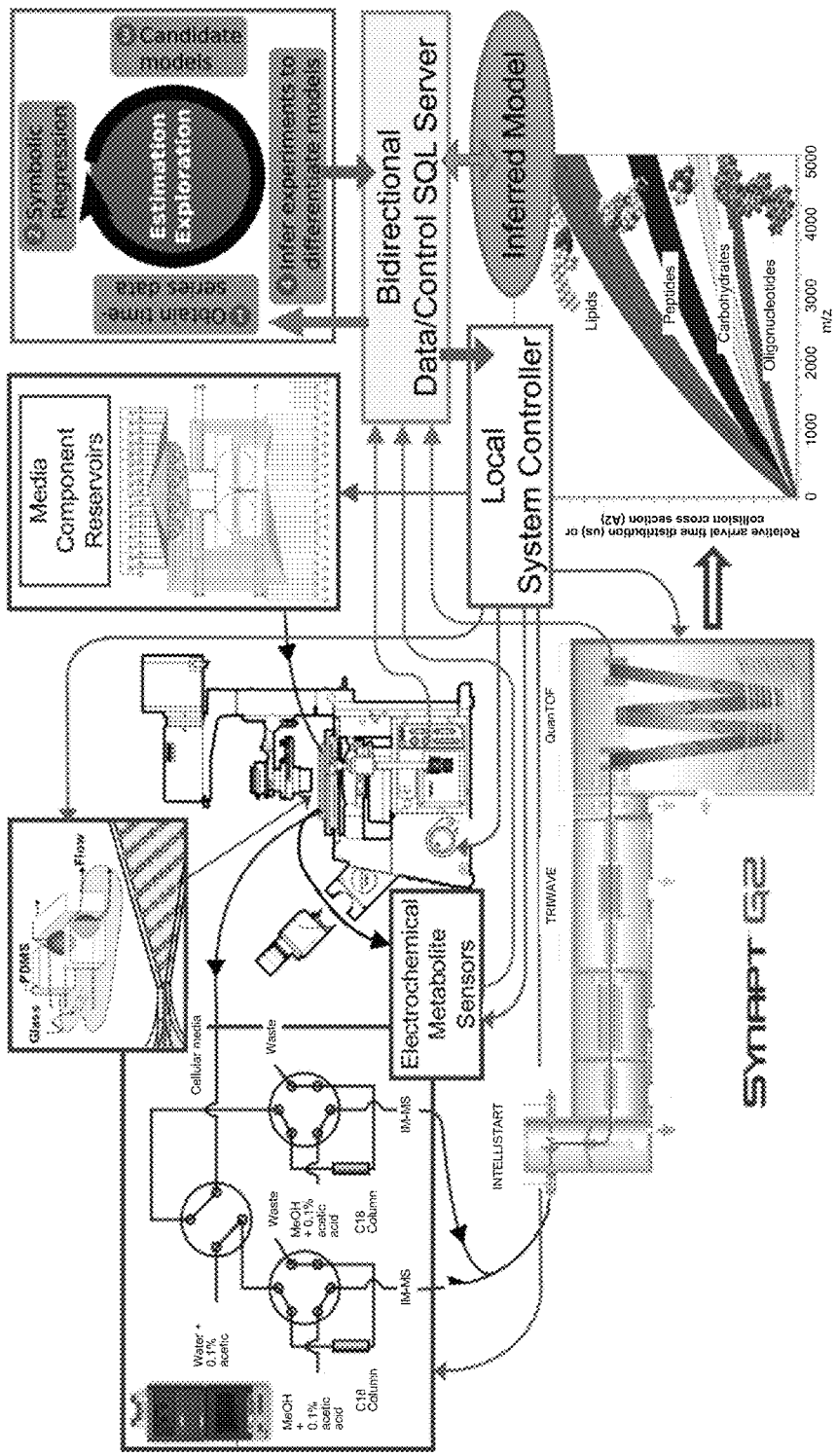
FIG. 7 shows schematically the Omni-Omics automated biological explorer. A computer-controlled microformulator (A) prepares in one minute a μL of custom culture media delivered to cells (B) in a multitrap nanophysiometer (MTNP) on a fully automated inverted fluorescence microscope (C). The MTNP effluent is delivered to glucose, lactate, oxygen and pH electrodes (D) and to an automated pump (E) and affinity-column desalter (F). The desalted media, which can upon command include cellular lysate, is introduced by nanoelectrospray to an ion mobility-mass spectrometer (G). All instrument functions are under local computer control (H), and data are passed to a real-time SQL server (I). Computer algorithms (J) evaluate about 1000 candidate models and in silico experiments for each experiment design that is passed back to the real-time SQL server (I) for implementation by the local computer control (H). The inferred model (K) is updated for immediate access by on-line investigators and for system control.

The Omni-Omic Automated Biological Explorer, shown in FIG. 7, is providing us with unprecedented ability to study cellular signaling and metabolism of small cell populations, and is moving towards computer-guided, closed-loop control of the experiments. The inventors have already demonstrated in silico that the exploration/estimation and symbolic regression algorithms can infer metabolic models with no a priori information [29]. Using this approach to develop the equations for real-time control of the microbioreactors, and eventually, analytical models, will allow us to alter the cellular microenvironments to positively affect neural development. This system is ideally configured as a diagnostic platform for organ-on-a-chip assay development. Most important, this system is capable of being run remotely, i.e., of laboratory telescience that will allow toxicologists at one location to conduct diagnostic tests on bioreactors at another.

For the purpose of this invention of a perfusion controller and a microclinical analyzer, there are a number of basic module definitions required to understand the central role played by both the perfusion controller and the microclinical analyzer for culturing, maintaining, and studying a collection of interconnected organs-on-a-chip.

Organ-on-Chip Module (OoC): Each synthetic organ needs to be housed in a disposable microfluidic cell growth and incubation chamber. These chambers can vary in design to accommodate the particular needs of the cells comprising the organ, but the overall footprint of each Organ-on-Chip will be standardized to accommodate insertion into the various support and interrogation modules which allow multi-organ drug and pathogen interactions to be studied.

Organ Cartridge for cellular Instrumentation and Support: These cartridges could have a standardized overall footprint, but contain customized support microfluidics, pumps, electronics, valving and instrumentation modules appropriate to each individual organ type. Each cartridge is designed to accept a disposable Organ-on-Chip module which has been pre-conditioned in an Organ Farm or Organ Incubator and each cartridge has provisions for easily inserting the module in a sterile manner. In a similar manner, these standardized Instrumentation/Support cartridges are designed to accommodate sterile insertion of the Organ Cartridge into a larger assembly known as the Multi-Organ Experimental Platform or Cartridge Dock which supports many individual Organ Cartridges and provides the environment for multi-organ experiments.

Cartridge Dock: This is a multi-unit support module which can be used to provide control of temperature and continuous-flow nutrient supply to many individual disposable Organ-on-Chip modules housed within their respective Organ Cartridges. It will be used to provide the appropriate growth sequences necessary to generate the mature biological tissue arrays to mimic individual organ types. The Cartridge Dock and/or the Organ Cartridge provides facilities for initial loading of cells into pre-sterilized Organ-on-Chip modules and includes provisions for inserting or disconnecting one module without compromising sterility of adjacent modules. This system has a standardized interconnect system which can accommodate the most complicated as well as the least complicated Organ Cartridge module. The Cartridge Dock is controlled by a stand-alone computer-based control system that provides organ-specific flow of nutrients, appropriate valving, and recording functions that identify the history of individual Organ-on-Chip modules. The Cartridge Dock is stored in an incubator or Organ Farm, which provides the desired ambient temperature and humidity. A master experiment control computer provides the control signals that establish valve and pump control conditions to fluidically connect individual Organ Cartridges to other Organ Cartridges within the Cartridge Dock and maintain physiological health of the tissues. In addition the Master Control Computer (MCC) is responsible for periodic calibration of the electrochemical sensor arrays and controls the valving and pumping operations which are required to perform electrochemical measurements, and to dispense fluids for external analysis.

Master Control Computer: This is the dedicated system which controls all operational aspects of the Multi-Organ Experimental Platform. In an initial, exemplary implementation, this system operates as a simple interpreter that performs sequential operations of valve activations, pump parameter activations, electrochemical sensor calibration, and measurement sequences and fluid dispensing and drug injection sequences according to a pre-set protocol list of operations loaded into the instruction queue by the scientists designing the multi-organ experiment. During the experiment the MCC records detailed time-stamped confirmation of each sequential activity and it acquires all experimental measurement data from electrochemical sensors and from the computer actuated microscopes. The Master Control Computer may rely on secondary microcontrollers to perform time critical or compute/bandwidth intense operations such as microscope camera focusing or high speed repetitive microstepping operations. Advanced techniques of sensor feedback controlled operation could be investigated at later stages of instrumentation development via dynamic modification of the experiment protocol list. The master control computer can communicate with secondary microcontrollers either by a hard-wired connection or by means of a digital wireless communications protocol.

Referring to FIGS. 38 and 39, two Organ Cartridge systems are shown according to certain embodiments of the invention. The invented organ cartridge is used to control an Organ-on-a-Chip and illustrates the basic relationships between the various subsystems that define the Organ Cartridge system. The two Organ Cartridge systems are essentially the same, except that the Organ Cartridge shown in FIG. 38 does not include the microfluidic interstitial or microvasculature space. The Organ Cartridge includes a mechanical controller (MC) that senses electrical, mechanical, or fluidic signals and applies either pneumatic or mechanical stresses to the Organ Chip (OC). The perfusion controller (PC) contains the pumps, pressure sensors and microfluidics for perfusion, sample collection, drug delivery, and waste disposal. The MicroClinical analyzer (μCA) can utilize a commercial, low-cost, screen-printed electrochemical electrode array connected to a multichannel multipotentiostat to make regular measurements of glucose, lactate, pH, and oxygen to track organ metabolic activity and health. For systems with two compartments, e.g., an interstitium, there will be parallel PCs and μCAs for each compartment. The microvasculature and microfluidic interstitium are disposable interconnects that may incorporate the discrete tubing shown interconnecting the various components. The underlying support systems include a Master Electronic System Controller, a Microscope, a Fluid Supply for nutrients, drugs, etc., a Gas Supply for $O_2$, $N_2$, $CO_2$, etc., a Waste line, a means for Sample Collection, and an Environmental Controller that adjusts $O_2$, $CO_2$, humidity, temperature, etc. The fluid bus contains both the arterial and venous systems and other fluids, e.g., nutrients, drugs. The gas supply will deliver $O_2$, $N_2$, $CO_2$, etc. The small connecting tubing will in fact be in the form of custom interconnects. Electrical wiring will use a cartridge electrical bus that connects to the Multi-Organ Experimental Platform.

Specifically, the integrated bio-object Organ Cartridge has at least one bio-object chamber for accommodating at least one bio-object, at least one perfusion control unit coupled to at least one bio-object chamber for selectively perfusing the at least one bio-object with one of the plurality of fluids, at least one microclinical analyzer coupled to the at least one perfusion control module for analyzing an effluent of the at least one bio-object responsive to the perfusion, a microcontroller coupled to the at least one perfusion control module and the at least one microclinical analyzer, and a chip carrier for accommodating the at least one bio-object chamber, the at least one perfusion control unit, at least one microclinical analyzer and the microcontroller. The carrier comprises a plurality of fluidic paths for connecting the at least one inlet, the at least one outlet, the at least one bio-object chamber, the at least one perfusion control unit, and at least one microclinical analyzer to define a fluidic network.

In one embodiment, the integrated bio-object chip Organ Cartridge includes a mechanical controller for sensing strain and applying either pneumatic or mechanical stresses to the at least one bio-object chamber.

Further, the integrated bio-object chip Organ Cartridge could in some embodiments include a microscope coupled to the at least one bio-object chamber.

Additionally, the integrated bio-object chip Organ Cartridge also has a support system having at least one fluid unit coupled to the at least one bio-object chamber and the at least one perfusion control unit for providing the perfusion fluids, a gas supply unit coupled to the at least one perfusion control unit, and a waste unit coupled to the at least one perfusion control unit for exhausting the effluent of the at least one bio-object.

Moreover, the integrated bio-object chip cartridge includes a sample collection unit coupled to the at least one perfusion control unit.

In one embodiment, the integrated bio-object chip cartridge further has an environment control unit designed to provide an appropriate physiological environment to at least one bio-object.

In another embodiment, the integrated bio-object chip Organ Cartridge also has at least two individual flow channels that connect with the at least one perfusion control unit, where one of the at least two individual flow channels is adapted for an efferent flow, while the other of the at least two individual flow channels is adapted for an afferent flow.

These examples highlight many of the absolutely essential topological features of functional connectivity between subsystems required for successful Organ Cartridge design. Several of the most important aspects of the perfusion controller as it relates to the Organ Cartridge design apparent in this exemplary drawing are outlined below:

(1) The spatial arrangement of Organ Cartridge subsystems and their controls must be compact.
(2) Fluidic paths must be carefully designed to provide appropriate physiological tissue support functionality while at the same time providing low dead volume connectivity so that the built-in microclinical analyzer chip can detect target molecules with maximum sensitivity.
(3) The microscope subsystem must have unhindered access to the organ incubation chamber and a clear path must exist for transillumination of the Organ Chip to allow label-free microscopic observation of organ tissues.
(4) Mechanical control features must be tightly coupled to the Organ Chip for those tissues which require such stimulation.
(5) The perfusion control system is central to the design and must be able to provide all the necessary fluidic path adjustments and volume modulations required to maintain tissue viability and on-chip chemical concentration measurements.
(6) The fluidic support system must include provisions for supplying appropriate fluids, gases, and waste solution pathways required for long-term viability of organ tissues within the Organ Chip supported by the Organ Cartridge. The disposable Organ Chip unit must be co-engineered with the support system modules to allow precision alignment for "plug-in" attachment. The Organ Cartridge is also semi-disposable, but the Organ Chips essentially must be disposable.

FIG. 40 shows a schematic diagram that illustrates several important aspects of how different types of individual Organ Cartridges are interconnected in a Cartridge Dock to provide a multi-organ system. The individual Organ Cartridges can be connected together to form a multi-organ system in which fluids from one Organ Cartridge can be routed to other Organ Cartridges. In this diagram the Heart module is shown delivering fluids to the Lung module and the Liver module. The Lung and Liver are shown to be connected via a separate fluid connection. The underlying support network supplies fluids, gases and waste removal according to the programmed status demands of each individual organ's Perfusion Control subsystem.

FIG. 41 shows schematically a parallel configuration of Organs-on-a-Chip. The input to each Organ-on-a-Chip is connected to the common "arterial" supply line, and the effluent from each organ is connected to the common "venous" line. Each Organ Chip as shown would be maintained by its respective Organ Cartridge which could also include an individual perfusion controller and microclinical analyzer, with the pumps being either in series with the organ or in parallel. One or more vascular return pumps located in the Cartridge Dock, with respective pressure regulators, route the venous flow to the arterial circulation. Gas exchange is provided by either a discrete membrane gas exchanger or another such device, or through the gas permeable properties of the material out of which the microfluidic Organ Chip is constructed.

FIG. 42 shows schematically a parallel-series configuration of Organs-on-a-Chip. The input to each Organ Chip is connected either to the common "Arterial" supply line, and the effluent from each organ is connected to the common "Venous" line, in parallel mode, or two or more organs can be connected in series, here shown by the effluent from the gut entering the liver and then being passed to the common venous line. Each Organ Chip as shown could also include an individual perfusion controller and microclinical analyzer, with the pumps being either in series with the organ or in parallel. One or more vascular return pumps, with pressure regulators, return the venous flow to the arterial circulation, with gas exchange being provided by either a discrete membrane gas exchanger or another such device, or through the gas permeable properties of the material out of which the microfluidic device is constructed.

FIG. 43 shows a schematic representation of three Organ Cartridges in a Cartridge dock with their respective perfusion controllers. The figure shows three different interconnected Organ Chips. Upper: Introduction of fluid in Organ N−1 with the effluent going to a Fluids-Out port for either analysis or disposal. Middle: The cartridge for Organ N running on internal recirculation with local gas exchange and an internal shunt to regulate the flow. The arterial circulation bypasses the Organ Cartridge to maintain homeostasis of other organs. Lower: Organ N+1 is connected between the arterial and venous circulations with the variable, low impedance shunt regulating the organ flow for the given arterial-venous pressure differential. A sample is being withdrawn for external analysis. At the bottom of the figure, a pump located on the Cartridge Dock provides venous return. Organ-level gas exchangers or a master gas exchanger could be inserted if required.

Of particular note are the parallel organ-support architecture and the versatility of inter-organ connectivity which is built into the programmable Perfusion Control subsection of each organ chip cartridge:

(1) Each Organ Chip location is provided with its own support network. The organ support network (bottom layer on the drawing) is of a uniform design, allowing any type of standardized organ chip to plug into any position in the organ array.

(2) The precise fluidic connectivity between Organ Chips is controlled by the Perfusion Control subsystem built into each Organ Cartridge. In this particular design (FIG. 40), the Heart Cartridge is shown providing fluid to both the Lung Cartridge and the Liver Cartridge, and the Lung and the Liver are also shown as connected.

(3) The important conserved design elements apparent in this diagram are consistent modular design and versatile inter-organ connectivity allowing for flexible multi-organ experiment protocols.

(4) The details of the interconnects between organs, perfusion controllers, the microfluidic vasculature, the microfluidic interstitium, and the fluid, gas, and waste buses can be configured to suit the specific needs of an individual experiment and an Organ Chip array, either at the initiation of the experiment or during its course.

Figure 8:
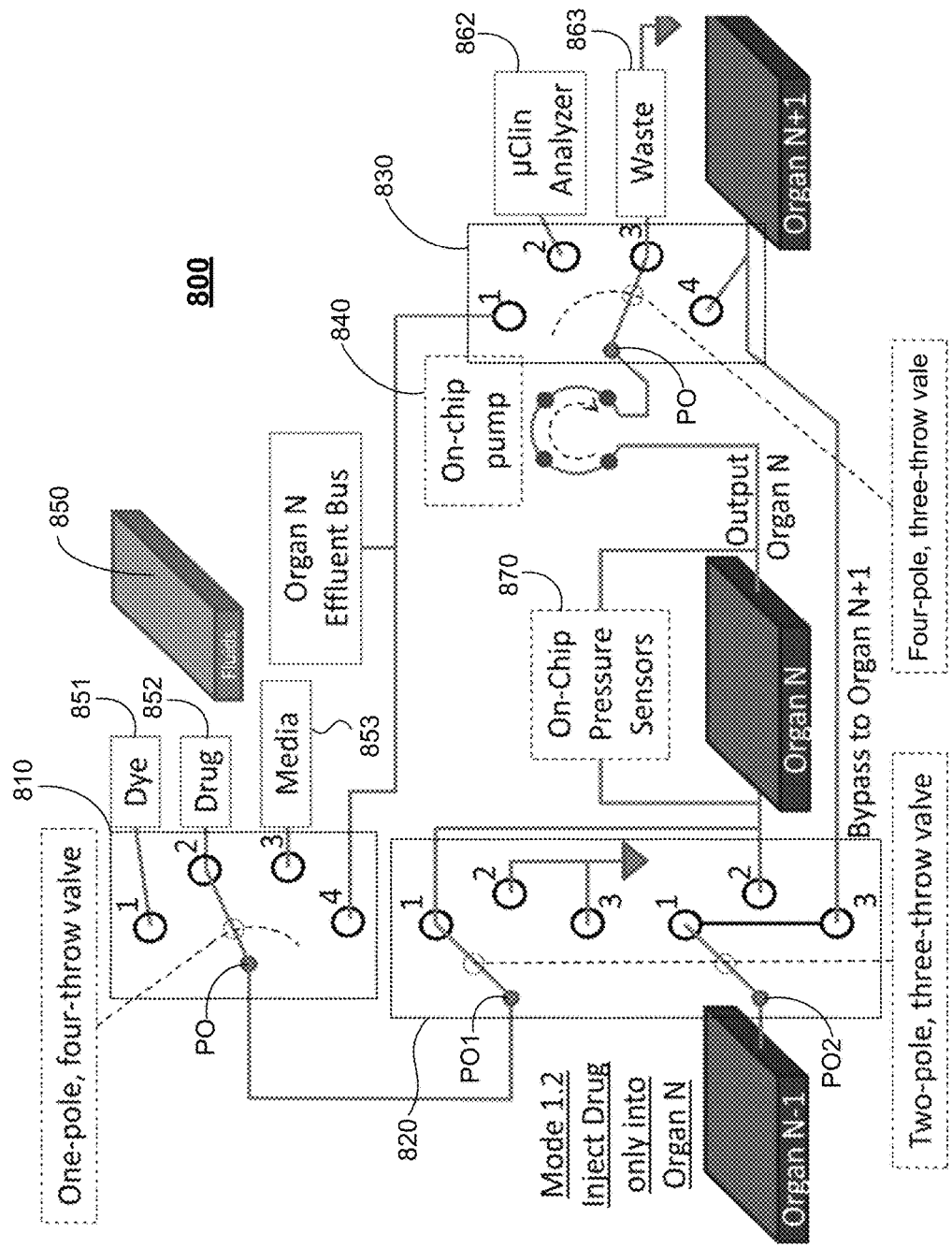
FIG. 8 shows schematically a perfusion controller according to one embodiment of the invention. The exemplary perfusion controller can operate in three modes: 1) Blood substitute bypasses Organ N while the input to Organ N is connected to an on-chip fluid-selector valve that allows the perfusion of the organ with a dye, drug, or media drawn from the fluid bus; 2) Organ N is between Organs N-1 and N+1 so that the three organs are perfused in series; and 3) Organ N is removed from the system for a stop-flow measurement, repair, or replacement. In the configuration, Organ N Cartridge is disconnected from the system, and the effluent from Organ N-1 goes to Organ N+1. A drug is injected only into Organ N. Media can follow the drug to wash out unbound drug. The effluent is sent to waste so as not to expose other organs directly to the drug. The two on-chip pressure sensors measure the absolute pressure in the organ inlet and outlet. Their difference reflects the pressure drop across the organ, and thereby allows control of the speed of the on-chip pump to regulate system flow. The pump output can be either recycled back into the organ, sent to the microclinical analyzer, to waste, or to Organ N+1. Additional features of this design can support multi-organ parallel perfusion connectivity by redefining the Media and Waste switch positions to correspond to Arterial Supply and Venous Drain, respectively. Therefore, this type of perfusion controller can be used for either series or parallel organ perfusion, or a combination thereof.

FIGS. 8 and 27 illustrate more details of a Perfusion Control subsystem built into each Organ Cartridge as disclosed above. This example illustrates one particular implementation of fluidic switch interconnectivity which would enable versatile multi-organ interconnectivity and measurement. In this schematic diagram the fluidic pathways are controlled by multi-position fluidic switches, which could be implemented using a variety of techniques.

Specifically, the perfusion controller has a plurality of inlets for providing a plurality of fluids (851, 852 and 853 as shown in FIG. 8), a plurality of outlets, and a fluidic network coupled between the plurality of inlets and the plurality of outlets and being in fluid communication with the plurality of bio-objects. The fluidic network comprises a plurality of fluidic switches 810, 820, and 830 and one or more on-chip pumps 840 adapted for selectively and individually perfusing at least one of the plurality of bio-objects with at least one of the plurality of fluids at a predetermined perfusion flow rate and delivering an effluent of the at least one bio-object responsive to the perfusion to a predetermined one of the plurality of outlets, where the plurality of outlets is coupled to at least one of an analyzer 862, a waste port 863, one of the plurality of bio-objects, and the fluidic switch network.

In this exemplary embodiment, the perfusion controller further includes a fluid reservoir 850 having a plurality of containers (851, 852, and 853) for containing the plurality of fluids, respectively. The plurality of containers is coupled to the plurality of inlets for respectively providing the plurality of fluids. The desired fluids contain a dye for labeling selective areas within the bio-object 851, a drug 852, a medium 853 or the like.

The perfusion controller may also have a microcontroller for individually controlling the plurality of fluidic switches and the one or more on-chip pumps of the fluidic network as so to control a flow rate of each fluidic path.

The perfusion controller further includes one or more sensors 870 coupled to the at least one bio-object for measuring a pressure drop across the at least one bio-object perfused with the at least one fluid, so as to regulate the flow rate of the at least one fluid through the at least one bio-object at the predetermined perfusion rate, provided the bio-object resistance is known or calculable.

The fluidic network is formed with a plurality of fluidic paths in fluid communication with the plurality of fluidic switches and the one or more on-chip pumps, where each bio-object is disposed in a corresponding fluidic path.

Each fluidic switch comprises a valve having at least one pole and two or more throws, where the at least one pole is selectively operable in fluid communication with one of the two or more throws.

The fluidic network comprises first, second, and third fluidic switches 810, 820, and 830 and an on-chip pump 840. The first fluidic switch (810) comprises a one-pole four-throw valve, the second fluidic switch (820) comprises a two-pole three-throw valve, and the third fluidic switch (830) comprises a one-pole four-throw valve. In this embodiment, the plurality of bio-objects includes organ N−1, organ N, and organ N+1, where the organ N−1 is coupled to the second fluidic switch, the organ N is coupled between the second fluidic switch and the on-chip pump that is in turn coupled to the third fluidic switches, and the organ N+1 is coupled to the second and third fluidic switches.

The example shown can operate in three modes: 1) Blood Substitute Bypasses Organ N while the input to Organ N is connected to an on-chip fluid-selector valve that allows perfusion of the organ with a dye, drug, or media drawn from the Fluid bus; 2) Organ N is between Organs N−1 and N+1 so that the three organs are perfused in series; and 3) Organ N is removed from the system for a stop-flow measurement, repair, or replacement.

In the configuration shown, Organ Cartridge N is disconnected from the system, and the effluent from Organ N−1 goes to Organ N+1. Therefore a drug is injected only into Organ N. Media can follow to wash out unbound drug. The effluent is sent to waste so as not to expose the downstream organs directly to the drug. The two on-chip pressure sensors measure absolute pressure between the organ inlet and outlet. Their difference reflects the pressure drop across the organ, and thereby allows control of the speed of the on-chip pump to regulate system flow. The pump output can be either recycled back into the organ, sent to the microclinical analyzer, to waste, or to Organ N+1. Additional features of this design can support multi-organ parallel perfusion connectivity by redefining the Media and Waste switch positions to correspond to Arterial supply and Venous Drain, respectively. Hence this type of controller can be used for either series or parallel organ perfusion. In addition, according to embodiments of the invention, the pump could be upstream or downstream of either the organ or the µCA electrode arrays.

If the pump is a pneumatically actuated peristaltic pump, or a peristaltic pump with multiple, independent mechanical actuators, then application of no pressure leaves the pump in the open position, thereby allowing free flow through the channels. Were rotary planar peristaltic micropumps (RPPMs) used and one desired to run the organ with flow driven solely by other organs or off-chip pumps, then it would be necessary to add a mechanical retractor to the drive balls, or insert a unidirectional flapper bypass valve or a selector bypass valve across the pump.

The three independent switch arrays shown on this diagram would be controlled by a computer to enable a wide variety of modal capabilities as detailed in the description of FIG. 40. Note that while the basic organ-to-organ connection supported by this design is an in-line series connection between physically adjacent modules, the switch arrays allow other configurations as well, including organ bypass, fluid flushing, and stop-flow organ effluent analysis using the microclinical analyzer chip.

This configuration enables either direct series perfusion of a set of organs, or through the Organ Effluent buses (one for each organ), parallel perfusion of the organs, as desired. The one-pole four-throw valves on the input and output sides of the organ can be replaced with valves with additional ports for selection of the input and output connections of all organs in the system from a number of possible fluid streams.

Among other things, an important feature of this design is that each Organ Chip can have a dedicated, in-series or in-parallel pump that can drive flow through an organ independent of the flow through other organs.

Each organ also is shown as having on-chip pressure sensors that are used to regulate the flow through the system and determine whether the fluidic resistance of the organ is within the desired range.

The output valve of the circuit can direct the flow to a microclinical analyzer.

This design and similar ones using the multi-position valve approach offer an extremely versatile set of features spanning the range of both serial and parallel connectivity. A number of specific features of this approach are of fundamental importance for enabling reliable long-term viability of all the organs in a multi-organ module and also for enabling well-controlled experimental paradigms which can provide physiologically relevant data concerning drug and pathogen multi-organ responses.

Note particularly the following specific points:
According to the invention, each organ can be in series or in parallel with its own perfusion metering pump. This is extremely important in that it allows for each specific organ to individually receive specific perfusion flow rates. This is of absolutely fundamental importance for:
  (a) The detailed balancing of relative organ perfusion rates in order to obtain physiologically relevant data.
  (b) Providing scientists who design and analyze experiments run in the multi-organ experimental module with the detailed perfusion rate history associated with each organ that might have participated in a multi-organ related cascade of events resulting in particular drug or pathogen responses.
  (c) Providing scientists with ability to simulate naturally occurring increases or decreases in individual organ blood flow that would occur during normal physiological stimulation or during particular types of traumatic or pathological events being studied.
  (d) Limiting safe levels of blood pressure supplied to particular organ modules that may not be able to tolerate a full systemic pressure drop which exists in the full Arterial-Venous differential pressure drop.
  (e) Allowing intermittent or stop-flow conditions within a particular organ module, which may be desirable for increasing the concentration of organ metabolites prior to analysis with the microclinical analyzer, and providing additional organ residence time for bolus delivered drugs, or biomolecules emanating from other organs.

In addition, according to the invention, this system provides versatile and re-configurable organ interconnection capability and organ effluent analysis capability. For example,
  (a) The organs can be perfused with fresh (non-recirculated) media for external analysis.
  (b) The organs can be connected in parallel, sharing common recirculating Arterial and Venous fluidic paths, as depicted in FIG. 43. A simple pressure-regulated pump circuit such as that shown in FIG. 43 could recycle Venous System fluids to the Arterial System supply line.
  (c) Individual organs can be connected in series, so that the effluent from one organ is routed into the fluidic input of another organ, as shown in FIG. 8.
  (d) An individual organ can be temporarily isolated from the Arterial-Venous system and be reperfused with its own recirculated effluent, as shown in FIG. 30A, for simulating local oxygen starvation or poor organ blood flow, and/or for allowing concentrations of metabolic products to increase prior to analysis.
  (e) A simple expansion of the number of switch positions available on the fluid input and fluid output beyond the four-position switches shown in this particular diagram, as shown in FIG. 43 could easily enable more complicated chains of organ perfusate interconnection if that should be required for particular multi-organ experiments.

In any case, it is important to minimize the fluid volume of all valves, interconnects, and tubing, since this volume may be a significant factor in determining the required cell growth chamber volumes in order to keep dilution effects from rendering the entire assembly physiologically unrealistic.

An organ can be transiently placed in either a stop or local recirculating mode to allow accumulation of paracrine signals and metabolites prior to withdrawing a sample for external analysis. By giving each cartridge a pump and pressure sensors it is possible to ensure the proper flow through each organ when operating in either the series or parallel mode.

Chip oxygenation can be either through the PDMS or with Cartridge or systemic gas exchange membranes.

According to the invention, the perfusion controller can also deliver fluid samples to the microclinical analyzer ($\mu$CA), which has three components: the disposable microclinical analyzer chip which includes the sensor array, the microfluidics, valves, and a pump, the microclinical analyzer valve and pump drives which are implemented using rotary motors or pneumatic controllers that attach to the disposable $\mu$CA chip, and the $\mu$CA Sensor Electronics which is shared between multiple microclinical analyzer units by using a microclinical analyzer Sensor Multiplexer. This microclinical analyzer allows for the automated implementation of multianalyte microphysiometry, as invented by Cliffel and Wikswo, within a single Organ Cartridge.

There are a large number of commercial instruments for measuring bioreactor process variables, such as glucose, lactate, pH, and $O_2$. Clinical analyzers with disposable enzyme films, e.g., YSI, have been optimized for measuring electrolytes in mL volumes of blood plasma and have detectors with large surface areas and hence large dead space. Simple glucose sensors abound, but are not readily interfaced and do not have long-term stability or calibration.

The Molecular Devices Cytosensor Microphysiometer, manufactured for 15 years beginning in the early 1990's, could measure only pH, albeit with milli-pH sensitivity, 15 second time response and several microliter volumes enclosing about $10^5$ cells. Measuring only pH is insufficient to detect many metabolic changes in cells, since multiple mechanisms lead to acidification. Eklund et al. added glucose, lactate, and $O_2$ sensors to the Cytosensor using expensive commercial potentiostats, and then replaced these potentiostats with an economical, custom unit. However, none of these systems offers the level of calibration control required for long-term studies with a single set of sensors.

Conventional acidification microphysiometry measures the pH changes produced by the energy metabolism of approximately 300,000 live cells in a 3-microliter chamber. Cliffel et al. added multiple additional electrochemical sensors for metabolic analytes into this chamber to give a complete dynamical picture of the live cell physiology as a Multianalyte Microphysiometer. Their four-analyte system currently measures extracellular glucose, oxygen, lactate, and pH within a microfluidic chamber simultaneously on the minute timescale. They have also added the ability to monitor extracellular calcium and dopamine levels for primary neurons and neuronal-like cells, and insulin for pancreatic islets. Physiological measurements include dynamic measurements of basal metabolic rates in various media, agonist/antagonist competition studies, toxicology, and dose-response curves. Cellular activity, metabolic dynamics, and recovery after drug exposure will be monitored directly. By combining all of the information contained in the multianalyte "biosignature" metabolic activities of each organ-on-chip, including metabolic pathway shifting from aerobic to anaerobic metabolism, the depletion of internal energy stores, and the dynamic decoupling of metabolic parameters can be observed.

In the applications of multianalyte microphysiometry, the inventors have explored metabolic toxicology, metabolic activity of neurons undergoing stroke-like conditions, macrophage activation, pancreatic islet responses, and cancer cell metabolism, as shown in FIG. 26, which summarizes the preliminary studies on the metabolic effects of the activation of T-cells in the microfluidic chamber, as well as looking at the metabolic processes involved in the oxidative burst response of RAW macrophage. Further, we have also adapted the multianalyte microphysiometers to measure insulin release to study the physiology and function of extracted primary pancreatic islets as a means of testing their viability before possible transplantation. Finally, we have extended the multianalyte microphysiometry to measure the Warburg effect of aerobic glycolysis in cancer.

According to one embodiment of the invention, the disposable microclinical analyzer chip includes three well-established components: an electrode sensor array for each chamber, microfluidic chambers, and pumps with valves. The sensor array chips are based on screen printing electrodes commercially fabricated to the specifications, as shown in FIG. 25. In one embodiment, these chips include five screen printed platinum electrodes per array onto 6×9 cm ceramic substrates with six arrays per substrate chip. Two substrate chips can then measure the four different analytes (Glu, Oxy, Lac, pH, etc.) in each of the twelve different chambers simultaneously. For glucose and lactate sensing, chemical inkjet printing or other methods can be used to deposit the individual enzyme layers necessary for the selectivity of each sensor. Also, for oxygen sensing, a Nafion coating or other membrane can be applied to the sensor to prevent biofouling. For the pH sensor, a pH-sensitive iridium oxide layer will be electrodeposited onto those specific sensor electrodes. Good laboratory practices and sterilization procedures will ensure the quality control of these sensors. These sensors will be calibrated before use in the microclinical analyzer to verify their quality.

The Vanderbilt custom-built multichannel multipotentiostat, as shown in FIG. 24, is used in conjunction with the on-chip microclinical analyzer electrode sensor arrays to provide calibrated readouts of selected analyte concentrations. Two of these multichamber multipotentiostats are required for a 12 location measurement setup with 10 individual organ cartridges and two sensor arrays devoted to measuring the main fluidic lines.

In addition, these individual sensor array chips can be fabricated for easy insertion into the microfluidics stage of the microclinical analyzer, allowing for convenient replacement of sensor arrays as needed. The sensor array chips can be reused by chemically removing and re-depositing the enzyme and iridium oxide layers. When plugged into the microclinical analyzer, the microfluidic valves select between in-line measurements of the fluids leaving the organ chambers or sets of calibration solutions with different concentrations of each analyte to ensure in situ accuracy of the sensor readouts. These valves also control output fluidic sampling for analysis by ion mobility-mass spectrometry (IM-MS). The flow rates utilized to maintain the tissues are well matched to the flow rates of nanoelectrospray, ion mobility-mass spectrometers (nESI-IM-MS) (100-500 nL/min), so that the fluid being exchanged between organs can be sampled with time resolutions of one minute. Ion Mobility-Mass Spectrometry is the keystone technique in this omni-omics advance developed in the McLean laboratory to rapidly analyze for lipids, carbohydrates, peptides, and nucleotides simultaneously. This technology enables three-dimensional separations, such as analyte structure, mass-to-charge and signal intensity, to be completed on a time-scale of milliseconds.

Possible improvements in the microclinical analyzer include the ability to add other analyte sensors as desired, some of which could be specific for each organ, and the ability to expand the number of analytes in each chamber with custom designs for the sensor arrays and improved multipotentiostats.

Referring to FIG. 23, a microclinical analyzer is shown according to one embodiment of the invention, which illustrates some of the critical features which must be included in the microclinical analyzer subsystem. These are required in order to provide periodic calibration of the electrochemical sensor elements used to assay the concentration of biomolecules in the organ effluent stream. This valve system operates under computer-directed control, such as processor, microcontroller, or the like, to enable periodic multianalyte electrochemical measurements from the upstream organ between time slots devoted to sensor cleansing and calibration which are necessary to ensure accurate measurements.

Specifically, the microclinical analyzer includes a fluidic network having a plurality of fluidic switches 2310, 2320, 2330, a plurality of fluidic paths in fluid communication with the plurality of fluidic switches, and one or more on-chip pumps 2340 coupled to corresponding fluidic paths, a sensor array 2370 coupled to the fluidic network; and a microcontroller (not shown) for individually controlling the plurality of fluidic switches 2310, 2320, 2330 and the one or more on-chip pumps 2340 of the fluidic network as so to operably and selectively deliver an effluent of at least one bio-object to the sensor array for detecting properties of the effluent, or to a predetermined outlet destination, wherein the effluent of the at least one bio-object is from perfusion of the at least one bio-object with a desired fluid performed within a perfusion controller 2380.

The microcontroller is provided with at least one of a wireless communication protocol and a backup battery.

The microclinical analyzer, as shown in FIG. 23, also has a calibration reservoir 2350 having four containers 2351, 2352, 2353 and 2354 for containing a plurality of fluids, respectively. In the embodiment, the four containers 2351, 2352, 2353 and 2354 are coupled to the first fluidic switch 2310 for individually providing the plurality of fluids to the sensor array 2370 for calibration. Each fluidic switch is a valve having at least one pole and a plurality of throws, wherein the at least one pole is operably and selectively in fluid communication with one of the plurality of throws. For example, the first fluidic switch 2310 has one pole, PO, and four throws 1, 2, 3, and 4 respectively connected to four containers 2351, 2352, 2353 and 2354. The second fluidic switch 2320 has four poles PO1, PO2, PO3 and PO4 and three throws 1, 2 and 3. The third fluidic switch 2330 has one pole PO and four throws 1, 2, 3, and 4 respectively connected to Organ N Effluent Bus 2361, External Sampler 2362, Waste Port 2363 and Organ N+1. The pump 2340 is connected to the third pole PO3 of the second fluidic switch 2320 and the pole PO of the third fluidic switch 2330.

For such a microclinical analyzer as shown in FIG. 23, there are three operational modes enabled by the four-pole three-throw valve in this system: 1) the Organ Output passes over sensor array for electrochemical measurements of metabolites. 2) The Organ Output bypasses the sensor array, and the sensor array is isolated to prevent sensor fouling by proteins in perfusate. 3) The Organ Chip perfusate bypasses the sensor array, allowing the sensor array to be calibrated with 3 or more calibration solutions or loaded with wash media by means of a one-pole four-throw valve, with the waste sent to drain to protect all organs from calibration fluids. A one-pole four-throw valve allows the effluent from Organ N to pass onto the perfusion bus for that organ, to be delivered to an external sampler, or to Organ N+1. Additional poles on the switches would enable additional modes.

In one embodiment, the microclinical analyzer also delivers small volumes of organ effluent solutions for processing by an in-line desalter connected to an Ion Mobility-Mass Spectrometer, or larger volumes to an Ultra-Performance Liquid Chromatography Mass Spectrometer System or other such mass spectrometer analytical approach.

Various perfusion controller switching array methods can be utilized in multi-organ array systems. The most obvious implementation of coupled, multi-organ systems involves serial perfusion of the organs, with one or more pumps in series, such that the effluent of one organ could be used, possibly diluted, as the input to a downstream organ. In these designs control features would rely on variable speed pumps and cartridge pressure sensors to monitor and control cross organ pressure drops. A superior and more physiological means is to use designs that involve a versatile parallel Arterial-Venous supply architecture which more closely mimics the normal physiological relationships between organs. Some of the initial versions of this type of configuration can be seen in FIGS. 41 and 42. Note that this general structure corresponds to what we term a "Parallel Organ Perfusion" network and that it is fundamentally different from the organs-in-series architecture. In nature, certain organs, such as Gut and Liver, do receive circulation more akin to the organ-in-series structure depicted in FIG. 42.

FIG. 38 shows a more detailed schematic of a parallel-organ perfusion controller, which illustrates one possible implementation of a parallel multi-organ perfusion network as an alternative to the parallel perfusion functionality which is inherent in the embodiment shown in FIG. 8. Note particularly the physiological relevance and experimental versatility inherent in these schematic diagrams suitable for parallel perfusion of multi-organ experiment systems:

(1) Organs can be arranged between a parallel Arterial supply and Venous return blood substitute recycling system which mirrors normal mammalian physiology.

(2) Switching arrangements allow for normal flow or stop flow measurement of chemicals in the organ efflux path.

(3) Alternative fluids (drugs or dyes) can be supplied individually to any organ.

(4) Fluids can be collected for external analysis from the effluent path of individual organs.

(5) Internal module pumps and variable fluidic resistance pathways can be used to adjust the pressure across individual organs and also to adjust the blood bypass ratio to establish appropriate blood substitute distribution ratios between individual organs.

Because the Multi-Organ Experimental Platform is intended to support long-term live tissue experiments, sterilization of the perfusion controller and the microclinical analyzer microfluidic chips must be considered during every stage of their design and manufacture. Ethylene Oxide treatment will ensure sterility during shelf life but it is necessary to ensure that the residual Ethylene Oxide has escaped from the plastic before it is in contact with fluid that perfuses living cells. Alternative sterilization methods techniques include autoclaving, gas, alcohols, or radiation.

The sensors must be sterilely inserted even if the instrument is not in a sterile environment. The surrounding support instrument should have atmospheric control with positive pressure to eliminate the inclusion of contaminated particles or spores in the cartridge loading area.

Microfluidic devices inherently constrain the atmosphere in and around the experimental area. According to the invention, the characteristics of the materials can be leveraged to enhance the control of the environment inside the materials instead of trying to control the external environment.

The temperature of the fluids moving through the perfusion controller can be regulated either by regulating the temperature of the entire enclosing environment or by having temperature-control fluid or other means to ensure that the devices are at the desired temperature. Most microfluidic devices are constructed from polymers which are excellent thermal insulators, allowing the control of temperatures inside the devices without being concerned about accurate control of the external temperatures. Humidity can also be controlled inside the device by adding water jacket channels to keep water-permeable polymers saturated in water, simulating an external atmosphere of 100% humidity. In addition, gases may be dissolved in the water jacket to control the gas atmosphere in the experimental areas.

Controlling only the internal environment simplifies the task of maintaining sterility by eliminating any air space that has high humidity and therefore eliminating the promotion of fungal and bacterial growth that thrives in moist atmosphere.

Heated HEPA filtered air will create a dehydrating environment outside the fluidic device which will reduce fungal and bacterial growth and destroy viral material faster than a standard atmosphere. This air may also be treated with such things as UV radiation and activated charcoal filters to ensure sterility and control VOCs that may be present in laboratories.

A disposable, adhesive-backed membrane that is permeable to oxygen, carbon dioxide, and water vapor can be used to eliminate cross-contamination or microbial infiltration from any ports that need to remain open to air when devices or subassemblies have to be handled outside of a sterile, laminar flow hood.

Both the perfusion controller and the microclinical analyzer, as well as the Organ Chip itself, require computer control to ensure long-term cell viability and maintenance of realistic conditions for physiological studies. The computer control system must be capable of measuring important variables in the system, such as temperature, pressure, dissolved gases, nutrients, and metabolites, and responding accordingly. The software protocols are required for control of the multi-organ system, including the Organ Chip Cartridge, the mechanical and perfusion controllers, and the microclinical analyzer, and the Support Systems, which include External Sample Perfusion using the valves and pumps already described. In one embodiment of this system, the control of all of these components is performed by the Master Control Computer described above, or by a set of microcontrollers that in turn are controlled by the Master Control Computer, with connections either hardwired or wireless.

Microcontrollers, such as pump or valve controllers, or local temperature, humidity, or gas composition controllers, or electroanalytic modules, can be efficiently and economically integrated into the system as local microcontrollers that operate under the direction of the main Master Control Computer. This computer would be responsible for all real-time control aspects of the growth of cells in the Organ Chips and the subsequent experiments, and will also be responsible for acquiring all relevant information from the various subsystem microcontrollers.

The Master Control Computer can implement a detailed protocol at preset time points and export the data as a time-stamped confirmation of each individual action performed and each individual measurement gathered over the several week duration of the experiment. The database record will be crucial to understanding and interpreting the complicated multi-organ interactions, and it is very important that visualization tools be created from the outset that will allow scientists to easily visualize multi-component graphs of data extracted from the comprehensive database record.

The valves and pumps described in the invention can be implemented in a variety of ways, including pneumatic push-up or push-down, normally open valves, membrane-between-glass microfluidic valves that are normally closed, electromechanically actuated valves, rotary planar valves and rotary planar peristaltic micropumps, as shown in FIG. 5, or by vibrating membrane check valve pumps. The implementation of the designs shown here does not depend upon the specific type of valve being used.

As disclosed above, one aspect of the invention provides a new category of microscope-compatible devices that allow active control of cell culture parameters and fluid flows as needed for long-term culturing and analysis of biological tissue and cellular constructs and assemblies. Although this invention is focused on the use of microfluidic chips for cell culture and thus terms the device a "chip carrier," it is not restricted to the application of the device to the control and perfusion of microfluidic systems. It could equally be applied to the manipulation of fluids in wells, small dishes, or other culture chambers.

The principal novel features of these devices, which are illustrated in the accompanying FIGS. 28-36, are, among other things:

(1) A standardized external mechanical footprint that is compatible with all microscope stages, for example using the industry-standard Society of Biomolecular Screening (SBS) wellplate specification.

(2) The chip carrier which can accommodate microfluidic bioreactors, hollow fiber bioreactors, tissue constructs, tissue samples such as those obtained from biopsies, and other types of cell growth chambers. These types of biological sample-holders which reside within the overall device are herein referred to as the "chip" and the surrounding, supporting device is referred to as the "Chip Carrier".

(3) In one embodiment, an optically transparent region within the chip carrier which can accommodate glass or plastic slides of various dimensions and microfluidic bioreactors, tissue constructs, tissue samples such as biopsies, and other types of cell growth chambers and thereby enable microscopic observation of the cells in the device.

(4) The Chip Carrier is designed to provide stand-alone fluidic media and nutritional support for the biological material in the chip. This is accomplished by including within the Chip Carrier assembly one or more fluidic reservoirs and one or more controlled fluid delivery pumps. The purpose of the pump is to provide a continuous or intermittent delivery of cell growth media to the biological material in the chip. In the simplest implementation the chip carrier would include just one reservoir for recycled media. Alternatively, it could contain two reservoirs, one for fresh cell growth media, and another to contain the waste fluid which comes out of the chip when the pump operates to introduce fresh cell growth media into the chip. In the former case the media becomes conditioned over time through the accumulation of cytokines, metabolites, and signaling molecules, and the nutrient levels slowly decline. In the latter case the media does not recirculate, the concentrations of these products to which the cells are exposed do not increase with time, and the concentrations of nutrients stay constant.

(5) In other embodiments of the Chip Carrier, multiple fluidic reservoirs and either multiple pumps, or pumps used in conjunction with fluidic input and/or output valves, could be used in order to deliver various combinations of cell media, drugs, and other liquid compounds to the biological material in the chip.

(6) In other embodiments of the Chip Carrier, multiple fluidic reservoirs and either multiple pumps, or pumps used in conjunction with multi-position fluidic input valves could be used in order to deliver various combinations of cell media, drugs, and other liquid compounds to the biological material in the chip.

(7) A key feature of the invented chip carrier is the inclusion of an electronic microcontroller and an on-board battery. The purpose of the microcontroller is to provide signals to the pump(s) and fluidic valve(s) assemblies that feed the biological material in the chip assembly. The purpose of the battery is to allow operation of the pumps and valves in the carrier when it has been disconnected from its standard power supply, for example during transport or while being examined microscopically or chemically.

(8) A key feature of the invented chip carrier is the ability of the microcontroller to implement complicated fluid and drug delivery protocols to the biological material on the chip. The protocols can be preloaded into the microcontroller and the chip carrier can implement these fluid delivery instructions without human intervention.

(9) The microcontroller can also make autonomous decisions regarding pumps and valves based upon the output of embedded sensors.

(10) Another feature of the invented chip carrier is that the microcontroller can include a wireless electronic input port. This input port can be used to deliver new fluidic control protocols to the Chip Carrier microcontroller, and it can be used to temporarily override existing protocols, for example: investigators may not want fluid to flow through the chip assembly while they are observing the biological sample on a microscope, or for example, investigators may want to deliver certain fluids to the biological sample only when the chip carrier is being observed on a microscope.

(11) A key feature of one embodiment of the invented Chip Carrier is the inclusion of on-board sensor elements (termed a microclinical analyzer). This assembly of pumps and valves can be used to sample the effluent from the biological material in the chip and use electrochemical, optical, or other means to measure certain metabolites or other specific molecules contained in the effluent fluid. A key feature of the invented Chip Carrier design is the inclusion of microprocessor-controlled pumps, valves, and electrochemical sensor elements to accomplish this task. A key feature of the invented Chip Carrier design is the ability of this design to provide calibration and biofouling protection for the chip carrier resident sensor elements.

(12) A key feature of the invented Chip Carrier is that it can be programmed to deliver precise amounts of cell chamber effluent on demand to an external microfluidic port; for example, in situations when investigators wish to use a device such as an external mass spectrometer or other analytic instrument to analyze the output of the chip.

(13) One of the most important features of the invented Chip Carrier is that it is a self-contained device which can be easily transported between the long-term incubator environment and the short-term microscope evaluation environment without compromising sterility of the closed fluid delivery system and without interrupting desired fluid delivery protocols.

(14) A key feature of the invented Chip Carrier design is the closed fluid delivery system which can accommodate pre-sterilized fluid samples and pump/valve assemblies and which includes sterile vent assemblies on all fluid supply and fluid waste assemblies. This is extremely important in the context of long-term cell culture experiments.

(15) A key feature of the invented Chip Carrier design is the ability of this design to accommodate in-line fluid de-bubbler assemblies. These fluid de-bubbler assemblies are designed to prevent small bubbles of air from interfering with cell assemblies or fluid delivery channels.

(16) A key feature of some implementations of the invented Chip Carrier design is the inclusion of on-board micropumps to deliver vacuum suction to operate certain classes of on-board debubbler and/or mechanical attachments.

(17) The on-board pumps could also provide computer-controlled suction or pressure as required to operate various vacuum—or suction-activated chips.

(18) A key feature of some implementations of the invented Chip Carrier design is the inclusion of on-board micropumps to deliver pressurized sterile air to operate certain classes of on-board oxygenator attachments.

(19) The invented Chip Carrier contains a battery assembly which can power all pumps and valves when the unit is disconnected from an external charging station. The invented chip carrier design includes a battery-charging circuit which allows batteries to be recharged—typically during the periods when the chip carrier resides within an incubator. The invented Chip Carrier design incorporates an easy-insertion electrical connector for this purpose.

(20) A key advantage of the invented Chip Carrier design is that the fluidic system is completely enclosed. This offers the additional advantage of allowing use in low humidity incubators, which are less likely to corrode electrical contacts and less likely to support fungal and bacterial contamination.

(21) The invented Chip Carrier could also include on-board temperature regulation, so that the chips could be maintained at a desired operating temperature, either above or below the ambient temperature, without the need for an external incubator.

(22) The Chip Carrier can be implemented with one or more reservoirs and one or more pumps but without a microcontroller.

(23) The Chip Carrier can include fluid flow and fluid pressure sensors.

Further aspects of the invention include, among other things, Integrated Organ Microfluidics (IOM) Chip and applications of the same. Particularly, various embodiments of the invention are focused on the integration of pumps, valves, bubble traps, cell chambers and supporting fluid networks and interconnects into a single IOM Chip. The IOM can be used as one component of an organ-on-chip cartridge that includes, for example, a chip carrier to support the IOM and the motors for pumps and valves.

Conventionally, many Organ-on-Chip systems utilize discrete components, such as pumps and valves that are connected to the organ by tubing. A major problem of this approach is the volume of fluid contained by the tubing. Thus, it is important to minimize this volume and thereby avoid unnecessary dilution of metabolites and signaling molecules that comprise the chemical communication between different organs.

As disclosed in the invention, the IOM chip addresses this problem by integrating on-chip rotary planar peristaltic micropumps (RPPMs), rotary planar valves (RPVs) and microfabricated bubble traps (MBT) with the organ or organs on a single chip. In one embodiment, the IOM chip is made out of an optically clear polymer to allow both fluid manipulation within the chip and light transmission for observation of biological samples within the chip. This single, disposable chip sits in a "chip carrier" as described previously which houses the stock solutions, driving electronics, and mechanical support for the insert. The combination of chip carrier and IOM comprises the organ-on-chip cartridge.

FIGS. 33-36 show various embodiments of an intelligent chip carrier, or an integrated bio-object microfluidics chip, according to the invention.

As shown in FIGS. 33 and 34, the integrated bio-object microfluidics chip has a base carrier 3310/3410 defining the footprint of the device, a plurality fluidic paths, holes and chambers/slides 3360/3460, etc. for accommodating components of the chip. The components include, but are not limited to, an inlet reservoir 3330/3430, an outlet reservoir 3370/3470, a microfluidic device mounted to the chambers/slides 3360/3460, a microcontroller 3340/3440 with wireless interface for in-incubator system pump control with one DC power connector, a backup battery 3350/3450 for out-of-incubator transportation and tests, and a RPPM pump with a DC gearhead motor 3320. The base carrier is a plastic SBS-format chip carrier.

FIG. 35 shows another embodiment of the integrated bio-object microfluidics chip, which has a cells/organ chamber 3570 for accommodating cells/organ to be analyzed, reservoirs 3530, eight microfluidic pumps or valves 3520, and a microcontroller 3540 with wireless interface for in-incubator system pump control with a backup battery for out-of-incubator transportation and tests. The base carrier is a plastic SBS-format chip carrier. FIG. 35 features an IOM chip, 3570, in which all fluidic connections are made within the device, without the need for tubing to connect the microfluidic pumps and/or valves.

In one embodiment, as shown in FIG. 36, the integrated bio-object microfluidics chip, i.e., intelligent chip carrier, has at least one perfusion controller (PC) 3650, at least one microclinical analyzer (μCA) 3620, and a microcontroller 3640 in communication with the at least one perfusion controller 3650 and the at least one microclinical analyzer 3620. The integrated bio-object microfluidics chip cartridge also has one or more of PC/μCA calibration solution vials 3632 and one or more perfusion reservoirs and drug vials 3630 in communication with the at least one perfusion controller 3650 and the at least one microclinical analyzer 3620. The integrated bio-object microfluidics chip cartridge in one embodiment may also have a power supply 3642. Further, the integrated bio-object microfluidics chip cartridge has a bio-object chamber 3660. Additionally, the controller can be a wireless controller.

In another embodiment, the integrated bio-object microfluidics chip includes at least one fluidic network formed in the chip carrier. The at least one fluidic network comprises a plurality of inlets for providing a plurality of fluids, a plurality of outlets, a bio-object chamber for accommodating at least one bio-object, a plurality of fluidic switches, and one or more pumps. The bio-object chamber, the plurality of fluidic switches, and the one or more pumps are coupled to each other such that at least one fluidic switch operably and selectively receives one fluid from a corresponding inlet and routes the received fluid, through the one or more pumps, to the bio-object chamber so as to perfuse the at least one bio-object therein, and one of the other fluidic switches operably and selectively delivers an effluent of the at least one bio-object responsive to the perfusion to a predetermined outlet, or to the at least one fluidic switch for recirculation. In one embodiment, the at least one fluidic network defines the at least one perfusion controller (PC) 3650.

In an exemplary embodiment shown in FIG. 36 the integrated bio-object microfluidics chip cartridge further comprises a reservoir 3631 coupled to the plurality of inlets for providing the plurality of fluids.

Additionally, the integrated bio-object microfluidics chip cartridge also comprises a microclinical analyzer 3620 coupled to the fluidic network for detecting properties of effluent of the at least one bio-object.

Further, the integrated bio-object microfluidics chip cartridge has a calibration solution reservoir 3632 coupled to the microclinical analyzer for calibration thereof.

Moreover, the integrated bio-object microfluidics chip cartridge may further comprise a microcontroller 3640 for controlling operations of the plurality of fluidic switches and the one or more pumps of the fluidic network and the microclinical analyzer, where the microcontroller is provided with at least one of a wireless communication protocol and a backup battery 3642.

Referring to FIG. 27, a system for analysis of the bio-object including an organ or a group of cells includes an integrated bio-object microfluidics chip 2700 and a plurality of vials formed outside the chip 2700 in areas 2780 and 2790. The vials are adapted for providing loading of the cells, media, drugs and calibration solutions, and for outputting waste, etc. The integrated bio-object microfluidics chip or Integrated Organ Microfluidic chip (IOM) 2700 is formed with a fluid network having a bio-object chamber 2760 for accommodating at least one bio-object, four fluidic switches/valves 2710, 2720, 2730 and 2740, two pumps 2751 and 2752, and a microclinical analyzer 2770. The bio-object chamber 2760, the first pump 2751, the first fluidic switch 2710, the second fluidic switch 2720, the microclinical analyzer 2770, the fourth fluidic switch 2740, the second pump 2752, and the third fluidic switch 2730 are coupled to each other in series. The first fluidic switch 2710 is further coupled to the plurality of inlets/vials for selectively receiving one of the plurality of fluids therefrom and routing the received fluid to the first pump that in turn pumps the received fluid to the bio-object chamber so as to perfuse the at least one bio-object therein. The effluent of the at least one bio-object responsive to the perfusion is then directed to the microclinical analyzer 2770 for analysis. According to the embodiment, the microclinical analyzer 2770 can be calibrated, as needed, by activating the third fluidic switch 2730 that is further connected to the vials of calibration solutions, the second pump 2752 and the fourth fluidic switch 2740.

Referring to FIGS. 28-30, an integrated bio-object microfluidics chip 2800 is shown according to another embodiment of the invention. The integrated bio-object microfluidics chip has a fluid network. The fluid network comprises a plurality of inlets for providing a plurality of fluids, such as media, drug 1, drug 2, a plurality of outlets, for example, a waste outlet and an analysis outlet, a bio-object chamber 2860 for accommodating at least one bio-object, first and second fluidic switches Valve 1 and Valve 2, and a pump 1. The bio-object chamber, the first and second fluidic switches, and the first pump are coupled to each other in series. The first fluidic switch is further coupled to the plurality of inlets for selectively receiving one of the plurality of fluids therefrom and routing the received fluid to the first pump that in turn pumps the received fluid to the bio-object chamber so as to perfuse the at least one bio-object therein. The second fluidic switch is further coupled to the plurality of outlets for selectively delivering an effluent of the at least one bio-object responsive to the perfusion to a predetermined outlet, or to the first fluidic switch for recirculation. Each fluidic switch comprises a rotary planar valve (RPV) having a number of selectively controllable channels, for example, Valve 1 has five channels 2821-2825, while Valve 2 has four channels 2831-2834.

Additionally, the integrated bio-object microfluidics chip also has a bio-object loading port coupled to the bio-object chamber for loading the at least one bio-object.

FIG. 29 shows channel selections by rotating the actuator 2811 and 2812 to select the desired fluid to perfuse the cells/organ and selectively route the effluent of the cells/organ responsive to the perfusion to a predetermined outlet destination. For example, as selected, the effluent of the cells/organ is recirculated in FIG. 30A, while exited to the waste outlet in FIG. 30B.

FIG. 31 shows another embodiment of an integrated bio-object microfluidics chip which includes a similar configuration. Additionally, the integrated bio-object microfluidics chip also includes a plurality of calibration solution ports for providing a plurality of calibration solutions for calibration, a third fluidic switch coupled to the plurality of calibration solution ports, a second pump coupled to the third fluidic switch, and a microclinical analyzer coupled between the second pump and the second fluidic switch. The third fluidic switch is further coupled between the bio-object chamber and the second fluidic switch.

FIG. 32 shows yet another embodiment of an integrated bio-object microfluidics chip which includes two fluidic networks 3210 and 3220, each of which is the same as that of the integrated bio-object microfluidics chip shown in FIG. 28. The two fluidic networks 3210 and 3220 are symmetrically formed in a chip carrier so that the bio-object chambers of the first and second fluidic networks are proximal to each other while separated by a thin barrier or a membrane 3230 that allows for signaling between the bio-object chambers of the first and second fluidic networks.

According to embodiments of the invention, the IOM Chip is sterilizable, and multiple configurations of pumps and valves are created for different experimental methodologies. Variations of this design are used to (1) perfuse a single organ or group of cells, (2) perfuse two groups of cells connected by a thin porous membrane or barrier, or (3) perfuse an organ with an on-board clinical analysis system, e.g., microclinical analyzer. To support these end goals, additional development has yielded a new valve design, spring-loaded tensioning motor heads, embedded strain gauge, and a multi-channel pump.

In the event that the IOM is fabricated from a gas-impermeable material, the IOM can include a gas-exchange membrane, membrane oxygenator, or RPPM-controlled gas injection.

The valve designs, as illustrated in FIGS. 5 and 9-13, utilize a circular ball bearing cage with microfluidic interconnects underneath. The compression pressure from the ball bearings acts to occlude these microfluidic channels acting as a valve. The compression pressure is produced by rotating balls. The principal novel component of this design is the placement of microfluidic channels inside the circular path described by rotating balls in the ball cage. Multiple configurations of this design are examined, each with very low dead fluid volume.

As shown in FIG. 9, the rotary planar valve (RPV) in this embodiment has an actuator having a circular ball-bearing cage 910 defining a plurality of equally spaced-apart openings 912 thereon, and a plurality of balls 915 accommodated in the plurality of equally spaced-apart openings 912 such that at least one opening accommodates no ball bearing. Each two adjacent openings 912 through the center of the circular ball-bearing cage define an angle $\theta=2\pi/K$, K being the number of the plurality of equally spaced-apart openings.

Additionally, the RPV also has a plurality of selectively controllable channels, e.g., 921-923, positioned under the actuator in relation to the plurality of equally spaced-apart openings such that at least one selectively controllable channel is positioned under the at least one no-ball opening, for example, channel 922, so that a fluid flow is allowed through the open channel 922, while the other selectively controllable channels 921 and 923 are respectively positioned under the openings having the ball bearings so that no fluid flows are allowed through the other selectively controllable channels. For such a design, when rotating the actuator by a desired angle of $(k \times \theta)$, k being 1, 2, . . . K, the at least one no-ball opening is selectively placed over a desired one of the selectively controllable channels.

Further, the RPV has at least one always-open channel, for example, 924a and 924b positioned under the actuator in offset from the plurality of equally spaced-apart openings, such that the offset channels 924a and 924b are in fluid communication with the selected open channel 922 under the no-ball opening, while the other channels 921 and 923 under the openings having the ball bearings 915 are closed. Two always-open channels improve flow and ensure continuous flow during switching, if desired.

As shown in FIG. 9, each of the at least one always-open channels and the plurality of selectively controllable channels has an end connected to an arc fluidic path or a circular fluidic path 930.

For such an arrangement shown in FIG. 9, the ball bearings 915 occlude channel outputs from the valve; by convention, the circular ball-bearing cage 910 is rotated in increments of 45 degrees, and the pump driving the fluid is turned off while the circular ball-bearing cage 910 is being rotated; all controllable channels are on multiples of 45 degrees; always-open channels are offset by 22.5 degrees, i.e., 22.5+N*45 degrees, and any missing ball allows a controllable channel to be open.

FIG. 10 shows different embodiments of the RPV according to the invention. Each of the at least one always-open channels and the plurality of selectively controllable channels has an end connected to an arc fluidic path, as shown in FIG. 10A, or a circular fluidic path, as shown in FIG. 10B.

As shown in FIG. 11, four selectively controllable channels 1121-1124 are connected to corners of a square fluidic path 1130, as shown in FIG. 11A, and the actuator 1110 is configured such that when rotating by the desired angle of $(k \times \theta)$, the top-left and top-right channels 1121 and 1124 are in fluid communication with each other through the top portion 1134 of the square fluidic path 1130, and the bottom-left and bottom-right channels 1122 and 1123 are in fluid communication with each other through the bottom portion 1132 of the square fluidic path 1130, as shown in FIG. 11C; or the top-left and bottom-left channels 1121 and 1122 are in fluid communication with each other through the left portion 1131 of the square fluidic path 1130, and the top-right and bottom-right channels 1124 and 1123 are in fluid communication with each other through the right portion 1133 of the square fluidic path 1130, as shown in FIG. 11B.

As shown in FIG. 12, three selectively controllable channels 1221-1223 are connected in a T-like junction, and the actuator 1210 is configured such that when rotating by a desired angle of $(k \times \theta)$, two of the three channels, for example, channels 1221 and 1223, are in fluid communication with each other, while the other channel, e.g., channel 1222, is closed. This configuration allows fluid to enter from 1223 and exit through either 1221 or 1222. Alternatively, the top channel, 1223 could be closed while fluid could flow freely between 1221 and 1222.

FIG. 13 shows the RPV according to another embodiment of the invention, which is corresponding to a double valve with a single actuator. The double valve has first and second always-open channels 1324 and 1344 positioned under the actuator 1310 in offset from the plurality of equally spaced-apart openings 1312, a first plurality of selectively controllable channels 1321, 1322, 1323 and 1325 and a second plurality of selectively controllable channels 1341, 1342, 1343 and 1345. The first always-open channel 1324 and the first plurality of selectively controllable channels 1321, 1322, 1323 and 1325 are connected to a first arc fluidic path 1331, and the second always-open channel 1344 and the second plurality of selectively controllable channels 1341, 1342, 1343 and 1345 are connected to a second arc fluidic path 1332. The first and second arc fluidic paths 1331 and 1332 are arranged in a circle and not in fluid communication with each other. As such, in operation, the first always-open channel 1324 is selectively in fluid communication with one of the first plurality of selectively controllable channels 1321, 1322, 1323 and 1325, while the second always-open channel 1344 is selectively in fluid communication with one of the second plurality of selectively controllable channels 1341, 1342, 1343 and 1345.

In one embodiment, the actuator utilized in the RPV can also be used in the RPPM as a driving force of the pump. In addition, the RPPM also has an input channel and an output channel positioned under the actuator in relation to the plurality of equally spaced-apart openings such that when the actuator is rotated, a fluid flow is pumped from the input channel to the output channel.

In one embodiment, as shown in FIG. 14, each of the RPVs and the RPPMs further comprises a motor for rotating the actuator incrementally by the angle θ. The motor comprises a spring-loaded tensioning motor head or a self-tensioning motor head to ensure that the proper compressive force is delivered to the microfluidic channels. The self-tensioning motor head comprises a cylinder body 1461, where the cylinder body 1461 has one or more helically cut slits 1462 around an axis 1465 of the cylinder body, or two or more horizontally cut slits 1464 alternatively in X and Y directions, as shown in FIG. 14 to provide the requisite compressive force by the balls upon the PDMS, and to accommodate for differences or time-variations in the thickness or stiffness of the PDMS.

In yet another embodiment shown in FIG. 15, a strain gauge 1590 is embedded within PDMS 1510. The ball beneath the strain gauge 1590 induces strain, which is detectable with a Wheatstone bridge and appropriate amplification circuitry, and can be used to determine RPPM or RPV ball position. Accordingly, when the ball rolls over the gauge, the resistance changes and the ball position is inferred.

FIG. 16 shows the RPV and the RPPM as stand-alone units as related to the embodiments of the invention.

As shown in FIG. 17, two channels 1720 and 1730 are employed in a PDMS RPPM pumphead 1710 for pumping different materials, e.g., air or vacuum in one channel and fluid in the other. The more channels and/or ball circles there are, the more options there are. Channel widths can be modulated to provide different pumping rates per revolution.

In addition, according to embodiments of the invention, other rotary means of actuation, for example, cam follower, wheels, and caster valves/pumps, etc., as shown in FIGS. 44-50, can also be utilized to practice the invention.

FIG. 44A shows schematically a design of one particular microfluidic compatible rotary planar device with design features that can be used either for use as a pump or as a valve. Two key advantages of this design are: 1) the critical pre-use tensioning of the roller balls against the flexible membrane is easily achieved by simply placing a known weight or force against the rigid pressure holding plate; and 2) the ball bearing cage is implemented as ball containing sockets directly and rigidly attached to the drive pin. For pre-tensioning, once appropriate pressure has been added (possibly via a calibrated donut shaped weight) then simply tightening the holding screws will establish a known compressive force underneath the ball bearings to actuate the desired pump or valve functionality. The pressure transfer bearing located under the pressure holding plate acts to enable low friction rotation of the Teflon or other low-friction drive bearing while at the same time providing uniform downward force pressure on the Teflon drive bearing. Since the shaft rotation is rigidly linked to the Teflon drive bearing, it allows for direct transfer of the rotation delivered either from a motor or a hand crank via interface collar to the fluid driving ball bearings. When the central shaft is rotated, typically via a motor or a hand crank, the rotary force is transferred to a Teflon or other low friction material which holds individual ball bearings captive in ball cages. Alternatively shafted roller bearings could be used to transfer force into the deformable membrane. A rotary encoder assembly can be used to provide electronic verification of ball speed and precise ball location—a critical parameter when the device is utilized as a rotary planar valve assembly.

FIG. 44B shows bottom views of a drive bearing indicating that (a) balls and (b) rollers are housed within the sockets, according two embodiments of the invention. The drive bearing is utilized in the rotary planar device shown in FIG. 44A.

FIG. 45 shows a variation of the pumping module shown in FIGS. 44A and 44B where pumping channels are fabricated in hard plastics and covered with a flexible membrane forming one of the microfluidic channel sides. The membrane allows for channel closure when pressure is delivered by a rolling ball bearing. The hard plastic fluidic channel can be fashioned with semi-circular cross section to facilitate valve sealing.

FIG. 46 shows various implementations of an axle-driven, cam-follower-bearing type actuator used to implement the RPPMs and RPVs according embodiments of the invention. The actuator has a cam 4610 and a plurality of cam followers 4620 spaced-equally mounted onto the cam 4610, as shown in FIG. 46A. In another embodiment, the plurality of cam followers 4620 mounted onto the cam 4610, but not spaced-equally mounted, as shown in FIG. 46B, where there is no cam follower mounted at a location 4630. Further, the location 4630 is installed with a position indicator 4640, as shown in FIG. 46C.

FIG. 47 shows various implementations of an axle-driven, roller-bearing type actuator used to implement the RPPMs and RPVs according embodiments of the invention. The actuator has a wheel 4710 and a plurality of rollers 4720 mounted into the spaced-equally sockets, as shown in FIG. 47A. In another embodiment, one socket 4730 does not house a roller, as shown in FIG. 47B, where there is no cam follower mounted at a location 4730. Alternatively, the socket 4730 is installed with a position indicator 4740, as shown in FIG. 47C.

FIG. 48 shows the design of a roller or ball bearing caster pump assembly that can be used to create a peristaltic pump when used in conjunction with a planar microfluidic channel covered by a flexible membrane. The design incorporates a roller bearing mounted at an approximate 45 degree angle on a motor driven shaft. As the motor shaft rotates, the portion of the roller bearing in contact with the planar flexible membrane will trace a circular path on top of the embedded fluidic channel. Only one rounded edge of the roller or ball bearing outer rim will be in compressional contact with the flexible membrane, and the rolling rim bearing action will exert minimal frictional sliding force on the flexible membrane, thus creating as a very efficient long lived pump. This approximate 45 degree rotary caster design can also be used to provide rotary actuation of planar valve assemblies. An important feature of this design is that rotary shaft encoders can be easily attached to the rigid shaft coupling to provide exact information as to which portion of the circular arc contact region is currently compressed—thus facilitating exact control over planar fluid switch connection modes. The device is identified as a "rotary caster actuator" for planar microfluidic pumps or planar microfluidic valves, which can be used to compress flexible membranes for providing either pumping or valving functionality. This device is comprised of a central shaft with an angularly mounted ball or roller bearing assembly that contains an outer rim which will roll along a circular path when the central shaft is rotated. This device provides low sliding frictional force and hence low wear against the flexible membrane of a planar valve or pump component. Additionally, this device supports the use of standardized rotary encoder assemblies for the purpose of determining exact valve actuation position information or exact rotary pump speed information.

In one embodiment, the pumping device with direct drive and encoder includes (a) socket ball bearing cage made of low friction polymer, like a Teflon, directly attached to a rotary drive shaft; (b) pressure holding plate that is held in place by holding screws and transfers the tensioning pressure to the drive bearing via pressure transfer bearing; (c) pressure transfer bearing that can be either stand alone part or be integral part of the drive bearing; (d) rotary encoder; and (e) interface collar to provide attachment of a drive motor or a hand crank. In operation, microfluidic channels are located within the flexible membrane and placed under the device. In one embodiment, the device can be used as a manually or attached motor actuated rotary valve with the attached encoder proving feedback indication of the ball bearing position.

In one embodiment, the microfluidic channels are fabricated in hard plastic and are sealed with a flexible membrane with the ball bearing of the drive bearing acting on the flexible membrane.

FIG. 49 shows the conceptual design of a spring loaded pressure inverter which is comprised of a rotary array of actuators that can be used to provide a plurality of normally-closed fluidic channel connections which are driven by a central motorized rotary device, such as that illustrated in FIG. 48, or alternatively by any of the ball bearing cage RPV actuators described previously. The device operates on the basis of an embedded or otherwise rigidly mounted fulcrum which can transform the downward pressure associated with a tensioned ball bearing, or roller bearing into an upward force that can open a normally closed microfluidic valve. In this conceptual visualization eight Normally Closed (N.C.) microfluidic valves are located in the central region of the planar assembly. The device assembly identified as a "spring loaded pressure inverter" which can be utilized to convert the downward pressure exerted by a ball or roller bearing rotary actuator assembly into an upward force capable of opening a normally closed microfluidic channel.

FIG. 50 shows additional views of the conceptual design for a spring loaded pressure inverter actuation device for opening normally closed microfluidic valves. Note that the illustrated conceptual compression springs provide a force which is translated via a fulcrum mounted lever to provide the downward force that keeps a microfluidic channel closed. Only when external force is applied to a lever by a rotary actuator element will the associated microfluidic valve location be opened. Note especially that this is a conceptual diagram, and that actual physical implementation of the assembly might utilize flexible elastomers to provide spring forces and one-piece integrated fulcrum flexure units to act as levers.

The principal novel features of the IOM Chip devices and their respective carriers/cartridges, as illustrated in FIGS. 28-36, are:

(1) In various implementations of the Chip Carrier/Organ Cartridge, multiple fluidic reservoirs and either multiple pumps, or pumps used in conjunction with fluidic input and/or output valves, could be used to deliver various combinations of cell media, drugs, and other liquid compounds to the biological material in the chip.

(2) In other embodiments of the Chip Carrier/Cartridge, multiple fluidic reservoirs and either multiple pumps, or pumps used in conjunction with multi-position fluidic input valves, could be used in order to deliver various combinations of cell media, drugs, and other liquid compounds to the biological material in the chip. These reservoirs can be integral to the chip, with either a distensible boundary to allow filling or emptying, or a fixed volume with a bacteriostatic air filter to allow the introduction of air as fluid is removed by the on-chip pump, and vice versa.

(3) In other embodiments of the Chip Carrier/Cartridge, multiple fluidic reservoirs and either multiple pumps, or pumps used in conjunction with multi-position fluidic input valves and bubble traps, could be used to deliver various combinations of cell media, drugs, and other liquid compounds to the biological material in the chip.

(4) A key feature of the Invented Chip Carrier/Cartridge is the inclusion of an electronic microcontroller and an on-board battery. The purpose of the microcontroller is to provide signals to the pump(s) and fluidic valve assemblies that feed the biological material in the Organ Chip assembly, and utilize other sensors to control processes and/or conditions on the Chip Carrier/Cartridge. The purpose of the battery is to allow autonomous operation of the pumps and valves in the carrier when it has been disconnected from its standard power supply, for example, during transport or while being examined microscopically or chemically.

(5) A key feature of the Invented Chip Carrier/Organ Cartridge/IOM Chip interface that comprises the Organ Cartridge is the pump and valve fluidic driving heads that sit on the surface of the IOM Chip. The mechanism of operation of these pumps and valves is to occlude channels in the flexible surface layer of the IOM Chip and either move fluid in the case of the pumps or occlude fluid flow in the case of valves.

(6) A key feature of the Invented Chip Carrier/Cartridge is the ability of the microcontroller to implement complicated fluid and drug delivery protocols to the biological material on the chip. The protocols can be preloaded into the microcontroller and the chip carrier/cartridge can implement these fluid delivery instructions without human intervention.

(7) The microcontroller can also make autonomous decisions regarding pumps and valves based upon the output of embedded sensors.

(8) A key feature of the Invented Chip Carrier/Cartridge design is the closed fluid delivery system which can be sterilized without requiring sterilization of the driving electronics, motors, and sensors. This is extremely important in the context of long-term cell culture experiments, as the sterile barrier is never breached within the IOM Chip even while it is being transported, for example, between incubator and microscope.

(9) A key feature of the Invented Chip Carrier/Cartridge design is the ability of this design to accommodate in-line and intra-device fluid de-bubbler assemblies. These fluid de-bubbler assemblies are designed to prevent entry of small bubbles into cell assemblies or fluid delivery channels. These de-bubbling assemblies could be stand-alone devices or integrated into a complete microfluidic device.

(10) A key feature of all implementations of the Invented IOM Chip is that it has very low recirculating dead volume which allows for faster accumulation of cell signaling factors and avoidance of their dilution to levels below what is required for physiological effects.

(11) A key feature of the basic implementations of the Invented IOM Chip is that all fluidic connections between the pumps and valves are fabricated internally. The only external connections are to the stock solutions, to other organs in a coupled microphysiological system, or to storage vials for waste or analysis.

(12) A key advantage of the Invented Chip Carrier/Cartridge design is that the fluidic system is completely enclosed. This offers the additional advantage of allowing use in low humidity incubators, which are less likely to corrode electrical contacts and less likely to support fungal and bacterial contamination.

(13) The Invented Chip Carrier/Cartridge could also include on-board temperature regulation, so that the chips could be maintained at a desired operating temperature, either above or below the ambient temperature, without the need for an external incubator.

(14) The Chip Carrier/Cartridge can include fluid flow and fluid pressure sensors.

Bubbles are a common problem in microfluidic devices, and can be particularly troubling if the device contains living cells. The rate of bubble formation and growth depends in part upon whether the system is operating under positive or negative pressure. Although it is possible to run an entire system at a negative pressure relative to atmosphere, this would reduce the available gases in the media and could adversely affect the metabolism of the cells. Bubbles can form in negative pressure fluid channels because the dissolved gas will tend to accumulate on any nucleation site within the channel. Positive pressure is more likely to prevent bubbles than negative as long as bubbles are not already in the channel. Once a bubble is formed in a negative pressure system, it will grow continuously. In a positive pressure system, bubbles tend to reduce their size as the gas is pressed through the PDMS and their solubility is increased with pressure. It is possible to reduce bubble formation during fluid loading and pumping by making the fluid channels hydrophilic. Temperature gradients also influence bubble formation within the microfluidic channels. It is feasible that in a system with distributed sub-assemblies, temperature differences between sub-assemblies can alter the solubility of gases in the solutions and lead to spontaneous bubble formation.

To avoid the damage to cells from any bubbles that might be introduced into a microfluidic Organ Chip by either the surfaces of the chip or by the interfaces to perfusion controller or the microclinical analyzer, an in-line bubble trap is developed and utilized for long-term cell cultures in the perfusion controller and/or the microclinical analyzer in which bubbles are isolated from the primary flow by a forest of posts. The bubbles rise to a closed chamber above the post forest and, if necessary, may be withdrawn through an external valve, either using system pressure and a liquid-impermeable membrane or external suction, with the valve located either directly on the Organ Chip or integrated with the perfusion controller. It is also possible to remove small air bubbles through PDMS by applying negative pressure.

FIGS. 18-22 show different embodiments of a bubble trap utilized in a perfusion controller and a microclinical analyzer of organ chips.

As shown in FIGS. 19A, 19B, 19C and 20A, the bubble trap has two levels of microfluidic channels defining a fluidic compartment therebetween with a vertical via connecting the first and second microfluidic channels; an optional bubble accumulation chamber can be placed above the via. This via; serves as a bubble withdrawal channel or a bubble accumulation chamber; and provided a hydrophobic gas exchange membrane is placed between the via and the bubble withdrawal channel, thereby separating the fluidic compartment from the bubble. Shown in FIG. 19C is an alternative implementation of the straight channel bubble trap that minimizes possible dead volume associated with the introduction of bubble accumulation chamber within the flow path of the fluid within the via.

As shown in FIG. 19D, the bubble trap comprises a microfluidic channel containing a dense forest of micropillars within the fluidic path which act as bubble sieves to catch passing bubbles while providing alternative parallel paths for fluid to move freely beneath or around them. Included in this design is a bubble accumulation chamber directly over the micro-pillars designed to isolate the bubbles.

Further, as shown in FIGS. 18 and 19A, a ceiling of the bubble accumulation chamber is formed of a hydrophobic gas exchange membrane that allows for bubble removal either from passive diffusion into the atmosphere or from applied gentle vacuum.

As shown in FIG. 21, bubbles can be trapped using a two-layer microfluidic architecture. The lower layer contains the fluidic input, with bubbles, that is distributed laterally by a flow splitter and then into a wide forest of microposts that arrest the bubbles. The bubbles rise into the closed accumulation volume above the microposts, where they either diffuse into the PDMS or are drawn off occasionally through a separate port. The bubble-free fluid continues in the lower-layer channels, past the posts, and then into the cell-culture region. The advantage of this approach, in contrast to the more common practice of using microfabricated filters or fences to block bubbles from downstream cell culture regions, is that the low flow allows for better trapping of bubbles because the bubbles accumulate directly above the posts and thus the difficulty in clearing the bubbles from the filter/fence is avoided. With this approach, the accumulating bubbles do not impede fluid flow and can be drawn off whenever they fill the accumulation volume. It is important to realize that it is not desirable to load cells through the bubble trap, but they could be loaded either by reversing flow from the outlet, or with a separate cell-loading port.

FIG. 22 shows another embodiment of the bubble trap, which is corresponding to a somewhat more sophisticated design for a two-layer endothelial extravasation model, wherein cells roll, attach, and then migrate across a confluent layer of endothelial cells grown on a membrane with cell-permeable pores. (A) Block diagram of bubble trap containing bioreactor. The lower layer contains a splitter to evenly distribute flow throughout the device and a forest of posts to arrest bubbles. Above the forest of posts is an accumulation volume into which bubbles rise after being trapped. (B) Picture of fabricated cell culture bioreactor containing bubble trap. (C) A composite image of the bubbles (out of focus above the device) that have risen into the accumulation volume above the posts, with flow passing undisturbed underneath as indicated by the in-focus time lapsetrails of fluorescent beads suspended in fluid that is passing around the posts. (D) A test of accumulation of bubbles in the bubble trap by introducing a stream of bubbles with a bubble generator coupled to the bubble trap. Practical maximum volume of bubbles is approximately 80% of the accumulation volume. If the accumulation volume reaches capacity, a separate channel (not shown) can be used to aspirate them from the trap. This approach allows the trapping of bubbles in a two-compartment system with an intervening cell layer.

The de-bubbler assemblies (bubble traps) are designed to remove microscopic bubbles from the fluid contained within the microfluidic devices housed in IOM Chips. They can be either "stand alone" devices connected to the rest of the fluidic networks via tubing or direct overlay connections, or they can be integrated onto the microfluidic chips.

1) In its simplest implementation the bubble trap features two microfluidic channels located at different levels and connected by a vertical via and an accumulation chamber with a hydrophobic gas exchange membrane placed above the via. The hydrophobic membrane separates the fluidic compartment from the bubble withdrawal channels. It allows the air to escape while maintaining a fluid-impermeable hydrophobic barrier.
2) In some instances the withdrawal of the bubble through the membrane can be aided by applying a gentle vacuum on the air side. Such a vacuum can be provided by an on-board RPPM.
3) Another realization of the bubble trap consists of a microfluidic channel containing a dense forest of micropillars (posts) within the fluidic path that act as bubble sieves to catch passing bubbles while providing alternative parallel paths for fluid to move freely between them. Under certain conditions trapped bubbles will be collected in the bubble accumulation chamber placed directly above the pillars.
4) In some instances the ceiling of the bubble accumulation area includes a hydrophobic gas exchange membrane that would allow for bubble removal either from passive diffusion into the atmosphere or from actively applied gentle vacuum while preventing any liquid to escape.
5) In some instances (especially when handled liquid volumes must be minimized) the hydrophobic gas exchange membrane with the vacuum withdrawal network can be placed directly above the bubble-trapping pillars forming a gas permeable/liquid impermeable ceiling.
6) The hydrophobic properties of the trapping pillars and the gas exchange membrane can be enhanced with a thin film coating.

In one aspect of the invention, a method for analyzing a plurality of bio-objects includes the steps of providing a plurality of fluids; providing a fluidic network configured to be in fluid communication with the plurality of bio-objects and the plurality of fluids, wherein the fluidic network comprises a plurality of fluidic switches, one or more on-chip pumps and a plurality of fluidic paths connected therebetween; and controlling the plurality of fluidic switches and the one or more on-chip pumps to selectively and individually perfuse at least one of the plurality of bio-objects with at least one of the plurality of fluids at a predetermined perfusion flow rate and deliver an effluent of the at least one bio-object responsive to the perfusion to a predetermined outlet destination for analysis, recirculation, waste exhaust, or input to other bio-objects of the plurality of bio-objects.

The fluidic network further comprises a microclinical analyzer for detecting properties of the effluent of the at least one bio-object.

In one embodiment, the method further comprises the step of calibrating the microclinical analyzer.

In another embodiment, the method also includes the step of measuring a pressure drop across the at least one bio-object perfused with the at least one fluid, so as to regulate the flow rate of the at least one fluid through the at least one bio-object at the predetermined perfusion rate.

Further, the method includes the step of removing bubbles generated in the fluidic network.

Among other things, the invented Chip Carrier has, compared with FiberCell Systems Duet Pump hollow fiber bioreactor cartridges, at least the following advantages:
(a) The invented system allows more devices to reside in an incubator by reducing the size of the controlling electro-mechanical components.
(b) The invented system allows investigators to observe cells on a microscope, which is crucial for long-term investigative studies.
(c) The invented system provides convenient automatic drug delivery.
(d) The invented system could readily provide oxygenation of fluids at lower net volume.
(e) The invented system is compatible with many different microfluidic bioreactor designs.
(f) The invented system has a smaller ratio of cell volume to perfusate volume and can condition media more rapidly.
(g) The invented system is small enough to operate autonomously on a microscope stage.
(h) The invented system provides convenient automatic drug delivery with wireless control of the protocols.
(i) The on-board sensors of the invented system enable closed-loop control of the bioreactor.
(j) The invented system can provide closed-loop control of oxygen and $CO_2$ levels.
(k) A standardized footprint for sensors, pumps, and valves could be utilized to allow the Organ Cartridge to support a wide variety of Organ Chip configurations.
(l) The invented system utilizes fabricated, internal interconnects to provide on-chip pathways for circulating fluid.
(m) The microfabricated channels are shorter and smaller when compared against the FiberCell system.

In addition, the invented Chip Carrier has, compared with CellASIC ONIXb Microfluidic Perfusion Platform, the advantages of:
(a) The invented system controller costs less than $150.00 per Organ Cartridge.
(b) The invented system is compatible with many different microfluidic bioreactor designs.
(c) The invented system is self-contained, except for the long-term need for a source of electrical power to recharge the on-carrier batteries and the need for fresh nutrients to replace those metabolized by the bio-object.
(d) Multiple IOM Chip Carrier/Cartridges can operate autonomously in either an incubator or a microscope.
(e) With the standardized footprint approach, the system can be readily utilized with existing wellplate handling devices (i.e. microscopes, incubators, etc.).
(f) Multiple inexpensive integrated controllers render single, expensive, large controllers obsolete.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

REFERENCE LIST

[1] Schmidt, M and Lipson, H. Age-Fitness Pareto Optimization. In: Genetic programming theory and practice VIII, Riolo, R, McCongahy, T, Vladislavleva, E, eds. Springer, New York, 129-146, 2011

[2] Ly, D L, Lipson, H, Learning Symbolic Representations of Hybrid Dynamical Systems, J. Mach. Learn. Res. (In press), 2011

[3] Lima, E, Snider, R, Reiserer, R, Cliffel, D, Wikswo, J P. Multichamber Multipotentiostat System for Cellular Microphysiometry, Rev. Sci. Instrum., In preparation, 2011

[4] Fenn, L S and Mclean, J A. Simultaneous Glycoproteomics on the Basis of Structure Using Ion Mobility-Mass Spectrometry, Mol. Biosyst., 15, 1298-1302, 2009

[5] Enders, J R and Mclean, J A. Chiral and Structural Analysis of Biomolecules Using Mass Spectrometry and Ion Mobility-Mass Spectrometry, Chirality, 21, E253-E264, 2009

[6] Fenn, L S, Kliman, M, Mahsut, A, Zhao, S R, Mclean, J A. Characterizing Ion Mobility-Mass Spectrometry Conformation Space for the Analysis of Complex Biological Samples, Anal. Bioanal. Chem., 394, 235-244, 2009

[7] Mclean, J A. The Mass-Mobility Correlation Redux: the Conformational Landscape of Anhydrous Biomolecules, J. Am. Soc. Mass. Spect., 20, 1775-1781, 2009

[8] Harkness, K M, Cliffel, D E, McLean, J A. Characterization of Thiolate-Protected Gold Nanoparticles by Mass Spectrometry, The Analyst, 135, 868-874, 2010

[9] Kliman, M, Vijayakrishnan, N, Wang, L, Tapp, J T, Broadie, K, McLean, J A. Structural Mass Spectrometry Analysis of Lipid Changes in a Drosophila Epilepsy Model Brain, Mol. Biosyst., 6, 958-966, 2010

[10] Ridenour, W B, Kliman, M, McLean, J A, Caprioli, R M. Structural Characterization of Phospholipids and Peptides Directly From Tissue Sections by MALDI Traveling-Wave Ion Mobility-Mass Spectrometry, Anal. Chem., 82, 1881-1889, 2010

[11] Gant-Branum, R L, Broussard, J A, Mahsut, A, Webb, D J, Mclean, J A. Identification of Phosphorylation Sites Within the Signaling Adaptor APPL1 by Mass Spectrometry, J. Proteome. Res., 9, 1541-1548, 2010

[12] Sundarapandian, S, May, J C, McLean, J A. Dual Source Ion Mobility-Mass Spectrometer for Direct Comparison of Electrospray Ionization and MALDI Collision Cross Section Measurements, Anal. Chem., 82, 3247-3254, 2010

[13] McLean, J R, Mclean, J A, Wu, Z X, Becker, C, Perez, L M, Pace, C N, Scholtz, J M, Russell, D H. Factors That Influence Helical Preferences for Singly Charged Gas-Phase Peptide Ions: The Effects of Multiple Potential Charge-Carrying Sites, J. Phys. Chem. B, 114, 809-816, 2010

[14] Kerr, T J, Gant-Branum, R L, McLean, J A. Multiplexed Analysis of Peptide Functionality Using Lanthanide-Based Structural Shift Reagents, Int. J. Mass Spectrom., 307, 28-32, 2011

[15] Kliman, M, May, J C, McLean, J A. Lipid Analysis and Lipidomics by Structurally Selective Ion Mobility-Mass Spectrometry, Biochimica Et Biophysica Acta (BBA)-Molecular and Cell Biology of Lipids, 1811, 935-945, 2011

[16] Enders, J R, Goodwin, C R, Marasco, C C, Seale, K T, Wikswo, J P, Mclean, J A. Advanced Structural Mass Spectrometry for Systems Biology: Pulling the Needles From Haystacks, Spectroscopy Supp. Curr. Trends Mass Spectrometry, Jul. 18-23, 2011

[17] McLean, J A, Schultz, J A, Woods, A S. Ion Mobility-Mass Spectrometry for Biological and Structural Mass Spectrometry. In: Electrospray and MALDI mass spectrometry: fundamentals, instrumentation, practicalities, and biological applications, Cole, R B, ed. Wiley, Hoboken, N.J., 411-439, 2010

[18] May, J C and McLean, J A. The Conformational Landscape of Biomolecules in Ion Mobility-Mass Spectrometry. In: Ion Mobility Spectrometry-mass Spectrometry: Theory and applications, Wilkins, C L and Trimpin, S, eds. CRC Press, Boca Raton, Fla., 327-343, 2010

[19] Enders, J R, Kliman, M, Sundarapandian, S, Mclean, J A. Peptide and Protein Analysis Using Ion Mobility-Mass Spectrometry. In: Peptide and Protein Mass Spectrometry in Drug Discovery, Gross, M L, Chen, G, Pramanik, B, eds. J. Wiley & Sons, 139-174, 2011

[20] Fenn, L S and Mclean, J A. Structural Separations by Ion Mobility-Mass Spectrometry for Glycomics and Glycoproteomics. In: Mass Spectrometry of Glycoproteins: Methods and Protocols, Kohler, J J and Patrie, S M, eds. Humana Press, In press 2011

[21] May, J C, Goodwin, C R, Mclean, J A. Gas-Phase Ion Mobility-Mass Spectrometry and Tandem IM-MS Strategies for Metabolism Studies and Metabolomics. In: Encyclopedia of Drug Metabolism and Drug Interactions, Muddiman, D C, ed. Wiley & Sons, In press 2011

[22] Goodwin, C R, Fenn, L S, Derewacz, D K, Bachmann, B O, McLean, J A, Structural Mass Spectrometry: Rapid Methods for Separation and Analysis of Peptide Natural Products, J. Nat. Prod., 75:48-53, 2012

[23] Grant-Branum, R L, Kerr, T J, Mclean, J A. Relative Quantitation of Phosphorylated Peptides and Proteins Using Phosphopeptide Element-Coded Affinity Tagging (PhECAT), Anal. Chem., Submitted,-Location: (In press), 2011

[24] Matusch, A, Fenn, L S, Depboylu, C, Klietz, M, Strohmer, S, McLean, J A, Becker, J S, Combined Elemental and Biomolecular Mass Spectrometry Imaging for Probing the Inventory of Tissue at a Micrometer Scale, Anal. Chem., 33:128-133 2012

[25] Enders, J R, Marasco, C C, Kole, A, Nguyen, B, Sundarapandian, S, Seale, K T, Wikswo, J P, Mclean, J A. Towards Monitoring Real-Time Cellular Response Using an Integrated Microfluidics-MALDI/NESI-Ion Mobility-Mass Spectrometry Platform, IET Syst. Biol., 4, 416-427, 2010

[26] Kerr, T J and McLean, J A. Peptide Quantitation Using Primary Amine Selective Metal Chelation Labels for Mass Spectrometry, Chem. Commun., 46, 5479-5481, 2010

[27] Mclean, J A, Fenn, L S, Enders, J R. Structurally Selective Imaging Mass Spectrometry by Imaging Ion Mobility-Mass Spectrometry. In: Mass Spectrometric Imaging: History, Fundamentals and Protocols, Sweedler, J V and Rubakhin, S S, eds. Humana Press, New York, 363-383, 2010

[28] Fenn, L S and McLean, J A. Structural Resolution of Carbohydrate Positional and Structural Isomers Based on Gas-Phase Ion Mobility-Mass Spectrometry, Phys. Chem. Chem. Phys., 13, 2196-2205, 2011

[29] Schmidt, M D, Vallabhajosyula, R R, Jenkins, J W, Hood, J E, Soni, A S, Wikswo, J P, Lipson, H. Automated Refinement and Inference of Analytical Models for Metabolic Networks, Phys. Biol., 8, 055011 2011

[30] Yang, R, Lenaghan, S C, Wikswo, J P, Zhang, M. External Control of the GAL Network in S. Cerevisiae: A View From Control Theory, PloS. One., 6, e19353 2011

[31] Gant-Branum, R L, Kerr, T J, Mclean, J A. Labeling Strategies in Mass Spectrometry-Based Protein Quantitation, Analyst, 134, 1525-1530, 2009

[32] Fenn, L S and Mclean, J A. Biomolecular Structural Separations by Ion Mobility☐ Mass Spectrometry, Anal. Bioanal. Chem., 391, 905-909, 2008

[33] Fenn, L S and Mclean, J A. Enhanced Carbohydrate Structural Selectivity in Ion Mobility-Mass Spectrometry Analyses by Boronic Acid Derivatization, Chem. Commun., Issue 43, 5505-5507, 2008

[34] Mclean, J A and Russel, D H. New Vistas for Mass Spectrometry-Based Proteomics and Biotechnology: Rapid Two-Dimensional Separations Using Gas-Phase Electrophoresis/Ion Mobility-Mass Spectrometry, Am. Biotechnol. Lab., 23, 18-21, 2008

[35] Mclean, J A, Ridenour, W B, Caprioli, R M. Profiling and Imaging of Tissues by Imaging Ion Mobility-Mass Spectrometry, J. Mass Spectrom., 42, 1099-1105, 2007

[36] Mclean, J A, Ruotolo, B T, Gillig, K J, Russell, D H. Ion Mobility-Mass Spectrometry: a New Paradigm for Proteomics, Int. J. Mass Spectrom., 240, 301-315, 2005

[37] Ruotolo, B T, Mclean, J A, Gillig, K J, Russell, D H. Peak Capacity of Ion Mobility Mass Spectrometry: the Utility of Varying Drift Gas Polarizability for the Separation of Tryptic Peptides, J. Mass Spectrom., 39, 361-367, 2004

[38] Koomen, J M, Ruotolo, B T, Gillig, K J, Mclean, J A, Russell, D H, Kang, M J, Dunbar, K R, Fuhrer, K, Gonin, M, Schultz, J A. Oligonucleotide Analysis With MALDI-Ion-Mobility-TOFMS, Anal. Bioanal. Chem., 373, 612-617, 2002

[39] Chung, G G, Manbachi, A, Saadi, W, Lin, F, Jeon, N L, Khademhosseini, A. A Gradient-Generating Microfluidic Device for Cell Biology, JoVE, 7, http://www.jove.com/index/details.stp?id=271, doi: 3791/271 2007

[40] Saadi, W, Rhee, S, Lin, F, Vahidi, B, Chung, B, Jeon, N. Generation of Stable Concentration Gradients in 2D and 3D Environments Using a Microfluidic Ladder Chamber. Biomed. Microdevices, 9, 627-635, 2007

[41] Lin, F, Saadi, W, Rhee, S W, Wang, S J, Mittal, S, Jeon, N L. Generation of Dynamic Temporal and Spatial Concentration Gradients Using Microfluidic Devices, Lab Chip, 4, 164-167, 2004

[42] Dertinger, S K W, Chiu, D T, Jeon, N L, Whitesides, G M. Generation of Gradients Having Complex Shapes Using Microfluidic Networks, Anal. Chem., 73, 1240-1246, 2001

[43] Jeon, N L, Dertinger, S K W, Chiu, D T, Choi, I S, Stroock, A D, Whitesides, G M. Generation of Solution and Surface Gradients Using Microfluidic Systems, Langmuir, 16, 8311-8316, 2000

[44] Liu, Y, Sai, J G, Richmond, A, Wikswo, J P. Microfluidic Switching System for Analyzing Chemotaxis Responses of Wortmannin-Inhibited HL-60 Cells, Biomed. Microdevices, 10, 499-507, 2008

[45] Sai, J, Walker, G, Wikswo, J, Richmond, A. The IL Sequence in the LLKIL Motif in CXCR2 Is Required for Full Ligand Induced Activation of ERK, AKT and Chemotaxis in HL60 Cells, J. Biol. Chem., 281, 35931-35941, 2006

[46] Sai, J, Raman, D, Liu, Y, Wikswo, J, Richmond, A. Parallel Phosphatidylinositol 3-Kinase (PI3K)-Dependent and Src-Dependent Pathways Lead to CXCL8-Mediated Rac2 Activation and Chemotaxis, J. Biol. Chem., 283, 26538-26547, 2008

[47] Walker, G M, Sai, J, Richmond, A, Stremler, M A, Chung, C Y, Wikswo, J P. Effects of Flow and Diffusion on Chemotaxis Studies in a Microfabricated Gradient Generator, Lab Chip, 5, 611-618, 2005

[48] Thorsen, T, Maerkl, S J, Quake, S R. Microfluidic Large-Scale Integration, Science, 298, 580-584, 2002

[49] Squires, T M and Quake, S R. Microfluidics: Fluid Physics at the Nanoliter Scale, Rev. Mod. Phys., 77, 977-50, 2005

50. Unger, M A, Chou, H-P, Thorsen, T A, Scherer, A, Quake, S R, Microfabricated Elastomeric Valve and Pump Systems, U.S. Pat. No. 7,766,055, —2010

[51] Hansen, C L, Classen, S, Berger, J M, Quake, S R. A Microfluidic Device for Kinetic Optimization of Protein Crystallization and In Situ Structure Determination, J. Am. Chem. Soc., 128, 3142-3143, 2006

[52] Hansen, Carl L., Microfluidic technologies for structural biology, Ph.D. Dissertation, Caltech, May 28, 2004

[53] Hansen, C L, Sommer, M O A, Quake, S R. Systematic Investigation of Protein Phase Behavior With a Microfluidic Formulator, PNAS (US), 101, 14431-14436, 2004

[54] Darby, S, Moore, M, Wikswo, J P, Reiserer, R, Friedlander, T, Schaffer, D K, Seale, K T. A Metering Rotary Nanopump for Microfluidic Systems, Lab Chip, 10, 3218-3226, 2010

[55] Gould, P A, Hoang, L T, Scherrer, J, Matloff, W J, Hall, D J, Seale, K T, Wikswo, J P. Rotary Planar Peristaltic Micropump, Lab Chip, Submitted, 2011

[56] D. A. Markov, J. Q. Lu, P. Samson, J. P. Wikswo, and L. J. McCawley, "Thick-tissue bioreactor as a platform for long-term organotypic culture", Lab Chip, 12, pp 4560-4568, 2012

What is claimed is:

1. A microclinical analyzer usable for analysis of a plurality of bio-objects, each bio-object including an organ or a group of cells, comprising:

(a) a fluidic network having a plurality of fluidic switches, a plurality of fluidic paths in fluid communication with the plurality of fluidic switches, and one or more on-chip pumps coupled to corresponding fluidic paths, wherein the fluidic network is in fluid communication with the plurality of bio-objects and a plurality of fluids, wherein each fluidic switch comprises a rotary planar valve (RPV) and each on-chip pump comprises a rotary planar peristaltic micropump (RPPM), wherein each of the RPV and the RPPM comprises a rotary actuator, wherein the rotary actuator of the RPPM is adapted for operably pumping a fluid at a rate, and the rotary actuator of the RPV is adapted for operably rotating to selected positions to switch fluids in such a manner as to provide one or more bio-objects with selected fluids;

(b) a sensor array coupled to the fluidic network; and (c) a microcontroller for individually controlling the plurality of fluidic switches and the one or more on-chip pumps of the fluidic network to selectively and individually perfuse at least one of the plurality of bio-objects with at least one of the plurality of fluids at a predetermined perfusion flow rate, and selectively deliver an effluent of the at least one bio-object responsive to the perfusion to the sensor array for detecting properties of the effluent, or to a predetermined outlet destination.

2. The microclinical analyzer of claim 1, wherein the microcontroller comprises at least one of a wireless communication protocol and a backup battery.

3. The microclinical analyzer of claim 1, further comprising a calibration reservoir having a plurality of containers for containing the plurality of fluids, respectively, wherein the plurality of containers is coupled to at least one of the plurality of fluidic switches and the one or more on-chip pumps for individually providing the plurality of fluids to the sensor array for calibration.

4. The microclinical analyzer of claim 1, wherein each fluidic switch comprises a valve having at least one pole and a plurality of throws, wherein the at least one pole is operably and selectively in fluid communication with one of the plurality of throws.

5. The microclinical analyzer of claim 4, wherein the plurality of fluidic switches comprises first, second, and third fluidic switches, wherein the first fluidic switch comprises a one-pole four-throw valve coupled to the calibration reservoirs, the second fluidic switch comprises a four-pole three-throw valve coupled to the first fluid switch, the sensor array and the perfusion controller, and the third fluidic switch comprises a one-pole four-throw valve coupled to the on-chip pump and outlets and another bio-object, wherein the second and third fluidic switches are coupled to each other through the on-chip pump.

6. The microclinical analyzer of claim 1, wherein the rotary actuators comprise a circular ball-bearing cage defining a plurality of spaced-apart openings thereon, and a plurality of balls accommodated in the plurality of spaced-apart openings, wherein the number of the plurality of balls is same as that of plurality of spaced-apart openings of the circular ball-bearing cage, such that each opening of the circular ball-bearing cage accommodates a respective ball, or wherein the number of the plurality of balls is less than that of plurality of spaced-apart openings of the circular ball-bearing cage, such that at least one opening accommodates no ball.

7. The microclinical analyzer of claim 6, wherein the plurality of spaced-apart openings is spaced-equally defined on the circular ball-bearing cage, wherein each two adjacent openings through the center of the circular ball-bearing cage define an angle $\theta=2\pi/K$, K being the number of the plurality of equally spaced-apart openings.

8. The microclinical analyzer of claim 7, wherein the RPV further comprises a plurality of selectively controllable channels positioned under the actuator in relation to the plurality of equally spaced openings such that at least one selectively controllable channel is positioned under the at least one no-ball opening or under at least one no-ball location of the circular ball-bearing cage so that a fluid flow is allowed through the at least one selectively controllable channel, while the other selectively controllable channels are respectively positioned under the openings having the ball bearings so that no fluid flows are allowed through the other selectively controllable channels, wherein when rotating the actuator by a desired angle of $(k\times\theta)$, k being 1, 2, ... K, the at least one no-ball opening or no-ball location is selectively placed over a desired one of the selectively controllable channels.

9. The microclinical analyzer of claim 7, wherein the RPPM further comprises an input channel and an output channel positioned under the actuator in relation to the plurality of equally spaced-apart openings such that when the actuator is rotated, a fluid flow is pumped from the input channel to the output channel.

10. The microclinical analyzer of claim 1, wherein the rotary actuators comprise a wheel defining a plurality of spaced-apart sockets thereon in a circle, and a plurality of rollers accommodated in the plurality of spaced-apart sockets such that a rotation of the wheel causes the plurality of rollers to rotate along the circle.

11. The microclinical analyzer of claim 1, wherein the rotary actuators comprise a cam, and a plurality of cam-followers engaged with the cam such that a rotation of the cam causes the plurality of cam-followers to rotate along a circular path.

12. The microclinical analyzer of claim 1, wherein each of the RPV and the RPPM further comprises a motor for rotating the actuator.

13. The microclinical analyzer of claim 12, wherein the motor comprises a spring-loaded tensioning motor head or a self-tensioning motor head.

14. The microclinical analyzer of claim 1, wherein the rotary actuator of the RPPM operably pumps a fluid at a rate by actuating balls or rollers or cam-followers, and the rotary actuator of the RPV operably rotates balls or rollers or cam-followers to selected positions to switch fluids in such a manner as to provide one or more bio-objects with selected fluids.

* * * * *